United States Patent [19]

Eggler et al.

[11] Patent Number: 5,059,609

[45] Date of Patent: Oct. 22, 1991

[54] SUBSTITUTED TETRALINS, CHROMANS AND RELATED COMPOUNDS IN THE TREATMENT OF ASTHMA, ARTHRITIS AND RELATED DISEASES

[75] Inventors: James F. Eggler, Stonington; Anthony Marfat, Mystic; Lawrence S. Melvin, Jr., Ledyard, all of Conn.

[73] Assignee: Pfizer Inc., New York, N.Y.

[21] Appl. No.: 507,211

[22] Filed: Aug. 4, 1989

[51] Int. Cl.$^5$ ............... C07D 401/12; C07D 405/12; A61K 31/47; A61K 31/505

[52] U.S. Cl. ................... 514/314; 514/212; 540/492; 544/125; 544/333; 546/174; 546/176

[58] Field of Search ............ 546/174, 176; 514/314, 514/212; 544/125, 333; 540/492

[56] References Cited

U.S. PATENT DOCUMENTS

| | | | |
|---|---|---|---|
| 4,183,945 | 1/1980 | Doria et al. | 424/283 |
| 4,202,985 | 5/1980 | Hoehn | 546/176 |
| 4,363,811 | 12/1982 | Evans et al. | 424/267 |
| 4,576,949 | 3/1986 | Smith | 514/277 |
| 4,661,499 | 4/1987 | Young et al. | 514/311 |
| 4,661,596 | 9/1987 | Kreft, III et al. | 546/152 |

FOREIGN PATENT DOCUMENTS 0079637  5/1983  European Pat. Off. .
0190722  8/1986  European Pat. Off. .

*Primary Examiner*—David B. Springer
*Attorney, Agent, or Firm*—Peter C. Richardson; J. Trevor Lumb; Robert K. Blackwood

[57] ABSTRACT

Substituted tetralins, chromans and related compounds which, by inhibiting 5-lipoxygenase enzyme and/or blocking leukotriene receptors, are useful in the prevention or treatment of asthma, arthritis, psoriasis, ulcers, myocardial infarction and related disease states in mammals, pharmaceutical compositions thereof, a method of treatment therewith, and to intermediates useful in the synthesis thereof.

35 Claims, No Drawings

SUBSTITUTED TETRALINS, CHROMANS AND RELATED COMPOUNDS IN THE TREATMENT OF ASTHMA, ARTHRITIS AND RELATED DISEASES

BACKGROUND OF THE INVENTION

The present invention is directed to substituted tetralins, chromans and related compounds of the formula (I), depicted below, which by inhibiting 5-lipoxygenase enzyme and/or blocking leukotriene receptors, are useful in the prevention or treatment of asthma, arthritis, psoriasis, ulcers, myocardial infarction and related disease states in mammals. The present invention is also directed to pharmaceutical compoitions, a method of treatment, and to intermediates useful in the synthesis of said compounds of the formula (I).

Kreft et al., in U.S. Pat. No. 4,661,596, describe copounds which are disubstituted naphthalenes, dihydronaphthalenes or tetralins having the formula

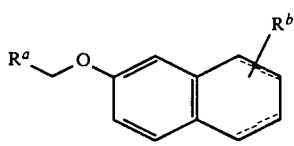

wherein the dotted lines represent optional double bonds, $R^a$ is 2-pyridyl, 2-quinolyl, 2-pyrazinyl, 2-quinoxalinyl, 2-thiazolyl, 2-benzothiazolyl, 2-oxazolyl, 2-benzoxazolyl, 1-alkyl-2-imidazolyl or 1-alkyl-2-benzimidazolyl and $R^b$ is hydroxy, lower alkoxy, lower alkyl or perfluoro alkyl. Like the compounds of the present invention, these compounds inhibit lipoxygenase enzyme and antagonize the effects of leukotriene D4, and so are useful in the prevention and treatment of asthma.

The chemical nomenclature employed herein generally follows that of "I.U.P.A.C. Nomenclature of Organic Chemistry, 1979 Edition," Pergammon Press, New York, 1979.

SUMMARY OF THE INVENTION

The present invention is directed to racemic or optically active compounds having the structural formula

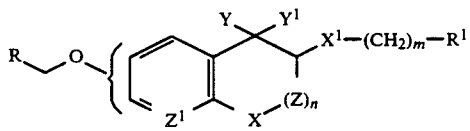

wherein
n is 0 or 1;
m is 0 or an integer from 1 to 3;
X is $CH_2$, O, S, SO, $SO_2$, NH or $N(C_1-C_4)$alkyl;
$X^1$ is $CH_2$, O, S, SO or $SO_2$;
Y and $Y^1$ are taken together and form a carbonyl group, or Y and $Y^1$ are taken separately, Y is hydrogen and $Y^1$ is hydroxy or an acyloxy group which is hydrolyzed to form a hydroxy group under physiological conditions;
Z is $CH_2$, $CHCH_3$, $CH_2CH_2$ or $CH_2CH_2CH_2$;
$Z^1$ is CH or N;
R is 2-, 3- or 4-pyridyl, 2-, 3-, 4 or 8-quinolyl, 1-, 3- or 4-isoquinolyl, 3- or 4-pyridazinyl, 3- or 4-cinnolinyl, 1-phthalazinyl, 2- or 4-pyrimidinyl, 2- or 4-quinazolinyl, 2-pyrazinyl, 2-quinoxalinyl, 1-, 2- or 3-indolizinyl, 2-, 4- or 5-oxazolyl, 2-benzoxazolyl, 3-, 4- or 5-isoxazolyl, 5-benzo[c]isoxazolyl, 3-benzo[d]isoxazolyl, 2-, 4- or 5-thiazolyl, 2-benzothiazolyl, 3-, 4- or 5-isothiazolyl, 5-benzo[c]isothiazolyl, 3-benzo[d]isothiazolyl, 1-[$(C_1-C_4)$alkyl]-2-, 4- or 5-imidazolyl, 1[$C_1-C_4)$alkyl]-2-benzimidazolyl, 1-[$(C_1-C_4)$alkyl]-3-, 4- or 5-pyrazolyl, 2-[$(C_1-C_4)$alkyl]-3(2H)-indazolyl, or 1[$C_1-C_4)$alkyl]-3(1H)-indazolyl; or one of said groups mono- or disubstituted on carbon with the same or different substituents which are bromo, chloro, fluoro, $(C_1-C_4)$alkyl, trifluoromethyl, hydroxy, hydroxymethyl or $(C_1-C_4)$alkoxy, or on adjacent carbons with trimethylene, tetramethylene, $—CH_2—O—CH_2—$ or $—O—CH_2—O—$; and $R^1$ is attached by means of aromatic or heteroaromatic carbon and is phenyl, naphthyl, pyridyl, quinolyl, isoquinolyl, pyridazinyl, cinnolinyl, phthalazinyl, pyrymidinyl, naphthyridinyl, pyrrolyl, N-[$(C_1-C_4)$alkyl]pyrrolyl, indolyl, N-[$(C_1-C_4)$alkyl]indolyl, isoindolyl, N-[$(C_1-C_4)$alkyl]isoindolyl, indolizinyl, pyrazolyl, 1-[$(C_1-C_4)$alkyl]pyrazolyl, indazolyl, 1-[$(C_1-C_4)$alkyl]-1H-indazolyl, 2-[$(C_1-C_4)$alkyl]-2H-indazolyl, imidazolyl, 1-[$(C_1-C_4)$alkyl]imidazolyl, benzimidazolyl, 1-[$(C_1-C_4)$alkyl]benzimidazolyl, furyl, benzofuranyl, isobenzofuranyl, oxazolyl, benzoxazolyl, isoxazolyl, benzo[c]isoxazolyl, benzo[d]isoxazolyl, thienyl, benzothiophenyl, isobenzothienyl, thiazolyl, benzothiazolyl, isothiazolyl, benzo[c]isothiazolyl, or benzo[d]isothiazolyl; or, only when either $X^1$ is $CH_2$ or m is at least 2, $R^1$ is attached by means of heterocyclic nitrogen and is 1-pyrrolyl, 1-indolyl, 2-isoindolyl, 1-pyrazolyl, 1(1H)-indazolyl, 2-(2H)-indazolyl, 1-imidazolyl or 1-benzimidazolyl; or $R^1$ is one of said groups which is mono- or disubstituted on carbon with the same or different groups which are bromo, chloro, fluoro, hydroxy, hydroxymethyl, $CF_3$, $(C_1-C_4)$alkyl, $(C_1-C_4)$alkoxy, carboxy, [$(C_1-C_4)$alkoxy]carbonyl, or substituted on adjacent carbons with trimethylene, tetramethylene, $—CH_2—O—CH_2—$ or $—O—CH_2—O—$; or substituted on tertiary nitrogen to form an N-oxide;

a pharmaceutically acceptable acid addition salt thereof; or a pharmaceutically acceptable cationic salt when the compound contains a carboxy group.

Because of their ease of preparation and valuable biological activity, in the preferred compounds of the formula (I), regardless of the value of Y and $Y^1$, n is 1, m is 0, X and $X^1$ are each independently $CH_2$ or O, Z is $CH_2$, $Z^1$ is CH, R is 2-, 3- or 4-pyridyl, 2-quinolyl, 6-fluoro-2-quinolyl, 5-fluoro-2-benzothiazolyl or 2-pyrazinyl, and $R^1$ is phenyl, 3-methoxyphenyl, 4-methoxyphenyl, 3-methoxycarbonylphenyl, 4-methoxycarbonylphenyl, 3-carboxyphenyl, 4-carboxyphenyl, 2-pyridyl or 3-pyridyl.

In the most preferred compound when Y and $Y^1$ are taken together to form a carbonyl group, n is 1, m is O, X is O, $X^1$ is $CH_2$, Z is $CH_2$, $Z^1$ is CH, R is 2-quinolyl and $R^1$ is 3-pyridyl.

When Y is H and $Y^1$ is OH, most preferred are racemic or optically active compounds having the relative stereochemical formula

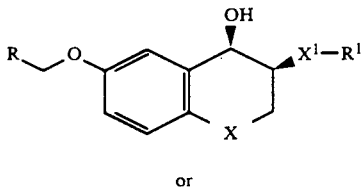

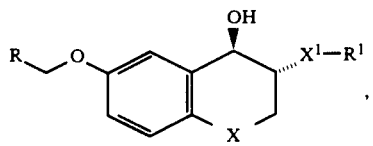

most particularly those racemic or optically active compounds of the formula (II) or (III) wherein X and $X^1$ are each O or $CH_2$, R is 2-quinolyl, 6-fluoro-2-quinolyl or 5-fluoro-2-benzothiazolyl, and $R^1$ is 3-pyridyl, 3-carboxyphenyl or 4-methoxyphenyl.

Said pharmaceutically-acceptable acid addition salts include, but are not limited to, those with HCl, HBr, $HNO_3$, $H_2SO_4$, $H_3PO_4$, $CH_3SO_3H$, $p-CH_3C_6H_4SO_3H$, $CH_3CO_2H$, gluconic acid, tartaric acid, maleic acid and succinic acid. In the case of those compounds of the formula (I) which contain a further basic nitrogen, it will, of course, be possible to form diacid addition salts (e.g., the dihydrochloride) as well as the usual monoacid addition salt. Said pharmaceutically-acceptable cationic salts include, but are not limited to, those of sodium, potassium, calcium, magnesium, ammonia, N,N'-dibenzylethylenediamine, N-methylglucamine (meglumine), ethanolamine and diethanolamine.

The reference to $Y^1$ as an acyloxy group which is hydrolyzed to a hydroxy group under physiological conditions refers to esters of a type which are frequently referred to as "pro-drugs." Such esters are now as well-known and common in the medicinal art as pharmaceutically-acceptable salts. Such esters are generally used to enhance oral absorption, but in any event are readily hydrolyzed in vivo to the parent hydroxy compound. The more preferred acyloxy groups are those in which the acyl moiety is the alpha-aminoacyl residue of a naturally occurring L-alpha-amino acid,

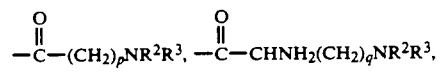

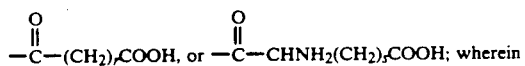

$R^2$ and $R^3$ are taken separately and are each independently hydrogen or ($C_1$-$C_4$)alkyl, or $R^2$ and $R^3$ are taken together with the nitrogen to which they are attached to form a pyrrolidine, piperidine, perhydroazepin or morpholine ring;

p is an integer from 1 to 4;
q is an integer from 1 to 3;
r is an integer from 2 to 3; and
s is an integer from 1 to 3.

Also forming a part of the present invention are pharmaceutical compositions for administration to a mammal which comprise a compound of the formula (I) and a pharmaceutically acceptable carrier; and a method of inhibiting 5-lipoxygenase enzyme and/or blocking leukotriene D4 receptors in a mammal, so as to prevent or treat asthma (particularly in man), arthritis, psoriasis, gastrointestinal ulcers, or myocardial infarction.

Finally, the present invention is directed to valuable intermediate compounds having the structural formula

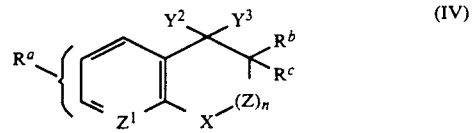

wherein
n, X, Z and $Z^1$ are as defined above;
in the first alternative
$Y^2$ and $Y^3$ are taken together and form a carbonyl group, or $Y^2$ and $Y^3$ are taken separately, $Y^2$ is hydrogen and $Y^3$ is hydroxy; and
$R^a$ is hydroxy or benzyloxy;
$R^b$ and $R^c$ are taken separately and $R^b$ is hydrogen and $R^c$ is $-X^1-(CH_2)_m-R^1$; and
m, $X^1$ and $R^1$ are as defiend above;
or in the second alternative
$R^b$ and $R^c$ are taken together and are hydroxymethylene or diazo; or $R^b$ and $R^c$ are taken separately, $R^b$ is hydrogen and $R^c$ is bromo;
$R^a$ is

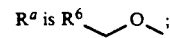

and
$R^6$ is phenyl or a value of R as defined above.
The preferred values of n, m, X, $X^1$, Z, $Z^1$, R and $R^1$ are also as defined above.

DETAILED DESCRIPTION OF THE INVENTION

The present invention is readily carried out. Without regard to geometrical (cis-trans) or optical isomers, the compounds of the formula (I) wherein $Y+Y^1=$ carbonyl, or Y=H and $Y^1=$OH, and $X^1=CH_2$, S or O are prepared according to the chemical transformations which are summarized in Flowsheets 1, 2 and 3, where the symbols n, m, X, Z, $Z^1$, R and $R^1$ are as defined above. The various transformations found in these flowsheets, as well as transformations required for the preparation of the compounds (I) having other values of Y, $Y^1$ and $X^1$, and methods for separation of cis-trans and optical isomers, are detailed below.

The condensation of Flowsheet 1 is typically carried out with the phenolic group in protected form as shown, methyl being a preferred protecting group only when $X^1$ is $CH_2$. The preferred conditions employ a molar excess of the required aldehyde and a molar excess of a secondary amine such as pyrrolidine or piperidine as base. (It is understood that such a base facilitates the condensation by forming an enamine intermediate.)

Flowsheet 1
When $X^1 = CH_2$
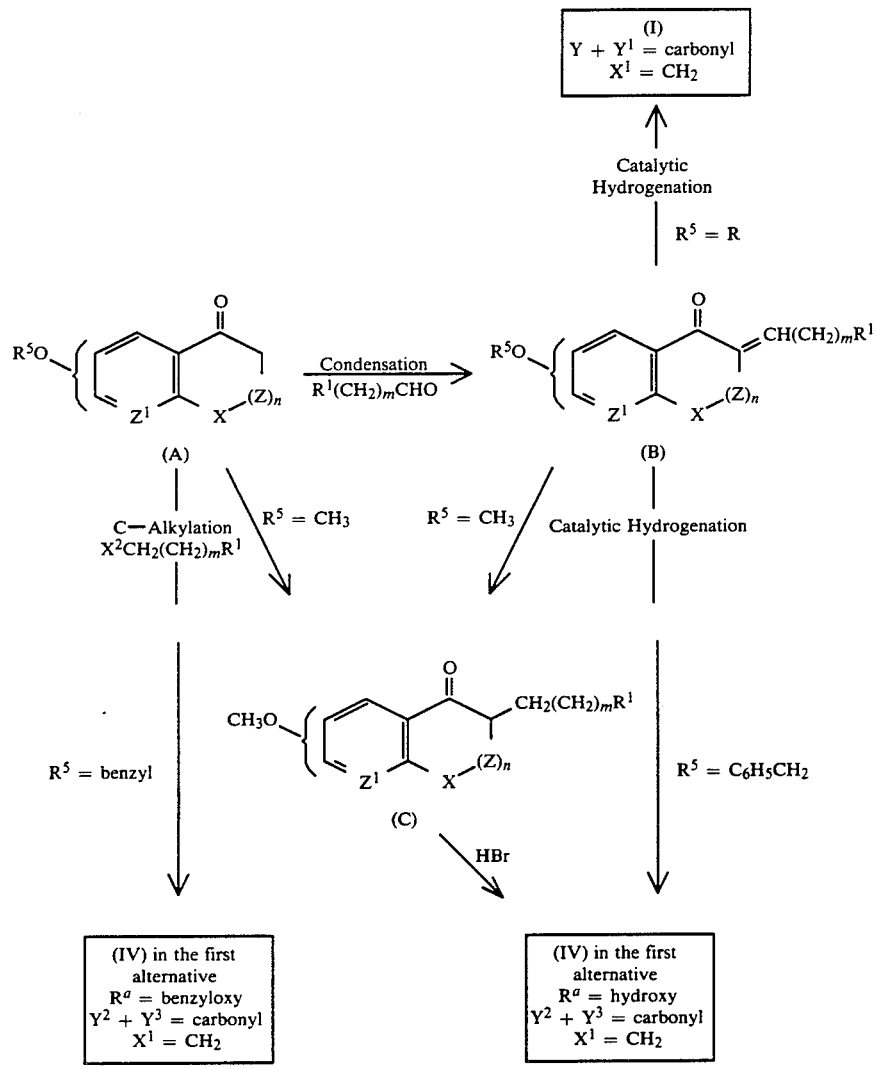
$R^5 = R$, $CH_3$, or $C_6H_5CH_2$
$X^2$ = Nucleophically displaceable group such as I, Br, Cl, $CH_3SO_3$ or p-$CH_3C_6H_4SO_3$
Flowsheet 2
When $X^1 = O$ or $S$
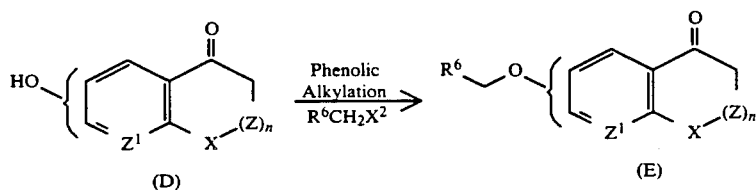

Flowsheet 2
When $X^1 = O$ or $S$
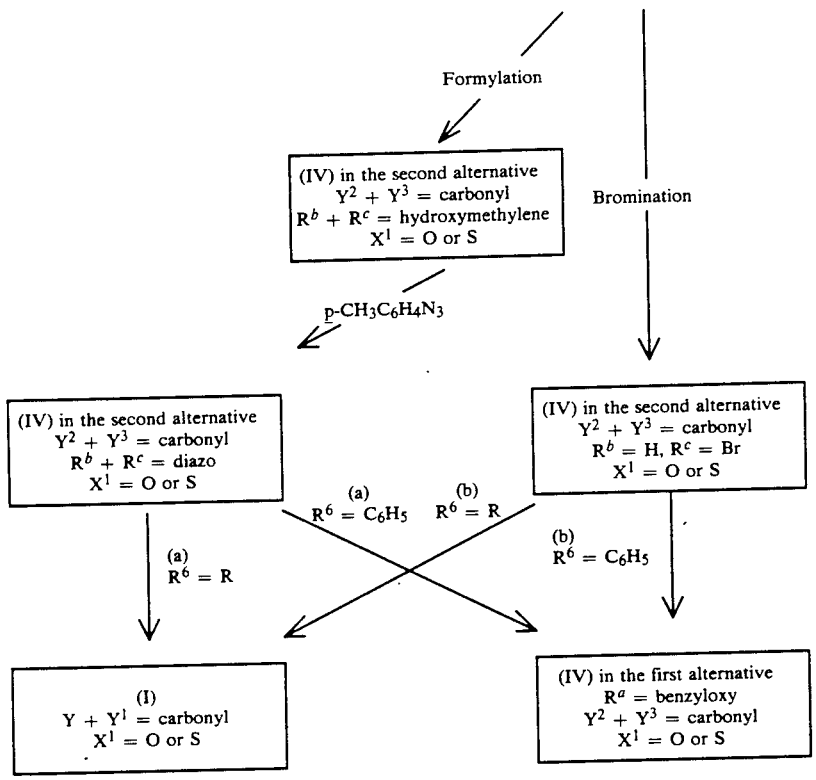
$R^6 = R$ or $C_6H_5$
$X^2 = Cl, Br, I, CH_3SO_3, p\text{-}CH_3C_8H_4SO_3$ or other nucleophilically displaceable group
(a) $R^1(CH_2)_mSH$ or $R^1(CH_2)_mOH$, rhodium (II) acetate dimer
(b) $R^1(CH_2)_mSH$ or $R^1(CH_2)_mOH$, base
Flowsheet 3
When $X^1 = CH_2$, O or S
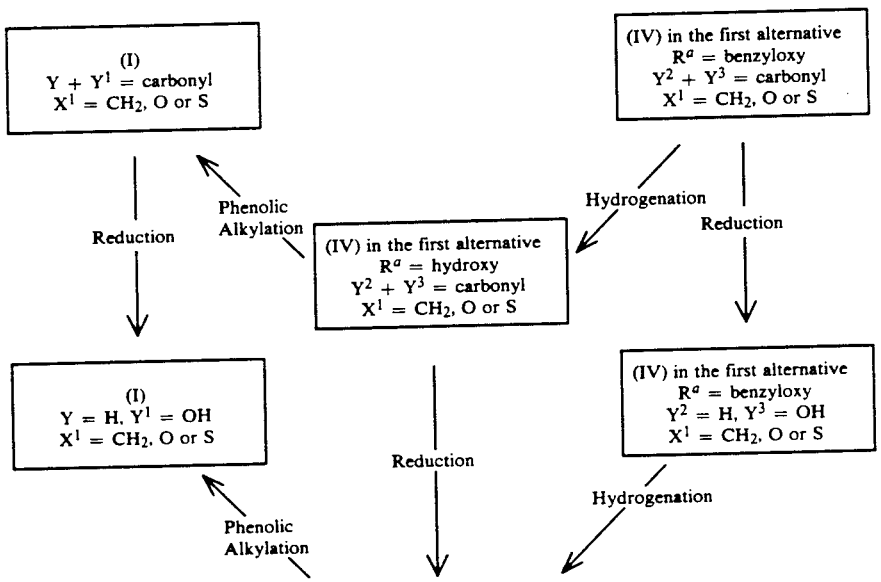

Flowsheet 3
When $X^1$ = $CH_2$, O or S

-continued (IV) in the first alternative
$R^a$ = hydroxy
$Y^2$ = H, $Y^3$ = OH
$X^1$ = $CH_2$, O or S The reaction is generally carried out in a reaction-inert solvent, lower alcohols such as methanol being particularly well suited for this purpose. The temperature conditions for this transformation are not critical, e.g., 0°-70° C. is generally satisfactory, with ambient temperature particularly well suited as a matter of convenience.

As used here and elsewhere herein, the expression "reaction-inert solvent" refers to a solvent which does not interact with starting materials, reagents, intermediates or products in a manner which adversely affects the yield of the desired product.

The C-alkylation of Flowsheet 1 is carried out by first converting the ketone (A) to its lithium salt, usually in situ, by the action of substantially one molar equivalent of a strong, sterically hindered base such as lithium diisopropylamide, usually carried out at low temperature (e.g., about −40° to −80° C. conveniently at the temperature of a dry ice-acetone bath). The salt in turn is reacted with the alkylating agent, preferably the highly reactive iodide, usually in molar excess in the presence of a molar excess of hexamethyl phosphoramide, now at higher temperature (e.g., about 0° to 40° C.). Conveniently, the latter reagents are added to the cold lithium salt solution, and the temperature allowed to rise to ambient temperature as the reaction proceeds. The salt preparation and alkylation reaction are usually carried out in the same reaction-inert solvent (e.g., tetrahydrofuran). It will be evident to those skilled in the art that any free hydroxy or carboxy groups in the alkylating reagent should be in protected form (vide supra).

The catalytic hydrogenation transformations (debenzylations, $H_2$-additions to double bond) of Flowsheets 1, 2 and 3 are carried out under conventional conditions, generally in a reaction-inert solvent, and preferably using a noble metal catalyst and moderate conditions of temperature (e.g., about 0° to 70° C.) and hydrogen pressure (e.g., about 1 to 10 atmospheres). While higher pressures may be desirable in selected instances, such moderate pressures permit the use of much less elaborate and expensive equipment. Suitable noble metal catalysts include platinum, palladium, rhenium, rhodium and ruthenium, either of the supported or non-supported type, as well as the known catalytic compounds thereof such as the oxides, chlorides, etc. Examples of suitable catalyst supports include carbon, silica and barium sulfate. The catalysts may be preformed or formed in situ by prereduction of an appropriate salt of the catalytic compound. Examples of preferred catalysts are 5% palladium-on-carbon, 5% platinum-on-carbon; 5% rhodium-on-carbon, platinum chloride, palladium chloride, platinum oxide and ruthenium oxide. Most preferred in the present instance is palladium-on-carbon. Solvents generally suitable for the present hydrogenation include lower alkanols, ethyl acetate and tetrahydrofuran.

The methyl ethers [compounds of the formula (C)] in Flowsheet 1 are deblocked to form the corresponding phenol derivative, again, by conventional methods; for example, using concentrated HBr, or $BBr_3$, both of which are exemplified below.

The phenolic alkylations found in Flowsheets 2 and 3 and the bromine replacement reaction of Flowsheet 2 each represent conventional nucleophilic displacement reactions. These displacements are generally carried out in the presence of a base of sufficient strength to convert the displacing phenol, alcohol or thiol to its salt, and in a quantity at least sufficient to neutralize the by-product acid ($HX^2$, HBr). In those substrates which contain an aliphatic alcohol group [e.g., a compound (IV) wherein $Y^2$ is H and $Y^3$ is OH], bases of sufficient strength to convert that group to the anion will generally be used in an amount no more than sufficient to convert the more acidic phenol to the salt. When either of the reactants contains a group of acidity similar to or greater than that of the nucleophilic displacing compound, such potentially interfering groups are best introduced in protected form (e.g., a heteroaromatic phenolic group as methoxy or benzyloxy, a carboxy group as methyl or benzyl ester, removable by hydrolysis or hydrogenolysis according to methods detailed elsewhere herein). The present nucleophilic displacements are carried out in a reaction-inert solvent, preferably one which is much less acidic than the displacing phenol, alcohol or mercaptan. Most preferred are polar, aprotic solvents such as dimethylformamide or acetone, usually with a molar excess of the more readily available of the two reactants.

Temperature is not critical, e.g., about 10°-70° C. is usually satisfactory with ambient temperature most convenient. In one preferred variant, the phenol, alcohol or mercaptan is irreversibly converted to the anion with a base such as sodium hydride. Other preferred variants employ $K_2CO_3$ as base in the presence of NaI, or $Cs_2CO_3$ as base in the presence of CsI.

In the special case of X=NH, such nucleophilic displacements will generally be carried out with the NH group protected, e.g., as the N-benzyl derivative (subsequently removed by hydrogenation) or as an N-alkanoyl or N-sulfonyl derivative (subsequently removed under appropriate hydrolysis conditions; for example, the N-tosyl derivative is hydrolyzed by heating in a mixture of acetic acid and concentrated HCl).

The formylation of Flowsheet 2 represents a conventional condensation type reaction of a ketone with an alkyl formate. This reaction is generally in an aprotic reaction-inert solvent such as toluene in the presence of a strong base such as sodium hydride at moderate temperatures (e.g., 0°-70° C., conveniently at ambient temperature). The subsequent conversion to the diazo compound is conveniently accomplished with tosyl azide as the reagent, a reaction generally carried out at low temperature (e.g., about −10° to −60° C.) in the presence of molar excess of a tertiary amine (e.g., triethylamine) in a reaction-inert solvent such as $CH_2Cl_2$. In turn, the diazo compound is reacted with an appropriate alcohol or mercaptan in the presence of a catalytic amount of rhodium (II) diacetate dimer to form the desired ether or thioether. The latter transformation is generally carried out in an anhydrous reaction-inert solvent such as toluene at somewhat elevated temperature, e.g., about 50°–100° C. Substituent alcohol or carboxy groups which are not intended to react are preferably protected in this transformation, as in the case of the nucleophilic displacement reactions discussed above.

The "reduction" reactions of Flowsheet 3 require the reduction of a ketone to a secondary alcohol, for which a number of selective reagents are available. Where no other $LiAlH_4$ reducible groups (such as carboxy, methoxycarbonyl) are present, that reagent is well suited for this purpose. On the other hand, $NaBH_4$ is preferred as the reducing agent when such reducible groups are present. In either case, these hydride reductions are generally carried out in a reaction-inert solvent (such as tetrahydrofuran in the case of $LiAlH_4$, methanol or a combination of methanol and tetrahydrofuran in the case of $NaBH_4$). In either case, temperature is not critical, about 0° to 50° C. being generally satisfactory and ambient temperature preferred. The present reduction step offers the potential of producing a mixture of cis- and trans-isomers [as illustrated in the formulas (II) and (III)] and in the present hydride reduction, that is the result which is generally observed. If one or the other of these isomers is particularly desired, one can usually find a reduction method and set of conditions which will favor the desired isomer. For example, $NaBH_4$ reduction in the presence of cesium chloride will generally strongly favor the cis-isomer. Catalytic hydrogenation is also a generally useful reduction method, generally carried out under conditions which are somewhat more vigorous than those described above (e.g., more prolonged time, higher catalyst level, higher temperature and/or higher pressure). Hydrogenation is preferably carried out on substrates such as

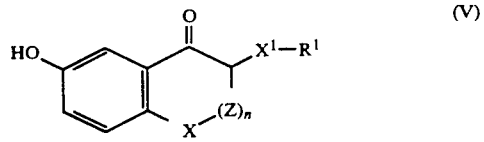

(V)

which contain no other readily hydrogenated group. Pd/C catalyst tends to particularly favor formation of cis-isomer. However, by variation of the catalyst and conditions, it will be possible to modify or even reverse that tendency. Where both cis- and trans-isomers form in the present reduction, they are generally separable by standard chemical methods (e.g., selective or fractional crystallization, chromatography, and so forth).

If compounds wherein $X^1$ is SO or $SO_2$ are desired, they are usually prepared from the corresponding compounds of the formula (I) or (IV) wherein the group $X^1$ as S is already in place. Peroxides are generally used as oxidizing agent. A particularly convenient reagent for this purpose is m-chloroperbenzoic acid. The sulfide is reacted with substantially 1 molar equivalent of this reagent to obtain the sulfoxide and with at least 2 molar equivalents to obtain the sulfone, in a reaction-inert solvent such as $CH_2Cl_2$. Temperature is not critical, e.g., 0°–60° C. being generally satisfactory and ambient temperature preferred. However, when X is S, and compounds wherein $X^1$ is SO or $SO_2$ are desired, these are preferably formed by conventional sulfinylation or sulfonylation of an unsubstituted ketone compound of the formula (A), (D) or (E).

Those ketone compounds of the formula (I) wherein Y and $Y^1$ form a carbonyl group, and of the formula (IV) in the first alternative, contain an asymmetric carbon at the alpha-position which is adjacent to the carbonyl group, and therefore are racemic compounds capable of resolution into optically active enantiomers, e.g., by conversion of the racemate into diastereomeric salts with an optically active acid, which are generally separable by a fractional crystallization process. Alternatively, if the substrate contains a carboxy group, separable diastereomeric salts are formed with an optically active organic amine. Optical activity can also be induced by use of an optically active reagent in the step by which the asymmetric carbon is formed, e.g., use of an optically active Wilkinson type catalyst, or a noble metal supported on an optically active support, in the hydrogenation step. The optically active ketones are also available by conventional reoxidation of an optically active alcohol of the next paragraph, e.g., via the Jones oxidation, which is exemplified below.

The hydroxy compounds of the formula (I) and (IV) wherein Y (or $Y^2$) is hydrogen and $Y^1$ (or $Y^3$) is OH contain two such asymmetric carbons—corresponding to two racemates and four optically active compounds. One of these racemates is the above noted cis-isomer, and the other the trans-isomer. Each of these racemates is capable of resolution into a pair of enantiomers via diastereomeric salts, as detailed in the preceding paragraph. It is preferred, however, to convert the racemic alcohol to corresponding diastereomeric esters or urethanes formed with an optically active acid or isocyanate. Such covalently bonded derivatives are generally subjectable to a broader variety of separation methods (e.g., chromatography) than are diastereomeric salts. Such diastereomeric esters are formed from the alcohol and the optically active acid by standard methods, generally those involving activation of the acid, e.g., as the acid chloride, as a mixed anhydride with an alkyl chloroformate, or with a dehydrative coupling agent such as dicyclohexylcarbodiimide. A preferred optically active acid in the present case is S-O-acetylmandelic acid. Once the resulting diastereomeric esters are separated, e.g., by chromatographic methods, they are hydrolyzed by conventional methods, e.g., aqueous acid or aqueous base, to obtain the enantiomeric, optically active alcohols.

The prodrug esters of the present invention are prepared by methods similar to those used in the synthesis of esters in the preceding paragraph. Esters with alpha-amino acids, including natural L-amino acids, will generally be prepared from the appropriate amino acid in which the alpha-amino group, substituent $NH_2$ or NH groups (e.g., lysine, ornithine, arginine, histidine, tryptophan), hydroxy groups (serine, homoserine, threonine, tyrosine), mercapto groups (cysteine) and substituent carboxy groups (glutamic acid, aspartic acid) are in protected form (e.g., N-benzyloxycarbonyl, O- and S-benzyl) generally removed by catalytic hydrogenation in a subsequent step. Similarly, in the case of esters with primary or secondary amino substituents, the acids will be coupled with amino groups protected. Such protection is, of course, unnecessary with those acids containing tertiary amino substituents. Finally, the carboxy substituted esters are most conveniently prepared from the cyclic anhydride:

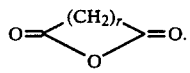

Concerning the biological activity of the present compounds, it is known that arachidonic acid is metabolized in mammals by means of two distinct pathways, one leading to prostaglandins and thromboxanes, the other to several oxidative products called leukotrienes, which are designated by letter number combinations such as B4, C4 and D4. The first step in this oxidative pathway is the oxidation of arachidonic acid under the influence of 5-lipoxygenase enzyme, an enzyme which is generally inhibited by the compounds (I) of the present invention, thus blocking the synthesis of all leukotrienes. That in itself provides the mechanism sufficient for the utility of the present compounds in the treatment or prevention of asthma (where LTC4 and LTD4 are understood to be mediators), arthritis (where LTB4 is understood to be a mediator in inflammation), psoriasis (where LTB4 is understood to be a mediator), ulcers (where LTC4 and LTD4 are understood to be mediators) and myocardial infarction (where LTB4 is understood to be a mediator). Supplementing this enzyme inhibitory activity is the general ability of the present compounds to antagonize leukotriene D4 (i.e., block LTD4 receptors). In general, the present compounds also antagonize leukotriene B4. For a review concerning leukotrienes, see Bailey et al., *Ann. Reports Med. Chem.* 17, pp. 203-217 (1982).

The in vitro activity of the compounds of the formula (I) is tested as follows. RBL-1 cells, maintained in monolayer form are grown for 1 or 2 days in spinner culture in Minimum Essential Medium (Eagle) with Earl's Salts plus 15% Fetal Bovine Serum supplemented with antibiotic/antimycotic solution (GIBCO). The cells are washed 1 time with RPMI 1640 (GIBCO) and resuspended in RPMI 1640 plus 1 microM glutathione to a cell density of $1 \times 10^7$ cells/ml. A volume of 0.5 ml of the cell suspension is incubated at 30° C. with 0.001 ml of dimethylsulfoxide solution of drug for 10 minutes. The reaction is started by a simultaneous addition of 0.005 ml (14C)-arachidonic acid in ethanol and 0.002 ml A23187 in dimethylsulfoxide to give final concentrations of 5.0 and 7.6 microM, respectively. After a 5 minute incubation at 30° C., the reaction is stopped by the addition of 0.27 ml acetonitrile/acetic acid (100/0.3) and the media is clarified by centrifugation. Analysis of the product profile is made by a 0.2 ml injection of the clarified supernatant into HPLC. The separation of radioactive products is effected on a radial PAX CN column (5 mm I.D., Waters) with a solvent system of acetonitrile/H2O/acetic acid (0.1%) with a linear acetonitrile gradient from 35% to 70% over 15 minutes at 1 ml/minute. Quantitation is accomplished with a Berthold Radioactivity Monitor equipped with a built-in integrator and a 0.2 ml flow cell mixing 2.4 ml/minute Omnifluor (NEN) with column effluent. Integration units for each product are calculated as a percentage of total integration units, and then compared to the average control levels. The results are expressed as "Percent of Control" and are plotted vs the log of drug concentration. The IC$_{50}$ values are estimated by graphical inspection.

The leukotriene D4 (LTD4) receptor assay tests the ability of a compound to compete with radiolabelled LTD4 for specific LTD4 receptor sites on guinea pig lung membranes. In this test, normal 3-4 week-old guinea pigs are acclimatized under standard conditions for 3 days prior to being sacrificed. Final animal age: 24-31 days. The guinea pigs are stunned by a blow to the back of the neck, and exsanguinated by cutting the carotid artery. The chest cavity is opened and the lungs are removed, rinsed in 50 mM Tris buffer (pH 7.0) and placed in clean buffer. In this and all subsequent operations, all tissue and buffer are kept on ice throughout the preparation, and all centrifugation is carried out at 4° C. Bronchi and connective tissue are trimmed from the lungs. The tissue is weighed and placed in 50 ml polycarbonate tubes with buffer at a ratio of 1 gm tissue/3 ml buffer. The tissue is homogenized by a Tekmar Tissumizer at full speed for 30 seconds and centrifuged in a Sovall SS-34 rotor at 3250 rpm $\times$ 15 minutes. The supernatant is centrifuged at 19,000 rpm $\times$ 10 minutes. The resulting pellet is resuspended in buffer with the Tissumizer at medium speed (position 75) for 10 seconds. The resuspension is again centrifuged at 19,000 rpm $\times$ 10 minutes. The resulting pellet is resuspended by the Tissumizer at slow speed (position 50) for 10 seconds in 1 ml buffer/g of starting tissue. This final suspension is stirred at 4° C. while aliquoted to polypropylene tubes and stored at $-70°$ C. The following are added to a 12$\times$75 mm polystyrene tube:

(1) 25 microL of one of the following:
   A. Dimethylsulfoxide (to determine total binding)
   B. 1 microM LTD4 (to determine non-specific binding)
   C. 30 nanoM-100 microM compound in dimethylsulfoxide (2) 0.025 ml 3H-LTD4 (specific activity 30-60 Ci/mmol) in 50 mM Tris (pH 7.0)+10 microM L-cysteine (12,000-15,000 cpm/0.025 ml)

(3) 0.2 ml diluted membrane preparation (1 mg/ml) (The preparation is diluted in 50 microM Tris buffer+MgCl$_2$ such that in 200 microL protein, a 10 microM MgCl$_2$ concentration is achieved).

The reaction tubes are incubated at 25° C. for 30 minutes. Four ml of cold Tris buffer+10 microM MgCl$_2$ are added to each tube. The contents are quickly filtered through a Whatman GF/C filter with a yeda separation device. The filter is washed 3$\times$ with 4 ml Tris-MgCl$_2$ buffer. The filter is transferred to a scintillation vial. Ultrafluor scintillation fluid is added. The vial is capped, vortexed and counted for 3 hours. Percent specific binding is calculated using the formula:

$$\% \text{ SB} = (X - \text{NSB})/(\text{TB} - \text{NSB}),$$

where
X=cpm sample
NSB=cpm non-specific binding
TB=cpm total binding

Percent specific binding is graphed as a function of compound concentration. IC$_{50}$ is that concentration at which 50% SB occurs. Ki is calculated by using the formula:

$$\text{Ki} = (\text{IC}_{50})/[1 + (\text{L/Kd})],$$

where
L=concentration of ligand added (microM)=cpm added/cpm of 1 microM 3H-LTD4
Kd=1 microM (dissociation constant)

Human polymorphonuclear leukocytes are employed to measure the competition of test molecules with [3H]-LTB4 for binding at the LTB4 receptor. In this test neutrophils are isolated from heparinized human peripheral blood (usually 100 ml) using a Hypaque-Ficoll gradient (density 1.095 g/ml). Hanks balanced salt solution (HBSS) containing 0.1 grams/100 ml bovine serum albumin (HBSS-BSA) is used to resuspend the cells. The one step Hypaque-Ficoll technique yields highly pure populations of neutrophils (greater than 95%). Cell viability is assessed by trypan blue dye exclusion (should be greater than 95%), and the functional integrity of the neutrophils was determined by nitroblue tetrazolium reduction (should be greater than 85% positive). Compounds undergoing test are dissolved in dimethylsulfoxide at a concentration of 100 microM. These solutions are diluted by a factor of 500 using HBSS-BSA. A concentration of 100 microM drug is achieved by introducing the diluted sample in a 0.5 ml aliquot into the reaction tube. Serial dilutions of 1-3 and 1-5 are made (as appropriate) and a 0.5 ml aliquot of these dilutions is added to the incubation tube. [3H]-LTB4 (NEN:specific radioactivity, greater than 180 Ci/mmol; 0.005 ml in absolute ethanol) is introduced into borosilicate tubes (12×75 mm). A volume of 0.5 ml of the drug solution (see above) is then added. The binding reaction is initiated by adding 0.5 ml of ice cold neutrophils at a cell density of [$5 \times 10^6$ cells/ml], and continued at 4° C. for 30 minutes. The incubation is terminated by rapid filtration through a Whatman GF/C glass filter to separate the free from the bound radiolabelled ligand. The filters are washed 3-times with 3 ml ice-cold HBSS, dried, placed in 4 ml of Ultrafluor, and counted. Total binding is defined as the CPM present on the filter (cell associated) when radiolabelled ligand is incubated with neutrophils in the absence of any competing agent. Nonspecific binding is obtained by incubating cells with radiolabelled ligand plus 1 microM nonradiolabelled LTB4. Specific binding is total binding CPM corrected for the nonspecific binding CPM. Every tube is corrected for nonspecific binding. Points of half-maximal displacement of radiolabelled ligand are estimated by graphical analysis on a semi-logarithmic plot of percent of specific binding (no competitor present) vs concentration.

To evaluate the compounds of the formula (I) in vivo, they are tested by the so-called PAF lethality assay procedure:

MATERIALS

Mice:

CD1 males, all approximately the same weight (approximately 26 grams), 12 per group.

Vehicle for oral drug dosing:

EES (5% ethanol, 5% emulphor, 90% saline). Stored at room temperature.

Drugs:

For routine screening at 50 mg/kg, 20 mg drug is dissolved in 4 ml EES, using sonication in a sonicator bath or grinding in a Ten Broeck grinder to dissolve drug if necessary. If solubility is still a problem, the drug is used as a suspension.

Vehicle for i.v. Injection:

Saline with 2.5 mg/ml Bovine Serum Albumin (BSA, Sigma #A4378) and 0.05 mg/ml Propranolol (Sigma #P0884). Prepared fresh daily and kept at room temperature.

Platelet Activating Factor (PAF):

A 10 microM stock solution is prepared by dissolving 1 mg PAF (Calbiochem #429460) in 0.18 ml ethanol. This is stored at −20° C. and is diluted in vehicle (see above) the day of use. The concentration of PAF used is calibrated so that when injected at 0.1 ml/10 grams body weight, it will kill approximately 80% of untreated controls. This is usually about 0.028 g/kg (a 1 to 2034 dilution from stock). The solution is prepared in glass containers and is used with glass syringes to minimize surface adhesion by the PAF. It is kept at room temperature.

Positive Control:

Phenidone is used at 25 mg/kg (its approximate ED 50).

METHOD 45 minutes before PAF injection, mice are treated orally with drug using 0.1 ml/10 grams body weight. 35 to 40 minutes later they are placed under a heat lamp to dilate the caudal vein for PAF in3ection. PAF is injected i.v. at 0.1 ml/10 grams body weight, and death follows usually within 30 minutes, rarely after 60 minutes. Results are expressed as percent mortality as compared to controls. Because the assay appears to be sensitive to endogenous catecholamines (i.e., beta agonists protect the mice), Propranolol is used to overcome this potential problem. It also helps if the mice are acclimated to the room before testing, and if room noise and temperature are kept moderate and constant. The heat lamp distance should be calibrated so as to permit vasodilation without visible stress to the mice. Fasting the mice should be avoided.

VARIATIONS

1. The time for oral dosing can be changed.
2. Intravenous drug dosing is possible by coinjecting the drug with PAF in the same volume and vehicle as described above. For coinjection, PAF is prepared at twice the desired concentration in saline with BSA and Propranolol as above, and the drug is prepared at twice the desired concentration in the same vehicle. The two preparations are mixed in equal volumes immediately before injection.

For use in the prevention or treatment of asthma, arthritis, psoriasis and gastrointestinal ulcers in a mammal, including man, a compound of the formula (I) is given in a 5-lipoxygenase inhibiting and/or leukotriene receptor blocking amount of about 0.5–50 mg/kg/day, in single or divided daily doses. A more preferred dosage range is 2–20 mg/kg/day, although in particular cases, at the discretion of the attending physician, doses outside the broader range may be required. The preferred route of administration is generally oral, but parenteral administration (e.g., intramuscular, intravenous, intradermal) will be preferred in special cases, e.g., where oral absorption is impaired as by disease, or the patient is unable to swallow.

The compounds of the present invention are generally administered in the form of pharmaceutical compositions comprising at least one of the compounds of the formula (I), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; and, for parenteral administration, in the form of injectable solutions or suspensions, and the like.

The present invention is illustrated by the following examples, but is not limited to the details thereof.

EXAMPLE 1

6-Methoxy-3-(3-pyridyl)methylene-4-chromanone

To a 25° C. mixture of 20.0 g (0.112 mol) of 6-methoxy-4-chromanone and 18.09 g (0.169 mol) of 3-pyridinecarbaldehyde in 100 ml of methanol was added 14.1 ml (0.169 mol) of pyrrolidine. The resultant solution was allowed to stir 60 hours at 25° C., cooled to 0° C. and filtered to yield 17.07 g (57%) of the title compound, m.p. 127°-131° C.

MS (m/e) 267 (M+), 238, 161, 150 (100%), 135 and 107. IR (CHCl$_3$) 1671 (C=O), 1614, 1589 and 1566 cm$^{-1}$. $^1$H-NMR(CDCl$_3$)delta(ppm): 3.79 (s, OCH$_3$), 5.23 (d, J=1.5 Hz, CH$_2$), 6.86 (d, J=8 Hz, C-8H), 7.06 (dd, J=8, 2 Hz, C-7H), 7.37 (d, J=1.5 Hz, vinyl H), 7.36, 7.58, 7.75, 8.52 and 8.57 (multiplets, 5ArH).

Analysis calculated for C$_{16}$H$_{13}$NO$_3$: C, 71.90; H, 4.90; N, 5.24%. Found: C, 71.72; H, 4.85; N, 5.16%.

By the same method, methyl 2-formyl-3-thienylcarboxylate (1.42 g, 8.35 mmol) was converted to 2.47 g of 6-methoxy-3-(5-methoxycarbonyl-2-thenylidene)-4-chromanone, m.p. 169°-171° C.

EXAMPLE 2

6-Methoxy-3-(3-pyridylmethyl)-4-chromanone

A mixture of 25.2 g (94.4 mmol) of the title product of the preceding Example and 2 g of 5% Pd/C/50% H$_2$O in 1 liter ethyl acetate was hydrogenated at 35 psig hydrogen for 18 hours. The reaction was filtered through diatomaceous earth with ethyl acetate wash, and the combined filtrate and wash evaporated to an oil. Trituration of this oil with diisopropyl ether gave the title compound as crystals, m.p. 82°-84° C.

MS (m/e) 269 (M+), 252, 177, 150 (100%), 135, 118 and 107. IR (CHCl$_3$) 1685 (C=O), 1618 and 1578 cm$^{-1}$. $^1$H-NMR(CDCl$_3$)delta(ppm): 2.71 (dd, J=15, 10 Hz, 1 CH$_2$Ar), 2.86 (m, CH), 3.19 (dd, J=15, 6 Hz, 1CH$_2$Ar), 3.75 (s, OCH$_3$), 4.07 (dd, J=11, 8 Hz, 1CH$_2$O), 4.30 (dd, J=11, 6 Hz, 1CH$_2$O), 6.82 (d, J=9 Hz, C-8H), 7.03 (dd, J=9, 2 Hz, C-7H), 7.10 (dd, J=7, 7 Hz, C-5 PyrH), 7.27 (d, J=2 Hz, C-5H), 7.53 (d, J=7 Hz, C-4 PyrH) and 8.45 (m, 2 PyrH).

Analysis calculated for C$_{16}$H$_{15}$NO$_3$: C, 71.13; H, 5.57; N, 5.12%. Found C, 71.31; H, 5.58; N, 5.15%.

By the same method, the thenylidene derivative of the preceding Example (2.34 g) was converted to 0.86 g of 6-methoxy-3-(5-methoxycarbonyl-2-thenyl)-4-chromanone; tlc Rf 0.3 (1:19 isopropyl ether:CH$_2$Cl$_2$).

EXAMPLE 3

6-Hydroxy-3-(3-pyridylmethyl)-4-chromanone

A mixture of 13.75 g (51.1 mmol) of the title product of the preceding Example, 46 ml of concentrated hydrobromic acid and 47 ml of acetic acid was heated at reflux for 10 hours, and then stirred 12 hours at 25° C. The reaction was poured into 470 ml of ice and water and the pH adjusted to 7.5-8 with solid sodium bicarbonate. The precipitate formed was stirred 0.5 hours, filtered, washed with water and dried in vacuo to yield 11.79 g (90%) of the title compound, m.p. 163°-166° C.

MS (m/e) 255 (M+, 100%), 241, 163, 136, 120 and 108. IR(KBr) 1687 (C=O), 1625, 1598 and 1582 cm$^{-1}$. $^1$H-NMR(DMSO-d$_6$)delta(ppm): 2.69 (dd, J=11, 17 Hz, $^1$CH$_2$Ar), 3.10 (m, CH and $^1$CH$_2$Ar), 4.11 (dd, J=11, 11 Hz, 1OCH$_2$), 4.27 (dd, J=11, 5 Hz, 1OCH$_2$), 6.85 (d, J=8 Hz, C-8H), 6.98 (dd, J=8, 2 Hz, C-7H), 7.07 (d, J=2 Hz, C-5H), 7.31 (dd, J=9, 8 Hz, C-5 PyrH), 7.67 (d, J=8 Hz, C-4 PyrH), 8.42 (m, 2 PyrH) and 9.48 (s, OH).

Analysis calculated for C$_{15}$H$_{13}$NO$_3$.¼H$_2$O: C, 69.35; H, 5.24; N, 5.39%. Found: C, 69.39; H, 5.08; N, 5.37%.

Using methanol saturated with HCl in place of HBr/acetic acid and a reflux time of 1 hour, the thenyl derivative of the preceding Example (0.94 g) was converted to 0.90 g of 6-hydroxy-3-(5-methoxycarbonyl-2-thenyl)-4-chromanone.

EXAMPLE 4 cis and trans-3-(3-Pyridyl)methylchroman-4,6-diol

To a 0° C. solution of 17.86 g (70.0 mmol) of the title product of the preceding Example in 150 ml tetrahydrofuran and 150 ml methanol was added 7.94 g (0.21 mol) of sodium borohydride in small portions to avoid excessive foaming. The reaction was stirred 18 hours at 0°-25° C. and then the solvents were removed by evaporation in vacuo. The residue was dissolved in 100 ml water and 100 ml 4N hydrochloric acid (cold) and stirred 20 minutes. The resultant solution was basified with solid sodium bicarbonate and the mixture multiply extracted with ethyl acetate. The combined extracts were dried over magnesium sulfate and evaporated to an oil (this material is a monohydrate). Hydration interfers with the next alkylation step, thus the hydrated water was replaced by ethanol via three azeotropic distillations on a rotating evaporator with 100 ml each of ethanol. The resultant oil was dried in vacuo to a foam which by $^1$H-NMR analysis is a 3:5 mixture of trans:cis isomers complexed with 0.3 mol of ethanol.

MS (m/e) 257 (M+), 137, 120 and 101. $^1$H-NMR(DMSO-d$_6$)delta(ppm): 1.02 (t, J=7 Hz, CH$_3$ of EtOH), 2.02 and 2.13 (m, CH), 2.42 (m, 1CH$_2$Ar), 2.72 (m, 1CH$_2$Ar), 3.40 (m, CH$_2$ of EtOH), 3.72 (m, 1CH$_2$O), 3.84 (m, CH$_2$O), 3.97 (m, 1CH$_2$O), 4.17 (after D$_2$O exchange, d, J=4 Hz, trans isomer CHOD), 4.22 (after D$_2$O exchange, d, J=2 Hz, cis isomer CHOD), 4.22 (t, J=6 Hz, OH of EtOH), 5.33 (d, J=6 Hz, OH), 5.42 (d, J=6 Hz, OH), 6.55, 6.70, 7.28, 7.58, 7.67 and 8.28 (m, 7 ArH), 8.77 and 8.81 (s, OH).

EXAMPLE 4A cis-3-(3-Pyridyl)methylchroman-4,6-diol

A mixture of the title product of Example 3 (6.0 g, 0.023 mol) and cerium chloride heptahydrate (CeCl$_3$.7-H$_2$O; 5.25 g, 0.0141 mol) in methanol (125 ml) was cooled to 0°-5° C. and sodium borohydride (0.445 g, 0.0117 mol) was added in three portions. The reaction was stirred at room temperature for 0.5 hours. Methanol was then removed in vacuo and the foamy residue was treated with saturated NH$_4$Cl solution, followed by extraction with ethyl acetate. The organic layer was dried over MgSO$_4$ and concentrated in vacuo to a foam. The foam was treated with toluene and then pumped under high vacuum for several hours. This was repeated two more times to give present title product (5.7 g, 94%). $^1$H-NMR analysis (see preceding Example) indicated about 4% contamination with the trans-isomer.

By the same method, the thenyl product of Example 3 (0.89 g) was converted to 0.75 g of cis-3-(5-methoxycarbonyl-2-thenyl)chroman-4,6-diol, m.p. 144°-147° C.

EXAMPLE 5 cis and trans-3-(3-Pyridylmethyl-6-(2-quinolyl)methoxy-4-chromanol

To a 0° C. solution of 18.3 g (71.2 mmol) of a 3:5 mixture of trans and cis-3-(3-pyridyl)methylchroman-4,6-diol and 13.3 g (75.1 mmol) of 2-(chloromethyl)-quinoline in 75 ml of dry dimethylformamide was added 1.80 g (75.1 mmol) of sodium hydride as a 60% mineral oil suspension. The reaction was stirred 1 hour at 0°-20° C. followed by quenching with the addition of excess saturated ammonium chloride. The quenched reaction was extracted with ethyl acetate and the organic extract washed twice with saturated sodium chloride, dried over sodium sulfate and evaporated to an oil. This crude product was purified via column chromatography on 1 kg of silica gel eluted with 10% isopropanol/10% ethyl acetate/80% dichloromethane to give in order of elution the title cis-isomer, 10.31 g (36%), m.p. 107°-110° C., and crude trans-isomer which was rechromatographed on 750 g of silica gel to yield the title trans-isomer, 4.89 g (17%), m.p. 123°-126° C. after recrystallization from methylene chloride/ether.

cis-isomer. MS (m/e) 398 (M+), 288, 261, 256, 238, 210 and 142 (100%). IR (CHCl$_3$) 3591, 3285 (OH), 1617, 1601 and 1577 cm$^{-1}$. $^1$H-NMR(CDCl$_3$)delta(ppm): 2.22 (m, C-3H), 2.59 (dd, J=12, 6 Hz, 1CH$_2$Ar), 2.87 (dd, J=12, 8 Hz, 1CH$_2$Ar), 4.00 (m, OCH$_2$), 4.40 (d, J=3.37 Hz, CHOH), 5.22 (s, CH$_2$O), 6.73 (d, J=8 Hz, C-8H), 6.82 (d, J=2 Hz, C-5H), 6.85 (dd, J=8, 2 Hz, C-7H), 7.18 (m, ArH), 7.48 (dd, J=8, 8 Hz, ArH), 7.55 (m, 2ArH), 7.66 (dd, J=8, 8 Hz, ArH), 7.75 (d, J=8 Hz, ArH), 7.95 (d, J=8 Hz, ArH), 8.10 (d, J=8 Hz, ArH), 8.40 (m, ArH) and 8.47 (m, ArH).

Analysis calculated for C$_{25}$H$_{22}$N$_2$O$_3$: C, 75.36; H, 5.56; N, 7.03%. Found: C, 75.15; H, 5.55; N, 6.89%.

trans-isomer. MS (m/e) 398 (M+), 288, 261, 256 and 142 (100%). IR (CHCl$_3$) 3583, 3302 (OH), 1618, 1601 and 1577 cm$^{-1}$. $^1$H-NRM(CDCl$_3$)delta(ppm): 2.15 (m, C-3H), 2.48 (dd, J=13, 8 Hz, 1CH$_2$Ar), 2.69 (dd, J=13, 6 Hz, 1CH$_2$Ar), 3.85 (dd, J=12, 6 Hz, 1CH$_2$O), 4.15 (dd, J=12, 3 Hz, 1CH$_2$O), 4.41 (d, J=3.95 Hz, CHOH), 5.27 (s, CH$_2$O), 6.77 (d, J=8 Hz, C-8H), 6.90 (dd, J=8, 2 Hz, C-7H), 7.16 (m, ArH), 7.46 (m, 2ArH), 7.63 (d, J=8 Hz, ArH), 7.69 (m, ArH), 7.79 (d, J=8 Hz, ArH), 8.02 (d, J=8 Hz, ArH), 8.15 (d, J=8 Hz, ArH), 8.36 (m, 2ArH).

Analysis calculated for C$_{25}$H$_{22}$N$_2$O$_3$: C, 75.36; H, 5.56; N, 7.03%. Found: C, 75.15; H, 5.55; N, 6.89%.

EXAMPLE 5A cis-3-(3-Pyridyl)methyl-6-(2-quinolyl)methoxy-4-chromanol

To a solution of 10 g (38.8 mmol) of the title product of Example 4A and 7.02 g (39.5 mmol) of 2-chloromethylquinoline in 70 ml dimethylformamide was added, in one portion, 1.58 g (39.5 mmol) of sodium hydride (60% dispersion in mineral oil). The reaction was stirred for 2 hours at 25° C., quenched with an excess of saturated ammonium chloride, and extracted with ethyl acetate. The organic phase was washed with water and saturated sodium chloride, dried over magnesium sulfate, and evaporated to a foam, which was crystallized and recrystallized from chloroform-diisopropyl ether to yield 11.1 g (72%) of present title product, identical with cis-product of the preceding Example.

Likewise 4-methoxy-2-picolyl chloride (0.266 g, 1.7 mmol) was converted to cis-6-(4-methoxy-2-picolyl)methoxy-3-(3-pyridylmethyl)-4-chromanol.

EXAMPLE 6

3S,4S- and 3R,4R-3-(3-Pyridyl)methyl-6-(2-quinolyl)methoxy-4-chromanyl R-O-Acetylmandelate To a 0° C. solution of 4.00 g (10.1 mmol) of the title cis-isomer of the preceding two Examples, 2.30 g (11.8 mmol) of (R)-(−)-O-acetylmandelic acid and 1.44 g (11.8 mmol) of 4-N,N-dimethylaminopyridine in 20 ml dichloromethane was added 2.27 g (11.0 mmol) dicyclohexylcarbodiimide. The reaction mixture was stirred 16 hours while warming to 25° C. The reaction was filtered and the filtrate evaporated to an oil. Column chromatography of this crude product on 600 g silica gel eluted with 3% isopropanol-5% ethyl acetate-92% dichloromethane gave in order of elution 1.78 g (31%) of 3S-,4S-title diastereomer and 2.08 g (36%) of 3R-,4R-title diastereomer as oils.

3S,4S-isomer: MS (m/e) 574 (M+), 397, 381, 288, 238, 149, 147 and 142 (100%). IR(CHCl$_3$) 1745 (C=O), 1619, 1600 and 1578 cm$^{-1}$. $^1$H-NMR(CDCl$_3$)delta(ppm): 1.91 (dd, J=15, 10 Hz, 1CH$_2$Ar), 2.2 (1CH$_2$Ar overlap with 2.23), 2.23 (s, Ac), 2.35 (m, C-3H), 3.87 (m, OCH$_2$), 5.29 (s, CH$_2$O), 5.93 (d, J=3 Hz, C-4H), 5.98 (s, mandelate CH), 6.76 (d, J=9 Hz, C-8H), 6.96 (m, C-5, 7H) and 7.1-8.5 (9m, 15 ArH).

3R,4R-isomer: MS (m/e) 574 (M+), 397, 381, 288 (100%), 261, 238, 147 and 142. IR(CHCl$_3$) 1742 (C=O), 1619, 1601 and 1577 cm$^{-1}$. $^1$H-NMR(CDCl$_3$)delta(ppm): 2.22 (s, Ac), 2.48 (m, C-3H), 2.57 (dd, J=14, 9 Hz, 1CH$_2$Ar), 2.83 (dd, J=14, 6 Hz, 1CH$_2$Ar), 3.98 (m, OCH$_2$), 5.08 (m, CH$_2$O), 5.99 (s, mandelate CH), 5.93 (d, J=3 Hz, C-4H), 6.59 (s, J=3 Hz, C-5H), 6.69 (d, J=9 Hz, C-8H), 6.84 (dd, J=9, 3 Hz, C-7H) and 7.1-8.5 (8m, 15 ArH).

The structure and absolute stereochemistry of these isomers was proven by X-ray crystallographic analyses. For this purpose, the 3S,4S-isomer was recrystallized from methanol, m.p. 135°-136° C. [alpha]$_D^{20}$= −7.78° (tetrahydrofuran, c=0.0465).

Analysis calculated for C$_{35}$H$_{30}$N$_2$O$_6$: C, 73.15; H, 5.26; N, 4.88%. Found: C, 72.88; H, 4.89; N, 5.00%

For the same purpose, the 3R,4R-isomer was recrystallized from CHCl$_3$/hexane, m.p. 126.5°-128° C. [alpha]$_D^{20}$ = +50.65° (tetrahydrofuran, c=0.034).

Analysis calculated for C$_{35}$H$_{30}$N$_2$O$_6$.$\frac{1}{4}$H$_2$O: C, 72.59; H, 5.31; N, 4.84%. Found: C, 72.39; H, 5.30; N, 4.80%

EXAMPLE 7

3S-(3-Pyridyl)methyl-6-(2-quinolyl)methoxy-4S-chromanol

The 3S,4S-title diastereomeric ester of the preceding Example, 1.78 g (3.10 mmol) and 4.92 g (35.7 mmol) of potassium carbonate in a mixture of 38 ml methanol, 38 ml tetrahydrofuran and 10 ml water was stirred 16 hours at 25° C. The organic solvent was removed on a rotating evaporator and the residue dissolved in 500 ml water and 150 ml dichloromethane. The organic layer along with three 100 ml extracts of the aqueous layer was dried over magnesium sulfate and evaporated to an oil. This crude product was crystallized from diisopropyl ether/dichloromethane to yield 1.06 g (88%) of the title compound, m.p. 137°-138° C., [alpha]$_D^{20}$ = −98.40° (CH$_3$OH, c=0.01045).

MS (m/e) 398 (M+ 100%), 288, 263, 256, 238 and 142.
IR (CHCl$_3$) 3589, 3244 (OH), 1618, 1600 and 1577 cm$^{-1}$. $^1$H-NMR(CDCl$_3$)delta(ppm): 2.24 (m, C-3H), 2.16 (dd, J=14, 8 Hz, 1CH$_2$Ar), 2.89 (dd, J-14, 8 Hz, 1CH$_2$Ar), 4.02 (m, OCH$_2$), 4.41 (d, J=3 Hz, C-4H), 5.22 (s, CH$_2$O), 6.75 (d, J=8 Hz, C-8H), 6.83 (d, J=2 Hz, C-5H), 6.86 (dd, J=8, 2 Hz, C-7H), 7.2 (m, 1ArH), 7.49 (m, 1ArH), 7.57 (m, 2ArH), 6.67 (ddd, J=8, 8, 2 Hz, 1ArH), 7.77 (d, J=8 Hz, 1ArH), 7.98 (d, J=8 Hz, 1ArH), 8.11 (d, J=8 Hz, 1ArH), 8.42 (m, 1ArH) and 8.49 (d, J=2 Hz, 1ArH).

Analysis calculated for C$_{25}$H$_{22}$N$_2$O$_3$: C, 75.36; H, 5.56; N, 7.03%. Found: C, 75.06; H, 5.36; N, 7.00%.

EXAMPLE 8

3R-(3-Pyridyl)methyl-6-(2-quinolyl)methoxy-4R-chromanol

By the procedure of the preceding Example, the title 3R,4R-diastereomeric ester of Example 6, 2.08 g (3.62 mmol) was converted to present title product, 1.15 g (80%), crystallized from diisopropyl ether/dichloromethane, m.p. 137°–138° C., [alpha]$_D^{20}$ = +98.40° (CH$_3$OH, c=0.00985).

MS (m/e) 398 (M+), 288, 261, 256, 238 and 142 (100%). IR(CHCl$_3$) 3588, 3285 (OH), 1619, 1600 and 1577 cm$^{-1}$. $^1$H-NMR(CDCl$_3$)delta(ppm): 2.24 (m, C-3H), 2.61 (dd, J=14, 8, 1CH$_2$Ar), 2.89 (dd, J=14, 8 Hz, 1CH$_2$Ar), 4.02 (m, OCH$_2$), 4.41 (d, J-3 Hz, C-4H), 5.22 (s, CH$_2$O), 6.75 (d, J=8 Hz, C-8H), 6.83 (d, J=2 Hz, C-5H), 6.86 (dd, J=8, 2 Hz, C-7H), 7.2 (m, 1 ArH), 7.49 (m, 1ArH), 7.57 (m, 2 ArH), 6.67 (ddd, J=8, 8, 2 Hz, 1ArH), 7.77 (d, J=8 Hz, 1ArH), 7.98 (d, J=8 Hz, 1ArH), 8.11 (d, J=8 Hz, 1ArH), 8.42 (m, 1ArH) and 8.49 (d, J=2 Hz, 1ArH).

Analysis calculated for C$_{25}$H$_{22}$N$_2$O$_3$: C, 75.36; H, 5.56; N, 7.03%. Found: C, 75.19; H, 5.38; N, 6.97%.

EXAMPLE 9

6-Benzyloxy-3-phenoxy-4-chromanone

A solution of 17 g of 3-diazo-6-benzyloxy-4-chromanone and 17 g of phenol in 100 ml of toluene was heated to 110° C. in an oil bath. Rhodium (II) acetate dimer (50 mg) was added in one portion. After nitrogen evolution ceased (5 minutes), the reaction was allowed to cool to room temperature, diluted with ethyl acetate and washed with 10% sodium hydroxide to remove excess phenol. The organic layer was dried over sodium sulfate and evaporated in vacuo to give the crude product, which was purified by column chromatography on silica gel eluting with dichloromethane to give 2.6 g of product, m p. 100°–102° C. $^1$H-NMR(CDCl$_3$)delta(ppm): 4.4 (m, 2H), 4.84 (m, 1H), 4.88 (s, 2H), 6.82-7.40 (m, 13H).

EXAMPLE 10

6-Hydroxy-3-phenoxy-4-chromanone

A mixture of 2.76 g of the title product of the preceding Example, 60 ml of ethyl acetate and 850 mg of 10% Pd/C catalyst was hydrogenated at 44 psig for 4 hours. The catalyst was removed by filtration and the filtrate evaporated in vacuo to give title product as a yellow solid, m.p. 142°–146° C.

MS (m/e) calculated for C$_{15}$H$_{12}$O$_4$: 256.0736; found: 256.0713. $^1$H-NMR(acetone-d$_6$)delta(ppm): 4.6 (m, 2H), 4.15 (dd, 1H), 6.8–7.3 (m, 8H).

EXAMPLE 11 cis- and trans-3-Phenoxychroman-4,6-diol

To a solution of 1.86 g of the title product of the preceding Example in 50 ml of tetrahydrofuran was added 550 mg of lithium aluminum hydride. The reaction was stirred for 2 hours, then quenched with water, acidified to pH 4 with dilute hydrochloric acid and extracted with ethyl acetate. The ethyl acetate layer was dried over sodium sulfate and evaporated in vacuo to give the crude product mixture which was triturated with CH$_2$Cl$_2$ and filtered to yield pure cis-title product, 650 mg, m.p. 207°–208° C. The filtrate was evaporated in vacuo and separated by column chromatography on silica gel eluting with chloroform/ether. A total of 800 mg of less polar cis and 450 mg of more polar trans product (m.p. 144°–146° C.) were obtained.

cis-isomer: MS (m/e) 258 (M+). $^1$H-NMR(acetone-d$_6$) delta(ppm): 4.00–4.18 (m, 2H), 4.75 (m, 1H), 4.95 (m, 1H), 6.5–7.40 (m, 8H).

trans-isomer: $^1$H-NMR(acetone-d$_6$)delta(ppm): 4.25 (s, 2H), 4.5–4.7 (m, 2H), 6.55–7.3 (m, 8H).

EXAMPLE 12 cis-3-Phenoxychroman-4,6-diol

A mixture of 10.04 g of the title product of Example 9, 200 ml of methanol, 100 ml of tetrahydrofuran and 1 g 10% Pd/C catalyst was hydrogenated at 44 psig for 24 hours. The catalyst was recovered by filtration and the filtrate was evaporated in vacuo to obtain the crude product, which was triturated with dichloromethane and filtered to give 4.9 g of title product having properties identical to those of the cis-title product of the preceding Example.

EXAMPLE 13

(±)-cis-3-Phenoxy-6-(2-quinolyl)methoxy-4-chromanol

To a solution of 800 mg of the title product of the preceding Example and 835 mg of 2-chloromethylquinoline in 55 ml of dimethylformamide was added 299 mg of 50% NaH. The reaction was allowed to stir at room temperature for 3 hours, then poured into water and extracted with ethyl acetate. The ethyl acetate layer was dried over sodium sulfate and evaporated in vacuo to give the crude product, which was purified by trituration with ether to yield 455 mg of title product, m.p. 151°–153° C. $^1$H-NMR(DMSO-d$_6$)delta(ppm): 4.1–4.3 (m, 2H), 4.75 (s, 1H), 4.85 (s, 1H), 5.30 (s, 2H), 5.55 (d, J=1, 1H), 6.65–8.0 (m, 14H), 8.40 (d, J=1, 1H).

Substituting equivalent 2-chloromethyl-1-methylbenzimidazole for 2-chloromethylquinoline, title product of the preceding Example (256 mg) was converted to 210 mg of cis-3-phenoxy-6-(1-methyl-2-benzimidazolyl)methoxy-4-chromanol, m.p. 185°–186° C.

EXAMPLE 14

(±)-trans-3-Phenoxy-6-(2-quinolyl)methoxy-4-chromanol

To a solution of 450 mg of the trans-title product of Example 11 and 461 mg of 2-chloromethylquinoline in 30 ml of dimethylformamide was added 168 mg of 50% sodium hydride. The reaction was allowed to stir at room temperature for 3 hours, then poured into water and extracted with ethyl acetate. The ethyl acetate layer was dried over sodium sulfate and evaporated in vacuo to give the crude product, which was purified by column chromatography on silica gel eluting with dichloromethane and recrystallization from CH$_2$Cl$_2$/isopropyl ether to give 160 mg of title product, m.p. 127° C.

EXAMPLE 15

($\pm$)-cis-6-(5-Fluoro-2-benzothiazolyl)methoxy-3-phenoxy-4-chromanol

A mixture of 256 mg of cis-title product of Example 11, 221 mg of 2-chloromethyl-6-fluorobenzothiazole, 415 mg of potassium carbonate, 165 mg of sodium iodide and 25 ml of acetone was heated at reflux overnight. The reaction was cooled to room temperature and the inorganics were removed by filtration. The filtrate was evaporated to afford the crude product, which was purified by column chromatography on silica gel eluting with CH$_2$Cl$_2$/ether and trituration with ether to give 150 mg of product, m.p. 144°-145° C. MS calculated for C$_{23}$H$_{18}$NFS: 423.0940; found 423.0914. $^1$H-NMR(acetone-d$_6$)delta(ppm): 4.2-4.45 (m, 2H), 4.85 (s, 1H), 5.05 (s, 1H), 5.5 (s, 2H), 6.7-7.4 (m, 7H), 7.75 (d, J=2, 1H), 8.05 (m, 1H).

EXAMPLE 16

3S-,4R- and 3R,4S-3-Phenoxy-6-(2-quinolyl)methoxy-4-chromanyl R-O-Acetylmandelate To a solution of 1.96 g of the title product of Example 13, 710 mg of dimethylaminopyridine and 1.13 g of (R)-(−)-O-acetylmandelic acid in 125 ml of dichloromethane was added 1.2 g of dicyclohexylcarbodiimide. The reaction was allowed to stir at room temperature overnight. The precipitated dicyclohexyl urea was removed by filtration and the filtrate evaporated in vacuo to afford the product mixture. It was separated by column chromatography on silica gel eluting with dichloromethane/isopropyl ether. The less polar product was collected and recrystallized from ethyl acetate/hexane to give 610 mg product, m.p. 92°-94° C. The more polar product was collected and recrystallized from ether/hexane to give 577 mg of product, m.p. 107°-108° C.

One of these diastereomeric cis-compounds possesses title 3S,4R-chromanyl stereochemistry and the other 3R,4S-chromanyl stereochemistry. Although their absolute stereochemistry has not yet been independently determined, based upon its polarity and optical rotation, it is believed that the less polar isomer is the 3S,4R-diastereoisomer.

EXAMPLE 17

(−)-3S*-Phenoxy-6-(2-quinolyl)methoxy-4R*-chromanol

A mixture of 610 mg of the less polar ester of the preceding Example, 1.7 g of potassium carbonate, 4 ml water, 13 ml methanol and 13 ml of tetrahydrofuran was stirred at room temperature overnight. Excess potassium carbonate was removed by filtration and the filtrate was evaporated in vacuo to afford the crude product, which was purified by dissolution in ethyl acetate and washing with water. The ethyl acetate layer was dried and evaporated to give 400 mg of title product, m.p. 155°-157° C. [alpha]$_D$=−21.6° (c=0.005, tetrahydrofuran).

The absolute stereochemistry of this cis-product is believed to be 3S-,4R.

EXAMPLE 18

(+)-3R*-Phenoxy-6-(2-quinolyl)methoxy-4S*-chromanol

A mixture of 577 mg of the more polar mandelate ester of Example 16, 1.6 g of potassium carbonate, 4 ml of water, 13 ml of tetrahydrofuran and 13 ml of methanol was stirred at room temperature overnight. Excess potassium carbonate was removed by filtration and the filtrate evaporated in vacuo. The residue was dissolved in ethyl acetate and washed with water. The ethyl acetate layer was dried and evaporated to give 300 mg of product, m.p. 159°-160° C. [alpha]$_D$=+19.6° (c=0.005, tetrahydrofuran). The absolute stereochemistry of this cis-product is believed to be 3R,4S.

By the methods of Examples 16-18, the title product of Example 14 was likewise resolved to yield (+)-trans-3-phenoxy-6-(2-quinolyl)methoxy-4-chromanol, m.p. 159°-160° C., [alpha]$_2^{20}$=+19.6° (tetrahydrofuran) and the corresponding (−)-isomer, m.p. 159.5°-160° C., [alpha]$_D^{20}$=−21.6° (tetrahydrofuran).

EXAMPLE 19

6-Benzyloxy-3-(4-methoxyphenoxy)-4-chromanone

Replacing the phenol with a molar equivalent of 4-methoxyphenol, the method of Example 9 was employed to convert 3-diazo-6-benzyloxy-4-chromanone (22 g) to present title product, 6.8 g, m.p. 98°-100° C.

EXAMPLE 20

($\pm$)-cis-3-(4-Methoxyphenoxy)-4,6-chromandiol

By the method of Example 12, the product of the preceding Example (6.8 g) was converted to present title product, 2.7 g, m.p. 187°-189° C. $^1$H-NMR(DMSO-d$_6$) delta(ppm): 3.70 (s, 3H), 4.05-4.30 (m, 2H), 4.55 (s, 1H), 4.80 (s, 1H), 6.50-7.10 (m, 7H).

EXAMPLE 21

($\pm$)-cis-3-(4-Methoxyphenoxy)-6-(2-quinolyl)methoxy-4-chromanol

By the method of Example 13, the product of the preceding Example (2.7 g) was converted to present title product 1.1 g, m.p. 131°-132° C. $^1$H-NMR(DMSO-d$_6$)delta(ppm): 3.65 (s, 3H), 4.05-4.3 (m, 2H), 4.55 (s, 1H), 4.85 (s, 1H), 5.30 (s, 2H), 5.55 (d, J=1, 1H), 6.70-8.4 (m, 13H).

EXAMPLE 22

($\pm$)-cis-6-(5-Fluoro-2-benzothiazolyl)methoxy-3-(4-methoxyphenoxy)-4-chromanol By the method of Example 15, title product of Example 20 (0.70 g) was converted to present title product, 0.11 g, m.p. 180°-181° C. MS (m/e) calculated for C$_{24}$H$_{20}$NO$_5$FS: 453.1047; found: 453.1043.

EXAMPLE 23

(+)- and (−)-cis-3-(4-Methoxyphenoxy)-6-(2-quinolyl)methoxy-4-chromanol

By the methods of Examples 16, 17 and 18, the title product of Example 21 (3.55 g) was resolved into title products:

(+)-isomer, 0.29 g, m.p. 152°–154° C., [alpha]$_D$= +40.0° (c=0.005, CH$_2$Cl$_2$); believed to be the 3S,4R-isomer.

(−)-isomer, 0.40 g, m.p. 152°–154° C., [alpha]$_D$= −42.9° (c=0.005, CH$_2$Cl$_2$); believed to be the 3R,4S-isomer.

EXAMPLE 24

6-Benzyloxy-3-(3-methoxyphenoxy)-4-chromanone

Replacing the phenol with a molar equivalent of 3-methoxyphenol, the method of Example 9 was employed to convert 3-diazo-6-benzyloxy-4-chromanone (76 g) to present title product, 5.5 g, m.p. 98°–100° C.
$^1$H-NMR(CDCl$_3$)delta(ppm): 3.85 (s, 3H), 4.45–4.65 (m, 2H), 5.0–5.2 (m, 3H), 6.5–7.6 (m, 12H).

EXAMPLE 25

(±)-cis-3-(3-Methoxyphenoxy)-4,6-chromandiol

By the method of Example 12, the product of the preceding Example (5.5 g) was converted to present title product, 2.3 g, m.p. 187°–189° C.

MS (m/e) calculated for C$_{16}$H$_{16}$O$_5$: 288.0998; found: 288.0989.

EXAMPLE 26

(±)-cis-3-(3-Methoxyphenoxy)-6-(2-quinolyl)methoxy-4-chromanol

By the method of Example 13, the product of the preceding Example (2.26 g) was converted to present title product, 3.5 g, m.p. 128°–129° C.

EXAMPLE 27

7-Benzyloxy-3,4-dihydro-4-phenoxy-1-benzoxepin-5(2H)-one

To a solution of 1.4 g of phenol in 50 ml of tetrahydrofuran was added 720 mg of 50% sodium hydride. After stirring for 30 minutes, a solution of 4.5 g of crude 7-benzyloxy-4-bromo-3,4-dihydro-1-benzoxepin-5(2H)-one was added. The reaction was allowed to stir at room temperature for 5 hours. The tetrahydrofuran was evaporated in vacuo, and the residue dissolved in ethyl acetate and washed with water. The ethyl acetate layer was dried over sodium sulfate and evaporated in vacuo to give the crude product which was purified by recrystallization from methanol to give 2 g of title product, m.p. 112°–114° C.

MS (m/e) calculated for C$_{28}$H$_{20}$O$_4$: 360.1361; found: 360.1401.

EXAMPLE 28

3,4-Dihydro-7-hydroxy-4-phenoxy-1-benzoxepin-5(2H)-one

A mixture of 2 g of the product of the preceding Example, 200 mg of 10% Pd/C and 50 ml of methanol was hydrogenated in a Parr shaker at 50 psig for 2.5 hours. The catalyst was removed by filtration and the filtrate evaporated in vacuo to give 1.5 g crude product which was used without purification in the next step.

EXAMPLE 29 cis and trans-2,3,4,5-Tetrahydro-4-phenoxy-1-benzoxepin-5,7-diol

To a solution of 3.5 g of the product of the preceding Example in 100 ml of tetrahydrofuran was added 1 g of lithium aluminum hydride. The reaction was allowed to stir at room temperature for 15 minutes, then quenched with water, acidified to pH 4 with dilute hydrochloric acid and extracted with ethyl acetate. The ethyl acetate layer was dried over sodium sulfate and evaporated in vacuo to give the product mixture. It was separated by column chromatography on silica gel eluting with dichloromethane/ether, yielding 0.9 g of less polar trans-title product and 1.2 g of more polar cis-title product, both as oils.

EXAMPLE 30

(±)-trans-2,3,4,5,-Tetrahydro-4-phenoxy-7-(2-quinolyl)methoxy-1-benzoxepin-5-ol

To a solution of 840 mg of the trans-title product of the preceding Example in 25 ml of dimethylformamide was added 154 mg of 50% NaH. After stirring for 20 minutes, 570 mg of 2-chloromethylquinoline was added. The reaction was stirred at room temperature for 1 hour, poured into water and extracted with ethyl acetate. The ethyl acetate layer was dried over sodium sulfate and evaporated in vacuo to afford the crude product. It was purified by recrystallization from dichloromethane/isopropyl ether to give 820 mg of product, m.p. 128°–129° C

EXAMPLE 31

(±)-cis-2,3,4,5,-Tetrahydro-4-phenoxy-7-(2-quinolyl)methoxy-1-benzoxepin-5-ol

To a solution of 950 mg of the cis-title product of Example 29 in 25 ml of dimethylformamide was added 173 mg of 50% sodium hydride. After stirring for 20 minutes, 641 mg of 2-chloromethylquinoline was added. The reaction was stirred at room temperature for 1 hour, poured into water and extracted with ethyl acetate. The ethyl acetate layer was dried over sodium sulfate and evaporated in vacuo to afford the crude product which was purified by recrystallization from methyl acetate/hexane to afford 200 mg of title product, m.p. 130°–132° C.

EXAMPLE 32

7-Benzyloxy-2,3-dihydro-4-(3-pyridyloxy)-1-benzoxepin-5(2H)-one

By the method of Example 27, substituting the phenol with a molar equivalent of 3-hydroxypyridine, 7-benzyloxy-4-bromo-3,4-dihydro-1-benzoxepin-5(2H)-one (4.1 g) was converted to present title product, 2.6 g, m.p. 140°–141° C.

MS (m/e) calculated for C$_{22}$H$_{19}$NO$_4$: 361.1392; found: 361.1396.

EXAMPLE 33

2,3-Dihydro-7-hydroxy-4-(3-pyridyloxy)-1-benzoxepin-5(2H)-one

By the method of Example 28, the title product of the preceding Example (3.3 g) was converted to present title product, 2.5 g, m.p. 182°–185° C.

EXAMPLE 34 cis- and trans-2,3,4,5-Tetrahydro-4-(3-pyridyloxy)-1-benzoxepin-5,7-diol

By the method of Example 29, the product of the preceding Example (2.5 g) was converted to present title products.

cis-isomer, 1.1 g, more polar. $^1$H-NMR(acetone-d$_6$)delta(ppm): 2.2–2.4 (m, 2H), 3.90–4.15 (m, 2H), 4.90 (t, J=4, 1H), 5.20 (s, 1H), trans-isomer, 0.84 g, m.p. 154°–155° C., less polar.

EXAMPLE 35

($\pm$)-trans-2,3,4,5-Tetrahydro-4-(3-pyridyloxy)-7-(2-quinolyl)methoxy-1-benzoxepin-5-ol By the method of Example 30, the trans-title product of the preceding Example (0.80 g) was converted to present title product, 0.23 g, m.p. 134°–136° C.

MS (m/e) calculated for C$_{25}$H$_2$N$_2$O$_4$: 414.1579; found: 414.1635.

EXAMPLE 36

($\pm$)-cis-2,3,4,5-Tetrahydro-4-(3-pyridyloxy)-7-(2-quinolyl)methoxy-1-benzoxepin-5-ol By the method of Example 31, the cis-title product of Example 34 (1.1 g) was converted to present title product, 0.35 g. $^1$H-NMR(DMSO-d$_6$)delta(ppm): 2.40 (m, 2H), 3.80 (m, 1H), 4.10 (m, 1H), 4.85 (s, 1H), 5.0 (d, 1H), 5.35 (s, 2H), 5.80 (d, 1H), 6.9–8.5 (m, 13H).

EXAMPLE 37

7-Benzyloxy-3,4-dihydro-4-(3-(methoxycarbonyl)phenoxy)-1-benzoxepin-5(2H)-one

By the method of Example 27, substituting the phenol with a molar equivalent of methyl 3-hydroxybenzoate, 7-benzyloxy-4-bromo-3,4-dihydro-1-benzoxepin-(5(2H)-one (17.3 g) was converted to present title product, 10.9 g, m.p. 134°–136° C.

MS (m/e) calculated for C$_{22}$H$_{19}$NO$_4$: 361.1392; found: 361.1396. $^1$H-NMR(CDCl$_3$)delta(ppm): 2.40 (m, 1H), 2.95 (m, 1H), 3.95 (s, 3H), 4.0 (m, 1H), 4.6 (m, 1H), 5.05 (s, 2H), 5.30 (t, J=4, 1H), 6.9–7.7 (m, 12H).

EXAMPLE 38

3,4-Dihydro-7-hydroxy-4-(3-(methoxycarbonyl)phenoxy)-1-benzoxepin-5(2H)-one

By the method of Example 28, the title product of the preceding Example (10.9 g) was converted to present title product, 6.3 g.

EXAMPLE 39 cis- and trans-2,3,4,5-Tetrahydro-4-(3-methoxycarbonyl)phenoxy)-1-benzoxepin-5,7-diol To a solution of 4.7 g of the title product of the preceding Example in 100 ml of methanol was added 550 mg of sodium borohydride. The reaction was stirred at room temperature for 1 hour, then quenched with water. The solvent was evaporated in vacuo and the residue dissolved in ethyl acetate and washed with water. The ethyl acetate layer was dried over sodium sulfate and evaporated in vacuo to afford the crude product mixture. It was separated by column chromatography on silica gel, eluting with dichloromethane/ether, yielding 1.14 g of the less polar trans-title product and 1.3 g of the more polar cis-title product.

cis-isomer. $^1$H-NMR(CDCl$_3$)delta(ppm): 2.1 (m, 1H), 2.4 (m, 1H), 3.8 (s, 3H), 3.8–4.1 (m, 2H), 4.61 (s, 1H), 4.90 (s, 1H), 6.5–7.6 (m, 7H).

trans-isomer. $^1$H-NMR(CDCl$_3$)delta(ppm): 2.1 (m, 1H), 2.3 (m, 1H), 3.7 (t, 3H), 3.85 (s, 3H), 4.15 (m, 1H), 4.35 (m, 1H), 4.90 (m, 1H), 6.6–7.6 (m, 7H).

EXAMPLE 40

($\pm$)-trans-2,3,4,5-Tetrahydro-4-(3-methoxycarbonyl)-phenoxy-7-(2-quinolyl)methoxy-1-benzoxepin-5-ol By the method of Example 30, the title product of the preceding Example (1.1 g) was converted to present title product, 1.3 g, tlc (ether) Rf 0.65.

EXAMPLE 41

($\pm$)-cis-2,3,4,5-Tetrahydro-4-(3-methoxycarbonyl)-phenoxy-7-(2-quinolyl)methoxy-1-benzoxepin-5-ol By the method of Example 31, the cis-title product of Example 39 (1.3 g) was converted to present title product, 0.6 g. $^1$H-NMR(DMSO-d$_6$)delta(ppm): 2.25 (m, 2H), 3.80 (s, 3H), 3.85 (m, 1H), 4.05 (m, 1H), 4.85 (m, 1H), 5.1 (s, 1H), 5.3 (s, 2H), 6.85–8.3 (m, 13H).

EXAMPLE 42

($\pm$)-cis-2,3,4,5-Tetrahydro-4-(3-carboxyphenoxy)-7-(2-quinolyl)methoxy-1-benzoxepin-5-ol To a solution of 630 mg of the title product of the preceding Example in 100 ml methanol and 25 ml tetrahydrofuran was added 10 ml of 5N NaOH. The reaction was heated on a steam bath for 10 minutes. The volatiles were evaporated in vacuo, and the residue dissolved in water and acidified to pH 5 with dilute HCl. The precipitated product was collected by filtration and allowed to air-dry, 0.21 g, m.p. 110°–116° C. (dec.).

MS (m/e) calculated for C$_{27}$H$_{23}$NO$_6$: 457.1525; found: 457.1541.

EXAMPLE 43

($\pm$)-trans-2,3,4,5-Tetrahydro-4-(3-carboxyphenoxy)-7-(2-quinolyl)methoxy-1-benzoxepin-5-ol To a solution of 1.3 g of the title product of Example 40 in 100 ml methanol and 25 ml tetrahydrofuran was added 10 ml of 5N NaOH. The reaction was heated on a steam bath for 10 minutes. The volatiles were evaporated in vacuo and the residue dissolved in water and acidified to pH 5. The precipitated title product was collected by filtration and purified by trituration with isopropyl ether, 0.13 g, m.p. 186°–188° C.

MS (m/e) calculated for C$_{27}$H$_{23}$NO$_6$: 457.1525; found: 457.1576.

EXAMPLE 44

6-Benzyloxy-3-(3-(methoxycarbonyl)benzylidene)-4-chromanone

A mixture of 17 g of 6-benzyloxy-4-chromanone, 11.3 g of 3-carbomethoxybenzaldehyde, 14.4 g of pyrrolidine, 100 ml of tetrahydrofuran and 300 ml of methanol was stirred at room temperature overnight. The volatiles were evaporated in vacuo to afford the crude product, which was purified by column chromatography on silica gel eluting with dichloromethane. The product fractions were combined and concentrated to an oil which crystallized upon trituration with methanol to give 17.2 g of title product, m.p. 109°–112° C.

EXAMPLE 45

6-Hydroxy-3-(3-(methoxycarbonyl)benzyl)-4-chromanone

A mixture of 17 g of the product of the preceding Example, 1.7 g of 10% Pd/C catalyst, 200 ml of tetrahydrofuran and 200 ml of methanol was hydrogenated in a Parr shaker at 40 psig for 3 hours. The catalyst was removed by filtration and the volatiles were evaporated in vacuo to give 10.6 g of title product. $^1$H-NMR(acetone-d$_6$)delta(ppm): 2.65–3.30 (m, 3H), 3.80 (s 3H) 4.2 (dd J=4 J=8 2H). 6.80–8.30 (m, 7H).

EXAMPLE 46 cis- and trans-3-(3-(Methoxycarbonyl)benzyl)chroman-4,6-diol

By the methods of Example 39, the product of the preceding Example was converted to present chromatographed title products in about the same yields. This cis-isomer, m.p. 135°–137° C., is less polar and the trans-isomer, m.p. 158°–160° C., is more polar; tlc (7:3 CH$_2$Cl$_2$:ether) Rf 0.25 and 0.20, respectively.

EXAMPLE 47

(±)-cis-3-(3-(Methoxycarbonyl)benzyl)-6-(2-quinolyl)-methoxy-4-chromanol

By the method of Example 30, the cis-title product of the preceding Example was converted to present title product in about the same yield.

Likewise, the thenyl derivative of Example 4A (0.38 g) and 5-fluoro-2-chloromethylbenzthiazole (0.24 g) were converted to cis-6-(5-fluoro-2-benzthiazolyl)methoxy-3-(5-methoxycarbonyl-2-thenyl)-4-chromanol; MS (M+) 485.3; tlc Rf 0.5 (1:1 hexane:ethyl acetate).

EXAMPLE 48

(±)-trans-3-(3-(Methoxycarbonyl)benzyl)-6-(2-quinolyl)methoxy-4-chromanol

By the method of Example 30, the trans-title product of Example 46 was converted to present title product in about the same yield, m.p. 153°–154° C.

MS (m/e) calculated for C$_{28}$H$_{25}$NO$_5$: 455.1733; found: 455.1721.

EXAMPLE 49

(±)-cis-3-(3-Carboxybenzyl)-6-(2-quinolyl)methoxy-4-chromanol

By the method of Example 42, the title product of Example 47 (0.50 g) was converted to present title product, 0.14 g, m.p. 165°–168° C.

Likewise, the thenyl derivative of Example 47 (0.23 g) was converted to 80 mg of cis-3-(5-carboxy-2-thenyl)-6-(5-fluoro-2-benzthiazolyl)methoxy-4-chromanol, m.p. 193°–195° C.

EXAMPLE 50

(±)-cis-6-(5-Fluoro-2-benzothiazolyl)methoxy-3-3-(3-(methoxycarbonyl)benzyl)-4-chromanol By the method of Example 15, the cis-title product of Example 46 (0.74 g) was converted to present title product, 0.70 g, m.p. 171°–173° C.

EXAMPLE 51

(±)-cis-3-(3-Carboxybenzyl)-6-(5-fluoro-2-benzothiazolyl)methoxy-4-chromanol

By the method of Example 42, the title product of the preceding Example (0.70 g) was converted to present title product, 0.40 g, m.p. 208°–210° C.

EXAMPLE 52

(±)-trans-3-(3-Carboxybenzyl)-6-(2-quinolyl)methoxy-4-chromanol

By the method of Example 43, the title product of Example 48 (0.5 g) was converted to present title product, 0.1 g, m.p. 206°–209° C.

EXAMPLE 53

(±)-trans-6-(5-Fluoro-2-benzothiazolyl)methoxy-3-(3-(methoxycarbonyl)benzyl)-4-chromanol By the method of Example 15, the trans-title product of Example 46 was converted to present title product in about the same yield.

EXAMPLE 54

(±)-trans-6-(5-Fluoro-2-benzothiazolyl)methoxy-3-(3-(carboxybenzyl-4-chromanol

By the method of Example 43, the title product of the preceding Example (0.45 g) was converted to present title product, 0.33 g, m.p. 189°–190° C.

EXAMPLE 55

6-(2-Quinolyl)methoxy-4-chromanone

A mixture of 6-hydroxy-4-chromanone (10.0 g, 0.0609 mol), 2-chloromethylquinoline (11.9 g, 0.0670 mol), sodium iodide (10.0 g, 0.0670 mol), potassium carbonate (25.3 g, 0.183 mol), and acetone (200 ml) was refluxed overnight under N$_2$ atmosphere. After 17 hours the reaction appeared lighter and tlc analysis (10% EtOAc/CH$_2$Cl$_2$) indicated complete conversion of starting material to a slightly less polar product. The mixture was cooled, filtered, and the filtrate concentrated in vacuo. The residue was taken up in ethyl acetate (400 ml), washed with H$_2$O and brine, dried over MgSO$_4$, and concentrated in vacuo to a dark brown oil. Purification on a silica gel column eluted with 10% ethyl acetate/CH$_2$Cl$_2$ gave title product as an off-white solid, 15.3 g (82%), m.p. 112°–114° C.; tlc (1:9 ethyl acetate:CH$_2$Cl$_2$) Rf 0.30.

EXAMPLE 56

3-[4-(Methoxycarbonyl)benzylidene]-6-(2-quinolyl)methoxy-4-chromanone

By the method of Example 1, the product of the preceding Example (5.0 g, 0.0164 mol), methyl 4-formylbenzoate (3.2 g, 0.0194 mol) and pyrrolidine (9.37 ml, 0.0286 mol) were converted to present title product, 5.36 g, tlc (isopropyl ether) Rf 0.25.

EXAMPLE 57

3-[4-(Methoxycarbonyl)benzyl]-6-(2-quinolyl)methoxy-4-chromanone

Title product of the preceding Example (3.6 g) in 50 ml of tetrahydrofuran was hydrogenated on a Parr shaker at 45 psig over 0.40 g of 10% Pd/C for 3 hours. The catalyst was recovered by filtration over diatomaceous earth, and the filtrate stripped to yield crude title product (2.9 g) which was purified by trituration with ether, 1.38 g.

MS (m/e) calculated for C$_{28}$H$_{23}$NO$_5$: 453 1596; found: 453.1552.

EXAMPLE 58 cis and trans-3-[4-(Methoxycarbonyl)benzyl]-6-(2-quinolyl)methoxy-4-chromanol

By the method of Example 4, except to use methanol alone as solvent and 10:1 $CH_2Cl_2$:ethyl acetate as chromatography eluant, the product of the preceding Example (1.3 g) was converted to 1.4 g of crude mixture, separated into 0.14 g of less polar, cis-title product, m.p. 138°–140° C. and 0.13 g of more polar, trans-title product, m.p. 152°–154° C.

MS (m/e) calculated for $C_{28}H_{25}NO_5$: 455.1733; found: 455.1695.

EXAMPLE 59

(±)-trans-3-(4-Carboxybenzyl)-6-(2-quinolyl)methoxy-4-chromanol

By the method of Example 43, the trans-title product of the preceding Example (0.24 g) was converted to present title product, 0.1 g, m.p. 214°–215° C.

EXAMPLE 60

(±)-cis-3-(4-Carboxybenzyl)-6-(2-quinolyl)methoxy-4-chromanol

By the method of Example 42, the cis-title product of Example 58 (0.19 g) was converted to present title product, 0.06 g, m.p. 199°–201° C.

MS (m/e) calculated for $C_{27}H_{23}NO_5$: 441.1576; found: 441.1578.

EXAMPLE 61

3-Hydroxymethylene-6-(2-quinolyl)methoxy-4-chromanone

To a solution of title product of Example 55 (7.00 g, 0.0229 mol) and excess ethyl formate (35 ml) in toluene (80 ml) at room temperature under argon was added in portions over 5 minutes 2.2 g (0.0458 mol) of 50% sodium hydride in mineral oil. The yellow-green mixture was stirred at room temperature for 5 minutes, followed by the addition of 2 drops of ethanol to initiate the reaction. Within 5 minutes the mixture turned red-orange with gas evolution and was mildly exothermic. The mixture was stirred at room temperature for 1 hour, after which tlc (5% $CH_3OH/CH_2Cl_2$) indicated complete conversion of starting material to a more polar product. The reaction mixture was poured into 400 ml of ice water, adjusted to pH 5 with 2N HCl, and extracted with ethyl acetate (500 ml). The organic layer was washed with $H_2O$ and brine, dried over $MgSO_4$, and concentrated in vacuo to a pasty yellow solid. Repeated trituration with hexanes to remove mineral oil gave present title product in 85% yield, tlc (1:19 $CH_3OH:CH_2Cl_2$) Rf 0.40.

EXAMPLE 62

3-Diazo-6-(2-quinolyl)methoxy-4-chromanone

To a solution of the title product of the preceding Example (7.60 g, 0.023 mol) and dry triethylamine (6.4 ml, 0.046 mol) in dry $CH_2Cl_2$ (100 ml) at −30° C. (dry ice-acetone bath) was added dropwise over 20 minutes a solution of tosyl azide (4.5 g, 0.023 mol) in $CH_2Cl_2$ (25 ml). The reaction mixture was allowed to gradually warm to room temperature overnight with stirring. After 18 hours tlc (20% ethyl acetate/$CH_2Cl_2$) indicated complete disappearance of starting material and formation of a less polar product. The mixture was treated with 1N NaOH (100 ml) and stirred for 10 minutes. After treating with brine, the layers were separated and the organic layer was diluted with 200 ml of ethyl acetate. Methylene chloride was then removed in vacuo. The ethyl acetate residue was washed with $H_2O$ and brine, dried over $MgSO_4$, and concentrated in vacuo to give present title product as a dark yellow solid, 6 g (90%); tlc (1:4 ethyl acetate:$CH_2Cl_2$) Rf 0.27.

EXAMPLE 63

3-Phenylthio-6-(2-quinolyl)methoxy-4-chromanone

To a suspension of title product of the preceding Example (3.0 g, 0.0091 mol) and thiophenol (3.0 ml, 0.029 mol) in 15 ml of dry toluene at 70° C. was added 4 mg of rhodium II acetate dimer. Immediately the reaction became homogeneous, turning dark, with gas evolution. Tlc analysis (20% ethyl acetate/$CH_2Cl_2$) indicated complete conversion of starting material to a major less polar product. The reaction was cooled, diluted with ethyl acetate (50 ml), washed with 1N NaOH (3×50 ml), $H_2O$ and brine, dried over $MgSO_4$, and concentrated in vacuo to a dark brown oil. Purification by silica gel column chromatography eluting with 10% ethyl acetate/$CH_2Cl_2$ gave title product, 1.83 g (49%), tlc (1:4 ethyl acetate:CH ) Rf 0.50.

EXAMPLE 64

3-(3-Pyridylthio)-6-(2-quinolyl)methoxy-4-chromanone

By the method of the preceding Example using 15% ethyl acetate/$CH_2Cl_2$ as chromatography eluant, title product of Example 62 (2.00 g) and 2-mercaptopyridine were converted to present title product, 1.13 g (45%); tlc (1:4 ethyl acetate:$CH_2Cl_2$) Rf 0.57.

EXAMPLE 65

3-Benzyloxy-6-(2-quinolyl)methoxy-4-chromanone

By the methods of Example 63, title product of Example 62 (2.00 g) and benzyl alcohol were converted to present title product, 0.94 g (38%); m.p. 113°–115° C., tlc (1:4 ethyl acetate:$CH_2Cl_2$) Rf 0.69.

EXAMPLE 66

(±)-cis and trans-3-Phenylthio-6-(2-quinolyl)methoxy-4-chromanol

To a suspension of the title product of Example 63 (1.85 g, 0.00447 mol) in 70 ml of methanol at 0°–5° C. was added in portions 208 mg (0.00538 mol) of sodium borohydride. The reaction was warmed with stirring to room temperature, then diluted with 20 ml of tetrahydrofuran to obtain a homogeneous mixture, which, after stirring for 1.2 hours was concentrated in vacuo and the residue taken up in 400 ml ethyl acetate, washed with $H_2O$ and brine, dried over $Na_2SO_4$, and concentrated carried out by silica gel column chromatography eluting with 20% ethyl acetate/$CH_2Cl_2$. The less polar cis-title product was isolated as a white solid (1.11 g, 60%). Recrystallization from isopropanol/hexanes gave 1.04 g of white crystals, m.p. 144°–146° C. The more polar trans-title product was obtained as a mixture, contaminated with a small amount of the less polar product. It was re-chromatographed using the same eluant to yield 400 mg (22%) of trans-title product as a white foamy solid. Recrystallization from toluene-hexanes afforded 280 mg of white crystals, m.p. 100°–102° C.

cis-isomer IR(KBr) 750, 1015, 1210, 1500 cm$^{-1}$. MS (m/e) 415.1191.

Analysis calculated for $C_{25}H_{21}NO_3S$: C, 72.27; H, 5.09; N, 3.37%. Found: C, 72.78; H. 5.42; N, 3.36%.

trans-isomer. IR(KBr) 750, 1015, 1215, 1500 cm$^{-1}$. MS (m/e) 415.1311.

Analysis calculated as for cis-isomer. Found: C, 72.10; H, 5.02; N, 3.30%.

EXAMPLE 67

(±)-cis- and trans-3-Pyridylthio-6-(2-quinolyl)methoxy-4-chromanol

By the method of the preceding Example, the title product of Example 64 (1.11 g) was converted to present title products, using 40% ethyl acetate/$CH_2Cl_2$ as eluant in the chromatographic separation.

cis-isomer, 0.50 g (45%), m.p. 136°–138° C. IR(KBr) 1210, 1500 cm$^{-1}$. MS (m/e) 416.1239.

Analysis calculated for $C_{24}H_{20}N_2O_3S$: C, 69.21; H, 4.84; N, 6.73%. Found: C, 68.88; H. 4.86; N, 6.47%.

trans-isomer, 0.44 g (39%), m.p. 52°–55° C. IR(KBr) 1500 cm$^{-1}$.

Analysis calculated as for cis-isomer. Found: C, 68.33; H, 4.82; N, 6.45%.

EXAMPLE 68

(±)-cis-3-(Benzyloxy)-6-(2-quinolyl)-methoxy-4-chromanol

By the method of Example 66, the title product of Example 65, 0.70 g, was converted to present title product, in this instance without isolation of the corresponding trans-isomer. Chromatography on silica gel using 30% ethyl acetate/$CH_2Cl_2$ as eluant gave purified title product, 0.53 g (75%), m.p. 134°–136° C. IR(KBr) 1495 cm$^{-1}$. MS (m/e) 413.1579 (M+).

Analysis calculated for $C_{26}H_{23}NO_4$: C, 75.53; H, 5.61; N, 3.39%. Found: C, 75.29; H, 5.62; N, 3.34%.

EXAMPLE 69

(±)-cis-3-(Phenylsulfinyl)-6-(2-quinolyl)methoxy-4-chromanol

To a solution of the cis-title product of Example 66 (240 mg, 0.57 mmol) in $CH_2Cl_2$ (25 ml) at 0° C. was added 125 mg (0.57 mmol) of m-chloroperbenzoic acid. The reaction was stirred at 0° C. for 2 hours, after which tlc (5% MeOH/$CH_2Cl_2$) indicated complete conversion of starting material to a less polar product. The reaction was diluted with $CH_2Cl_2$ (50–70 ml), washed with saturated $NaHCO_3$, $H_2O$ and brine, dried over $Na_2SO_4$, and concentrated in vacuo to an off-white foamy solid. Purification by silica gel column chromatography eluting with 5% MeOH/$CH_2Cl_2$ gave the sulfoxide title product as a white solid, 240 mg, 96%. Recrystallization from hexane-toluene afforded a white crystalline product, m.p. 174°–176° C. IR (KBr) 1500 cm$^{-1}$.

Analysis calculated for $C_{25}H_{21}NO_4S$: C, 69.59; H, 4.91; N, 3.25%. Found: C, 69.90; H, 4.93; N, 3.21%.

EXAMPLE 70

(±)-trans-3-(Phenylsulfinyl)-6-(2-quinolyl)methoxy-4-chromanol

To a room temperature solution of the trans-title product of Example 66 (230 mg, 0.55 mmol) in methanol (30 ml) was added a solution of $KHSO_3$ (oxone monopersulfate; 340 mg, 0.55 mmol) in $H_2O$ (10 ml). After 0.5 hours, the reaction mixture was diluted with ethyl acetate (300 ml) and $H_2O$ (300 ml). The organic layer was separated, washed with $H_2O$ (2×300 ml) and brine (300 ml), dried over $Na_2SO_4$, and concentrated in vacuo to a foamy solid. Purification by silica gel column chromatography eluting with 5% MeOH/$CH_2Cl_2$ afforded the sulfoxide title product as a foamy solid (185 mg, 77%). Recrystallization from isopropanol/hexane gave 170 mg of white solid, m.p. 169°–171° C. IR (KBr) 1490 cm$^{-1}$.

EXAMPLE 71

(±)-cis-3-(Benzenesulfonyl)-6-(2-quinolyl)methoxy-4-chromanol

To a partial solution of the cis-title product of Example 66 (500 mg, 1.20 mmol) in 50 ml of hot methanol was added a solution of $KHSO_3$ (2.20 g, 3.58 mmol) in $H_2O$ (20 ml). Upon adding the oxone solution, the reaction turned milky with a white precipitate forming. The reaction was stirred at room temperature. After 5 minutes, tlc (20% ethyl acetate/$CH_2Cl_2$) indicated complete conversion of starting material to 2 more polar products in an approximate ratio of 1:1, presumably sulfoxide and sulfone. The reaction was stirred for an additional 25 minutes and then diluted with $H_2O$ (200 ml) and ethyl acetate (250 ml). The organic layer, which still contained a significant amount of undissolved solid, was washed 2×$H_2O$ and brine, and filtered to give 170 mg of white solid. The filtrate was then dried over $Na_2SO_4$ and concentrated in vacuo to give an oil which slowly solidified. Purification by silica gel column chromatography, eluting with 20% ethyl acetate/$CH_2Cl_2$ afforded 300 mg (56%) of sulfone title product as a white solid. Recrystallization from isopropanol/hexane gave 280 mg of white solid, m.p. 168°–171° C. IR (KBr) 1500 cm$^{-1}$. MS (m/e) calculated: 447.1140, found: 447.1149.

EXAMPLE 72

6-Methoxy-3-(3-pyridyloxy)-4-chromanone

To a room temperature solution of 3-hydroxypyridine (7.55 g, 0.0778 mol) in dimethylformamide (400 ml) was added in portions 3.74 g (0.0780 mol) of 50% sodium hydride. The mixture was stirred at room temperature for 30 minutes, followed by the addition of 20.0 g (0.0778 mol) of 3-bromo-6-methoxy-4-chromanone all at once. The resulting red-orange mixture was stirred at room temperature for 1 hour, after which tlc (20% ethyl acetate/$CH_2Cl_2$) indicated complete conversion of starting material to the more polar products. The reaction mixture was poured into 1.2 liter of $H_2O$, adjusted to pH 8–9 with 1N NaOH and extracted with ethyl acetate (2×800 ml). The combined extracts were washed with $H_2O$ and brine, dried over $Na_2SO_4$, and concentrated in vacuo to a yellow oil. Purification by flash column chromatography using 2.3 Kg of fine mesh silica gel and eluting with 20% ethyl acetate/$CH_2Cl_2$ afforded title product as a pale yellow solid in 3.6% yield, m.p. 135°–136° C.

By the same method, 3-hydroxy-6-methylpyridine (17.5 g, 0.16 mol) was converted to 2.22 g of the 6-methylpyridyl analog, m.p. 116°–117° C.

EXAMPLE 73

6-Hydroxy)-3-(3-pyridyloxy)-4-chromanone

To a solution of the title product of the preceding Example (1.60 g, 5.90 mmol) in 150 ml of dry $CH_2Cl_2$ at $-78°$ C. was added slowly via syringe 11.8 ml (11.8 mmol) of 1M boron tribromide over 30 minutes. The resulting red mixture was allowed to gradually warm to $-20°$ C. with stirring and was then placed in the freezer $(-10°$ C.) overnight. The next day the reaction mixture was stirred at $0°-5°$ C. (ice bath) for 1 hour followed by the addition of 150 ml of $H_2O$. The mixture was stirred at $0°-5°$ C. for 2 hours more and then the layers were separated. The organic phase was extracted with 150 ml of $H_2O$ and the combined aqueous extracts were adjusted to pH 8 with 1N NaOH and extracted with ethyl acetate ($2\times$; total of 600 ml). The combined extracts were washed with brine, dried over $Na_2SO_4$, and concentrated in vacuo to a yellow solid. The crude product was chromatographed on a silica gel flash column, eluting with 5% $CH_3OH/CH_2Cl_2$ to afford title product as a yellow solid, 640 mg (42%), tlc (1:19 $CH_3OH:CH_2Cl_2$) Rf 0.21.

EXAMPLE 74 cis-6-Hydroxy-3-(3-pyridyloxy)-4-chromanol

To a solution of the title product of the preceding Example (640 mg, 2.49 mmol) in 2:1 $CH_3OH$:tetrahydrofuran (45 ml) at $0°-5°$ C. was added 96 mg (2.49 mmol) of sodium borohydride. The yellow solution was stirred at room temperature and turned almost colorless within 5 minutes at which time tlc (10% MeOH/$CH_2Cl_2$) indicated complete conversion of starting material to the more polar product. Approximately 20 mg more $NaBH_4$ was added, the mixture stirred for 10 minutes, and then concentrated in vacuo. The crude mixture was purified by flash chromatography on a short silica column, eluting with 10% $CH_3OH/CH_2Cl_2$ to afford present title product as a white solid, 610 mg (94%), m.p. $194°-197°$ C.

EXAMPLE 75

($\pm$)-cis-6-(6-Fluoro-2-quinolyl)methoxy-3-(3-pyridyloxy)-4-chromanol

To a room temperature solution of the title product of the preceding Example (450 mg, 1.74 mmol) and 6-fluoro-2-chloromethylquinoline (374 mg, 1.91 mmol) in dimethylformamide (17 ml) was added in portions 92 mg (1.91 mmol) of 50% sodium hydride in oil. The mixture was stirred at room temperature, the color gradually changing from light yellow to brown. After 1 hour, tlc (10% $CH_3OH/CH_2Cl_2$) indicated formation of a major less polar product and only a trace of starting material. The reaction mixture was poured into 200 ml of $H_2O$ and extracted with ethyl acetate ($2\times200$ ml). The combined extracts were washed with $H_2O$ and brine, dried over $Na_2SO_4$, and concentrated in vacuo to a dark yellow oil. Purification by silica gel flash column chromatography, eluting with 5% $CH_3OH/CH_2Cl_2$, afforded title product as an off-white solid, 460 mg (63%). Recrystallization from isopropyl ether-$CH_2Cl_2$ gave 420 mg of white crystalline solid, m.p. $157°-159°$ C.

IR (KBr) 1240, 1480, 1495 cm$^{-1}$. MS (m/e) 418.1302.

Analysis calculated for $C_{24}H_{19}FN_2O_4$: C, 68.89; H, 4.58; N, 6.69%. Found: C, 69.20; H, 4.41; N, 6.62%.

EXAMPLE 76

($\pm$)-cis-3-(3-Pyridyloxy)-6-(2-quinolyl)methoxy-4-chromanol

By the methods of the preceding Example, substituting a molar equivalent of 2-chloromethylquinoline for the 6-fluoro-2-chloromethylquinoline, the title product of Example 74 (0.26 g) was converted to present chromatographed title product, 0.35 g (88%), also recrystallized from isopropyl ether/$CH_2Cl_2$, m.p. $126°-128°$ C.

IR (KBr) 1500 cm$^{-1}$. MS (m/e) 400.1433.

Analysis calculated for $C_{24}H_{20}N_2O_4$: C, 71.99; H, 5.03; N, 7.00%. Found: C, 71.52; H, 4.90; N, 6.86%.

EXAMPLE 77

($\pm$)-cis-6-(5-Fluoro-2-benzothiazolyl)methoxy-3-(3-pyridyloxy)-4-chromanol By the method of Example 75, substituting a molar equivalent of 2-chloromethyl-5-fluorobenzothiazole for the 6-fluoro-2-chloromethylquinoline, the title product of Example 74 (0.40 g) was converted to present chromatographed title product; 0.19 g (29%), also recrystallized from isopropyl ether/$CH_2Cl_2$, m.p. $213°-215°$ C.

IR (KBr) 1260, 1495 cm$^{-1}$. MS (m/e) 424.0870.

EXAMPLE 78

($\pm$)-cis-6-(2-Pyridyl)methoxy-3-(3-pyridyloxy)-4-chromanol

By the method of Example 75, substituting a molar equivalent of 2-picolyl chloride for the 6-fluoro-2-chloromethylquinoline and replacing the chromatography eluant with ethyl acetate, title product of Example 74 (0.246 g) was converted to present chromatographed title product, 0.19 g (57%), also recrystallized from isopropyl ether/$CH_2Cl_2$, m.p. $148°-150°$ C.

IR (KBr) 1270, 1435, 1500 1590 cm$^{-1}$.

Analysis calculated for $C_{20}H_{18}N_2O_4$: C, 68.56; H, 5.18; N, 8.00%. Found: C, 68.19; H, 4.77; N, 7.81%.

EXAMPLE 79

($\pm$)-cis-6-(3-Pyridyl)methoxy-3-(3-pyridyloxy)-4-chromanol

By the method of Example 75, substituting a molar equivalent of 3-picolyl chloride for the 6-fluoro-2-chloromethylquinoline and using 10% methanol/ethyl acetate as chromatography eluant, title product of Example 74 (0.259 g) was converted to present chromatographed title product, 0.23 g (66%), recrystallized in the manner of the preceding Example, m.p. $139°-141°$ C.

IR (KBr) 1425, 1500, 1575 cm$^{-1}$. MS (m/e) 350.1272 (M$^+$).

EXAMPLE 80

($\pm$)-cis-6-(4-Pyridyl)methoxy-3-(3-pyridyloxy)-4-chromanol

By the method of Example 75, substituting a molar equivalent of 4-picolyl chloride for the 6-fluoro-2-chloromethylquinoline and using the same chromatography eluant as in the preceding Example, the title product of Example 74 (0.259 g) was converted to present chromatographed title product, 0.23 g (66%), recrystallized in the manner of Example 78, m.p. $149°-151°$ C.

IR (KBr) 1260, 1280, 1490, 1575 cm$^{-1}$.

Analysis calculated for $C_{20}H_{18}N_2O_4$ C, 68.56; H, 5.18; N, 8.00%. Found: C, 68.12; H, 5.12; N, 7.78%.

EXAMPLE 81

6-Methoxy-3-(2-thiazolyl)methylene-4-chromanone

By the method of Example 1, 6-methoxy-4-chromanone (3.97 g, 0.0223 mol) and 2-thiazolecarbaldehyde (3.00 g, 0.0265 mol) were converted to present title product which was recrystallized from methanol, 1.20 g (20%), m.p. 130°–132° C., tlc (1:19 $CH_3OH:CH_2Cl_2$) Rf 0.67.

EXAMPLE 82

3-(3-Indolyl)methylene-6-methoxy-4-chromanone

By the method of Example 1, 6-methoxy-4-chromanone (10.0 g) and 3-indolecarbaldehyde were converted to present title product recrystallized from $CH_3OH/CH_2Cl_2$, 16.7 g (98%), m.p. 217°–219° C.

EXAMPLE 83

6-Methoxy-3-(2-thiazolyl)methyl-4-chromanone

By the method of Example 2, the title product of Example 81 (1.20 g, 0.0044 mol) was converted to present title product recrystallized from hexanes, 1.01 g (83%), m.p. 71°–73° C., tlc (1:1 ethyl acetate:$CH_2Cl_2$) Rf 0.39.

EXAMPLE 84

3-(3-Indolyl)methyl-6-methoxy-4-chromanone

By the method of Example 2, the title product of Example 82 (15.5 g) was converted to present title product, recrystallized from isopropanol/hexanes, 12.5 g (80%), m.p. 121°–123° C.

EXAMPLE 85

6-Hydroxy-3-(2-thiazolyl)methyl-4-chromanone

By the method of Example 3, the title product of Example 83 (2.10 g) was converted to present title product recrystallized from isopropyl ether/hexanes, 1.80 g (95%), m.p. 150°–152° C., tlc (1:19 $CH_3OH:CH_2Cl_2$) Rf 0.23.

EXAMPLE 86

6-Hydroxy-3-(3-indolyl)methyl-4-chromanone

By the method of Example 73, the title product of Example 84 (2.50 g) was converted to present title product, 0.43 g (18%), m.p. 188°–190° C.

EXAMPLE 87 cis- and trans-3-[(2-Thiazolyl)methyl]chroman-4,6-diol

By the method of Example 4, the title product of Example 85 (1.74 g) was converted to a crude product, purified but not separated by column flash chromatography on silica gel, eluting with 1:9 $CH_3OH:CH_2Cl_2$, to yield present title products as a mixture, 1.73 g (98%), m.p. 50° C.

EXAMPLE 88 cis- and trans-3-[(3-Indolyl)methyl]chroman-4,6-diol

By the method of Example 4, the title product of Example 86 (0.40 g) was converted to a mixture of present title products, 0.40 g, m.p. 78° C. (dec.).

EXAMPLE 89

(±)-cis- and trans-6-(2-Quinolyl)methoxy-3-(2-thiazolyl)methyl-4-chromanol

By the method of Example 5, using 1:39 $CH_3OH:CH_2Cl_2$ as eluant in the chromatographic separation of the cis-trans isomers, and recrystallizing the final products from isopropyl ether-hexane, the title product mixture of Example 87 was converted to less polar cis-title product, 0.28 g (40%), m.p. 50° C. (dec.), and more polar trans-title product, 0.27 g (39%), m.p. 125°–127° C.

cis-isomer. IR(KBr) 1210, 1495 cm$^{-1}$.

trans-isomer. IR(KBr) 1225, 1495 3280 cm$^{-1}$.

Analysis calculated for $C_{23}H_{20}N_2O_3S$: C, 68.19; H, 4.75; N, 6.60%. Found: C, 68.19; H, 4.75; N, 6.60%.

EXAMPLE 90

(±)-cis- and trans-6-(6-Fluoro-2-quinolyl)methoxy-3-(2-thiazolyl)methyl-4-chromanol By the method of Example 5, using the same eluant as the preceding Example for initial chromatography, the mixed title products of Example 87 (0.45 g) and 2-chloromethyl-6-fluoroquinoline were converted to less polar cis-title product, triturated with hexanes, 0.18 g (24%), m.p. 47° C. (dec.) and crude, more polar trans-isomer. The latter was purified by column chromatography, using 30% hexane/ethyl acetate as eluant, thus yielding the trans-title product, 0.24 g (33%), recrystallized from isopropyl ether/$CH_2Cl_2$, m.p. 159°–161° C.

cis-isomer. IR(KBr) 1210, 1500 cm$^{-1}$. MS (m/e) 422.1057.

trans-isomer. IR(KBr) 1220, 1495 cm$^{-1}$. MS (m/e) 422.1103.

Analysis calculated for $C_{23}H_{19}FN_2O_3S$: C, 65.39; H, 4.53; N, 6.63%. Found: C, 64.81; H, 4.00; N, 6.20%.

EXAMPLE 91

(±)-cis- and trans-6-(5-Fluoro-2-benzothiazolyl)methoxy-3-(2-thiazolyl)methyl-4-chromanol By the method of Example 5, the mixed title products of Example 87 (0.43 g) and 2-chloromethyl-5-fluorothiazole were converted to a crude mixture of title products. The trans-title isomer crystallized from the crude product with $CH_3CN$, yield 0.08 g (12%) of this isomer, m.p. 168°–170° C. The mother liquor was stripped and column chromatographed on silica gel using the eluant of Example 89 to yield the cis-isomer, 0.14 g, recrystallized from isopropyl ether/$CH_2Cl_2$, m.p. 138°–140° C.

cis-isomer. IR(KBr) 1220, 1500 cm$^{-1}$. MS (m/e) 428.0689.

Analysis calculated for $C_{21}H_{17}FN_2O_3S$: C, 58.73; H, 4.22; N, 6.52%. Found: C, 58.66; H, 4.03; N, 6.42%.

trans-isomer. IR(KBr) 1430, 1460 1500 cm$^{-1}$. MS (m/e) 428.0689.

Analysis calculated as for cis-isomer. Found: C, 58.71; H, 4.09; N, 6.50%.

EXAMPLE 92

(±)-cis-3-(3-Indolyl)methyl-6-(2-quinolyl)methoxy-4-chromanol

By the method of Example 5, without isolation of the corresponding trans-isomer in this instance, the mixed title products of Example 88 (0.38 g) and 2-chloromethylquinoline, using 40% ethyl acetate/hexane as eluant on chromatography, were converted to present less polar title product, 0.163 g (29%), recrystallized from isopropyl ether/hexane, m.p. 60° C. MS (m/e) 436.1762.

EXAMPLE 93

(±)-cis-6-(2-Pyridyl)methoxy-3-(3-pyridyl)methyl-4-chromanol

By the method of Example 5, using 10% isopropanol/$CH_2Cl_2$ as chromatography eluant, but without isolation of the corresponding trans-isomer in this instance, the mixed title products of Example 4 (1.00 g) and 2-picolyl chloride were converted to present less polar title product in similar yield, recrystallized from isopropanol/hexane, m.p. 108°–110° C.

IR(KBr) 1220, 1505 cm$^{-1}$. MS (m/e) 348.1500.

Analysis calculated for $C_{21}H_{20}N_3O_3$: C, 72.40; H, 5.79; N, 8.04%. Found: C, 72.30; H, 5.66; N, 7.87%.

EXAMPLE 94

(±)-cis- and trans-6-(1-Methyl-2-benzimidazolyl)methoxy-3-(3-pyridyl)methyl-4-chromanol By the method of Example 5, using the chromatography eluant of the preceding Example, the mixed title products of Example 4 (0.97 g) were converted to present less polar cis-title product, 0.5 g (30%), recrystallized from isopropanol/hexane, m.p. 151°–153° C., and more polar trans-title product, 0.27 g (18%), also recrystallized from isopropanol/hexane, m.p. 181°–183° C.

cis-isomer. IR(KBr) 1215, 1500 cm$^{-1}$. MS (m/e) 401.1717.

trans-isomer. IR(KBr) 1490 cm$^{-1}$. MS (m/e) 401.1721.

Analysis calculated for $C_{24}H_{23}N_3O_3$: C, 71.80; H, 5.77; N, 10.47%. Found: C, 70.63; H, 5.67; N, 10.14%.

EXAMPLE 95 cis-6-(3-Pyridyl)methoxy-3-(3-pyridyl)methyl-4-chromanol

By the method of Example 89, the product of Example 4A (0.70 g) and 3-picolyl chloride were converted to present title product, 0.61 g (64%), m.p. 145°–147° C.

IR(KBr) 1500 cm$^{-1}$. MS (m/e) 348.1464 (M+).

Analysis calculated for $C_{21}H_{20}N_2O_3$: C, 72.40; H, 5.79; N, 8.04%. Found: C, 72.01; H, 5.77; N, 7.98%.

EXAMPLE 96 cis-6-(4-Pyridyl)methoxy-3-(3-pyridyl)methyl-4-chromanol

By the method of Example 89, the product of Example 4A (0.70 g) and 4-picolyl chloride were converted to present title product, 0.57 g (60%), m.p. 100°–102° C.

IR(KBr) 1220, 1500 cm$^{-1}$. MS (m/e) 348.1474 (M+).

Analysis calculated as for preceding Example. Found: C, 72.19; H, 5.72; N, 7.81%.

EXAMPLE 97

7,8-Dihydro-7-methyl-3-(2-quinolyl)methoxy-5(6H)-quinolone

By the method of Example 55, 7,8-dihydro-3-hydroxy-7-methyl-5(6H)-quinolone and 2-chloromethylquinoline were converted to present title product in 67% yield, m.p. 141°–144° C.

MS (m/e) calculated: 318.1365; found: 318.1325.

EXAMPLE 98

7-Methyl-6(8H)-(3-pyridyl)methylene-3-(2-quinolyl)methoxy-5(7H)-quinolone

By the method of Example 1, the title product of the preceding Example was converted to present title product in 54% yield.

MS (m/e) 407.2 (M+); tlc (19:1 $CH_2Cl_2$:ethanol) Rf 0.12.

EXAMPLE 99 cis- and trans-7,8-Dihydro-7-methyl-6-(3-pyridyl)methyl-3-(2-quinolyl)methoxy-5(6H)-quinolone By the method of Example 2, the title product of the preceding Example was converted to a mixture of present title products in 42% yield; MS (m/e) 409.1 (M+); tlc (9:1 $CH_2Cl_2$:ethanol) Rf 0.5. It is believed that this product is a mixture of 6,7-cis and 6,7-trans-isomers, although the possibility that the product comprises substantially one or the other of these isomers is not excluded.

EXAMPLE 100

5,6,7,8-Tetrahydro-c- and t-7-methyl-c-6-(3-pyridyl)methyl-3-(2-quinolyl)methoxy-r-5-quinolol and 5,6,7,8-Tetrahydro-c- and t-7-methyl-t-6-(3-pyridyl)methyl-3-(2-quinolyl)methoxy-r-5-quinolol By the method of Example 4, except to use ethyl acetate as solvent, the product of the preceding Example was converted to present chromatographically separated title products named according to the *IUPAC Nomenclature of Organic Chemistry*, 1979 Ed., pp. 477-8. Each of these products is believed to be a mixture of two compounds, one having the 7-methyl group cis(c) relative(r) to the 5-hydroxy group and the other having the 7-methyl group trans(t) relative(r) to the 5-hydroxy group. However, the possibility that each of these products comprises substantially one or the other of these c-7 or t-7 isomers is not excluded.

r-5, c-6-isomer(s) 47% yield, m.p. 179°–181° C.; less polar; MS (m/e) 411.3 (M+), exact mass calculated: 411.1945, found: 411.1941.

r-5, t-6-isomer(s) 10% yield, m.p. 190°–193° C.; more polar; MS (m/e) calculated: 411.1945, found: 411.1896.

Analysis calculated for $C_{26}H_{25}N_3O_2$: C, 75.89; H, 6.12; N, 10.21%. Found: C, 75.78; H, 6.22; N, 9.82%.

EXAMPLE 101

6(8H)-Hydroxymethylene-7-methyl-3-(2-quinolyl)methoxy-5(7H)-quinolone

By the method of Example 61, the title product of Example 97 was converted to present title product in yield; tlc (19:1 $CH_2Cl_2$:ethanol) Rf 0.6.

EXAMPLE 102

6(8H)-Diazo-7-methyl-3-(2-quinolyl)methoxy-5(7H)-quinolone

By the method of Example 62, the title product of the preceding Example was converted to present title product in 99% yield; tlc (19:1 $CH_2Cl_2$:ethanol Rf 0.25.

EXAMPLE 103 cis- and trans-7,8-Dihydro-7-methyl-6-phenoxy-3-(2-quinolyl)-methoxy-5(6H)-quinolone (See Example 99 for comment re isomer composition.)

By the method of Example 63, the title product of the preceding Example and phenol were converted to a mixture of present title products in 50% yield; MS (m/e) 410.1 (M+); tlc (19:1 $CH_2Cl_2$:ethanol) Rf 0.56.

EXAMPLE 104

5,6,7,8-Tetrahydro-c- and t-7-methyl-c-6-phenoxy-3-(2-quinolyl)methoxy-r-5-quinolol and 5,6,7,8-Tetrahydro-c- and t-7-methyl-t-6-phenoxy-3-(2-quinolyl)methoxy-r-5-quinolol (See Example 100 for comments re nomenclature and isomer composition.)

By the method of Example 66, the title products of the preceding Example were converted to present, chromatographically separated title products.

r-5, c-6-isomer(s) 43% yield, m.p. 166°–167° C.; less polar. MS (m/e) calculated: 412.1787, found: 412.1829.

r-5, t-6-isomer(s) 6% yield, m.p. 129°–132° C.; more polar. MS (m/e) calculated: 412.1787, found: 412.1778.

EXAMPLE 105

6(8H)-Benzylidene-3-benzyloxy-7-methyl-5(7H)-quinolone

By the method of Example 1, 3-benzyloxy-7,8-dihydro-3-methyl-5(6H)-quinolone and benzaldehyde were converted to present title product in 95% yield; MS calculated: 355.1752, found: 355.1567.

EXAMPLE 106 cis- and trans-6-Benzyl-7,8-dihydro-3-hydroxy-7-methyl-5(6H)-quinolone (See Example 99 for comment re isomer composition.)

By the method of Example 2, the title product of the preceding Example was converted to a mixture of present title products in 67% yield; MS (m/e) 267.1 (M+); tlc (9:1 $CH_2Cl_2$:ethyl acetate) Rf 0.08.

EXAMPLE 107

5,6,7,8-Tetrahydro-6-benzyl-7-methyl-3,5-quinolinediols

By the method of Example 4, the title products of the preceding Example were converted to present title products in 99% yield, understood to be a mixture of r-5,c-6,c-7; r-5,t-6,c-7; r-5,c-6,t-7; and r-5,t-6,t-7 geometric isomers of similar polarity; tlc (9:1 $CH_2Cl_2$:$CH_3OH$) Rf 0.3.

EXAMPLE 108 c-6-Benzyl-5,6,7,8-tetrahydro-c- and t-7-methyl-3-(2-quinolyl)methoxy-r-5-quinolol and t-6-Benzyl-5,6,7,8-tetrahydro-c- and t-7-methyl-3-(2-quinolyl)methoxy-r-5-quinolol (See Example 100 for comments re nomenclature and isomer composition.)

By the method of Example 5, the product of the preceding Example was converted to present chromatographically separated title products.

r-5, c-6-isomer(s) 18% yield, m.p. 146.5°–147.5° C.; less polar. MS (m/e) calculated: 410.1994, found: 410.2045.

r-5, t-6-isomer(s) 18% yield, m.p. 151°–151.5° C.; more polar. MS (m/e) calculated: 410.1994, found: 410.1998.

EXAMPLE 109

(±)-cis- and trans-3-(3-Pyridyl)methyl-6-(2-quinoxalinyl)methoxy-4-chromanol

By the method of Example 5, using gradient elution with 39:1, 29:1 and finally 19:1 $CH_2Cl_2$ $CH_3OH$ in chromatography, the title products of Example 4 and 2-chloromethylquinoxaline were converted to chromatographically separated title products, the cis recrystallized from toluene and the trans recrystallized from $CH_2Cl_2$ cis-isomer. 16% yield, m.p. 168.5°–169.5° C.; less polar. MS (m/e) calculated: 399.1583, found: 399.1569.

trans-isomer. 8% yield, m.p. 141.5°–143° C.; more polar. MS (m/e) calculated: 399.1583, found: 399.1571.

EXAMPLE 110 cis-3-(4-Methoxyphenoxy)-6-(2-pyridyl)methoxy-4-chromanol

By the method of Example 13, using flash chromatography with 39:1 $CH_2Cl_2$ isopropanol as eluant and recrystallization from isopropyl ether/$CH_2Cl_2$ for purification of the product, the title product of Example 20 and 2-picolyl chloride were converted to present title product in 26% yield, m.p. 117°–118° C. MS calculated: 379.1420, found: 379.1412.

EXAMPLE 111 cis-6-(6-Fluoro-2-quinolyl)-3-(4-methoxyphenoxy)-4-chromanol

By the method of Example 13, using flash chromatography with 35:1 $CH_2Cl_2$:isopropanol as eluant and recrystallization from $CH_2Cl_2$ for purification of the product, the title product of Example 20 (0.20 g, 0.69 mmol) and 6-fluoro-2-chloromethylquinoline were converted

EXAMPLE 112 cis-6-(6-Fluoro-2-quinolyl)-3-(3-methoxyphenoxy)-4-chromanol

By the method of Example 13, using flash chromatography with 49:1 $CH_2Cl_2$:isopropanol as eluant and recrystallization as in the preceding Example, the title product of Example 25 (0.37 g, 0.00128 mol) and 2-chloromethyl-7-fluoroquinoline were converted to present title product, 0.39 g from the column, 0.113 g after recrystallization, m.p. 131°–132° C. MS (m/e) calculated: 447.1486, found: 447.1497.

EXAMPLE 113 cis-3-(3-Methoxyphenoxy)-6-(2-pyridyl)methoxy-4-chromanol

By the method of Example 13, using flash chromatography with 40:9:1 $CH_2Cl_2$:hexane:isopropanol as eluant and recrystallization from 1:1 toluene:hexane, the title product of Example 25 (0.37 g, 0.00128 mol) and 2-picolyl chloride were converted to present title product, 0.15 g (30%), m.p. 105°–107° C. MS (m/e) calculated: 379.1424, found: 379.1394.

EXAMPLE 114

Diastereomeric cis-6-(6-Fluoro-2-quinolyl)methoxy-3-(3-pyridyloxy)-4-chromanyl N-(R-1-Naphthylethyl)carbamates The title product of Example 75 (0.93 g, 0.0022 mol), toluene (30 ml) and R-(1-naphthylethyl) isocyanate (2.0 g, 0.01 mol) were combined in the order listed and the mixture heated at reflux for 18 hours by which time tlc (19:1 $CH_2Cl_2$:$CH_3OH$) indicated at least 95% conversion to a less polar product. The reaction mixture was then cooled to room temperature washed 3×10 ml $H_2O$ and the $H_2O$ layer back-washed 2×8 ml ethyl acetate. The organic layers were combined, dried over $MgSO_4$ and stripped to a gum (2.83 g), which was flash chromatographed on silica gel, using 1:1 toluene:ethyl acetate as eluant, to yield a purified mixture of the title diastereoisomers, 1.2 g. The diastereoisomers were separated by HPLC with 53:47 hexanes:ethyl acetate as eluant to yield less polar diasteroisomer, 0.52 g; a mixture of diastereoisomers suitable for recycling, 0.23 g; and more polar diastereoisomer, 0.31 g.

EXAMPLE 115

(−)-cis-6-(6-Fluoro-2-quinolyl)methoxy-3-(3-pyridyloxy)-4-chromanol

A flame-dried flask under dry $N_2$ was charged in sequence with the less polar diastereoisomer of the preceding Example (0.497 g, 0.81 mmol), benzene (30 ml), triethylamine (0.404 g, 0.56 ml, 0.004 mol) and $HSiCl_3$ (0.542 g, 0.40 ml, 0.004 mol) with vigorous stirring. The mixture was stirred for 61 hours at room temperature by which time tlc (19:1 $CH_2Cl_2$:$CH_3OH$) indicated complete conversion to a single, more polar product. The reaction mixture was quenched with 60 ml $H_2O$, the pH adjusted to 7 with 1N NaOH, and the resulting emulsion filtered over diatomaceous earth. The filtrate phases were separated and the aqueous phase washed 2×30 ml ethyl acetate. The organic layers were combined, dried over $MgSO_4$ and the dry solution combined with 3 cc silica gel and the mixture stripped to dryness. The dry silica gel/product mixture charge to a silica gel chromatography column which was eluted with 19:1 $CH_2Cl_2$:isopropanol and the resulting chromatographed title product recrystallized from methanol, 0.16 g, m.p. 163°–164° C., believed to be the 3S,4R-isomer, $[\alpha]_D^{21} = -57°$ [c=1.3 in $CH_2Cl_2$].

EXAMPLE 116

(+)-cis-6-(6-Fluoro-2-quinolyl)methoxy-3-(3-pyridyloxy)-4-chromanol

By the method of the preceding Example, the more polar diastereoisomer of Example 114 (0.30 g, 0.49 mmol) was converted to present title product, 1.0 g, m.p. 163.5°–164.5° C., believed to be the 3R,4S-isomer, $[\alpha]_D^{21} = +57°$ [c=1.1 in $CH_2Cl_2$].

EXAMPLE 117 cis-6-(6-Fluoro-2-quinolyl)methoxy-3-(3-methoxyphenoxy)-4-chromanyl N,N-Dimethylglycinate Title product of Example 112 (0.10 g, 0.22 mmol) was dissolved in $CH_2Cl_2$ (3 ml). 4-(Dimethylamino)pyridine (0.043 g, 0.35 mmol), N,N-dimethylglycine hydrochloride (0.038 g, 0.26 mmol) and dicyclohexylcarbodiimide (0.050 g, 0.26 mmol) were then added in the listed sequence and the mixture was stirred for 18 hours at which time tlc (1:1 toluene:ethyl acetate/1% triethylamine) indicated complete conversion to a single, more polar product. The reaction mixture was directly chromatographed on a silica gel column using 1:1 toluene:ethyl acetate/1% triethylamine as eluant to yield purified title product as a white solid, 0.10 g (86%). MS (m/e) 532.3 (M+); tlc (1:1 toluene:ethyl acetate/1% triethylamine) Rf 0.32.

EXAMPLE 118 cis-6-(6-Fluoro-2-quinolyl)methoxy-3-(3-methoxyphenoxy)-4-chromanyl N,N-Dimethylglycinate Dihydrochloride To the product of the preceding Example (0.10 g, 0.19 mmol) dissolved in 5 ml absolute ethanol was added 0.475 ml (0.475 mmol) of 1N HCl and the mixture stirred for several minutes, then stripped to dryness, and restripped 3×5 ml absolute ethanol and finally 1×5 ml $CH_2Cl_2$ to yield title product as a white solid, 0.11 g (95.6%), m.p. 149°–152° C.

EXAMPLE 119 cis-3-(3-Methoxyphenoxy)-6-(2-quinolyl)methoxy-4-chromanyl N,N-Dimethylglycinate To a solution of the title product of Example 26 (0.493 g), 4-(dimethylamino)pyridine (0.226 g) and N,N-dimethylglycine hydrochloride (0.193 g) in 30 ml of $CH_2Cl_2$ was added a solution of dicyclohexylcarbodiimide in 5 ml of $CH_2Cl_2$. After stirring 18 hours, by-product dicyclohexyl urea was recovered by filtration and the filtrate stripped to an oily solid which was chromatographed on a silica gel column with ether as eluant to yield purified title product, 0.44 g. $^1$H-NMR($CDCl_3$)delta(ppm): 2.15 (s, 6H), 3.15 (s, 2H), 3.80 (s, 3H), 4.30 (d, J=5Hz, 2H), 4.90 (m, 1H), 6.30 (d, J=3, 1H), 6.30–8.30 (m, 13H).

EXAMPLE 120 cis-3-(3-Methoxyphenoxy)-6-(2-quinolyl)methoxy-4-chromanyl N,N-Dimethylglycinate Dihydrochloride Title product of the preceding Example (0.44 g) was reacted by the method of Example 118, but the reaction mixture was simply stripped to dryness and title product crystallized from isopropanol, 0.39 g, decomposes on heating without melting.

EXAMPLE 121 cis-3-(4-Methoxyphenoxy)-6-(2-quinolyl)methoxy-4-chromanyl N,N-Dimethylglycinate By the method of Example 119, the title product of Example 21 (0.40 g) was converted to present title product, 0.43 g, tlc (9:1 ethyl acetate:CH$_3$OH) Rf 0.5.

EXAMPLE 122 cis-3-(4-Methoxyphenoxy)-6-(2-quinolyl)methoxy-4-chromanyl N,N-Dimethylglycinate Dihydrochloride By the method of Example 120, the title product of the preceding Example (0.35 g) was converted to present title product, 0.31 g, decomposes on heating without melting.

EXAMPLE 123 cis-3-Phenoxy-6-(2-quinolyl)methoxy-4-chromanyl N,N-Dimethylglycinate

By the method of Example 119, the title product of Example 13 (0.40 g) was converted to present title product, 0.43 g. $^1$H-NMR(CDCl$_3$)delta(ppm): 2.20 (s, 6H), 3.10 (s, 2H), 4.30 (d, J=5, 2H), 4.90 (s, 1H), 5.30 (s, 2H), 6.30 (d, J=3, 1H), 6.80–8.30 (m, 14H).

EXAMPLE 124 cis-3-Phenoxy-6-(2-quinolyl)methoxy-4-chromanyl N,N-Dimethylglycinate Dihydrochloride By the method of Example 120, the title product of the preceding Example was converted to present title product, 0.40 g, m.p. 157° C. (dec.).

EXAMPLE 125

6-Benzyloxy-3-(4-methoxy-3-(methoxycarbonyl)benzylidene)-4-chromanone

By the method of Example 44, 6-benzyloxy-4-chromanone (20.95 g) and 4-methoxy-3-methoxycarbonylbenzaldehyde were converted to present title product, 25.75 g (73%); tlc (19:1 CH$_2$Cl$_2$:ether) Rf 0.70.

EXAMPLE 126

6-Hydroxy-3-(4-methoxy-3-(methoxycarbonyl)benzyl)-4-chromanone

By the method of Example 45, the title product of the preceding Example (25.75 g) was converted to present title product, 13.2 g (64.5%); tlc (ether) Rf 0.40. $^1$H-NMR(CDCl$_3$)delta(ppm): 2.60–3.20 (m, 3H), 3.90 (s, 3H), 3.95 (s, 3H), 4.1 (d, J=3, 1H), 4.35 (d, J=3, 1H), 6.80–7.70 (m, 6H).

EXAMPLE 127 cis- and trans-3-(4-methoxy-3-(methoxycarbonyl)benzyl)-4,6-chromandiol

By the method of Example 39, using 10% ether/CH$_2$Cl$_2$ as eluant for chromatographic separation, the title product of the product of the preceding Example (13.2 g) was converted to present less polar cis-title product, 6.2 g, tlc (7:3 CH$_2$Cl$_2$:ether) Rf 0.30, and more polar trans-title product, 3.94 g, tlc (7:3 CH$_2$Cl$_2$:ether) Rf 0.25.

EXAMPLE 128 cis-3-(4-Methoxy-3-(methoxycarbonyl)benzyl)-6-(2-quinolyl)methoxy-4-chromanol

By the method of Example 30, the cis-title product of the preceding Example (1.0 g) and 2-chloromethylquinoline were converted to present title product, purified by column chromatography on silica gel using 5% ether/CH$_2$Cl$_2$ as eluant, 0.50 g. $^1$H-NMR(CDCl$_3$)delta(ppm): 2.3–2.9 (m, 3H), 2.90 (s, 3H), 2.95 (s, 3H), 4.0 (m, 2H), 4.4 (s, 1H), 5.25 (s, 2H), 6.70–8.20 (m, 12H).

EXAMPLE 129 cis-6-(5-Fluoro-2-benzothiazolyl)methoxy-3-(4-methoxy-3-(methoxycarbonyl)benzyl)-4-chromanol By the method of Example 15, the cis-title product of Example 127 (1.0 g) and 2-chloromethyl-5-fluorobenzothiazole were converted to present title product, purified by chromatography as in the preceding Example, 0.84 g, m.p. 160°–162° C. $^1$H-NMR(CDCl$_3$)delta(ppm): 2.3–2.9 (m, 3H), 2.90 (s, 3H), 2.95 (s, 3H), 4.0 (d, J=2, 2H), 4.40 (s, 1H), 5.30 (s, 2H), 6.70–7.80 (m, 9H).

EXAMPLE 130 trans-3-(4-Methoxy-3-(methoxycarbonyl)benzyl)-6-(2-quinolyl)methoxy-4-chromanol

By the method of Example 30, the trans-title product of Example 127 (1.0 g) and 2-chloromethylquinoline were converted to present title product, purified by chromatography as in Example 128, 0.88 g. $^1$H-NMR(CDCl$_3$)delta(ppm): 2.1–2.8 (m, 3H), 2.90 (s, 6H), 4.10 (d, J=4, 1H), 4.4 (s,1), 5.25 (s, 2H), 6.70–8.20 (m, 12H).

EXAMPLE 131 trans-6-(5-Fluoro-2-benzothiazolyl)methoxy-3-(4-methoxy-3-(methoxycarbonyl)benzyl)-4-chromanol By the method of Example 15, the trans-title product of Example 127 (0.60 g) and 2-chloromethyl-5-fluorobenzothiazole were converted to present title product, purified by chromatography according to Example 128, 0.43 g. $^1$-NMR(CDCl$_3$)delta(ppm): 2.1–2.8 (m, 3H), 2.90 (s, 6H), 4.15 (d, J=4, 1H), 4.4 (s,1H), 5.30 (s, 2H), 6.70–7.80 (m, 9H).

EXAMPLE 132 cis-3-(3-Carboxy-4-methoxybenzyl)-6-(2-quinolyl)methoxy-4-chromanol

By the method of Example 42, the title product of Example 128 (0.88 g) was converted to present title product, 0.25 g, m.p. 167°–169° C.

EXAMPLE 133 cis-3-(3-Carboxy-4-methoxybenzyl)-6-(5-fluoro-2-benzothiazolyl)methoxy-4-chromanol By the method of Example 42, the title product of Example 129 (0.83 g) was converted to present title product, 0.56 g, m.p. 197°–198° C.

EXAMPLE 134 trans-3-(3-Carboxy-4-methoxybenzyl)-6-(2-quinolyl)-methoxy-4-chromanol

By the method of Example 42, the title product of Example 130 (0.50 g) was converted to present title product, 0.35 g, m.p. 172°-174° C.

EXAMPLE 135 trans-3-(3-Carboxy-4-methoxybenzyl)-6-(5-fluoro-2-benzothiazolyl)methoxy-4-chromanol By the method of Example 42, the title product of Example 131 (0.42 g) was converted to present title product, 0.28 g, m.p. 149°-151° C.

EXAMPLE 136

2-Benzyl-3,4-dihydro-7-methoxy-1(2H)-naphthalenone

To a −78° C. solution of lithium diisopropyl amide (from 43.8 ml (0.312 mol) of diisopropyl amine in 280 ml tetrahydrofuran and 119 ml (0.298 mol) of 2.5M n-butyllithium) was slowly added a solution of 50 g (0.285 mol) of 7-methoxy-3,4-dihydro-1(2H)-naphthalenone in 100 ml tetrahydrofuran. The resultant reaction mixture was stirred 10 minutes at −78° C. The cooling bath was charged to a 0° C. ice bath, followed immediately by the rapid addition of 38 ml (0.32 mol) of benzyl bromide. Hexamethylphosphoramide (106 ml, 0.60 mol) was then added and the resultant solution stirred at 25° C. for 2 hours. The reaction was added to saturated $NH_4Cl$ and saturated NaCl, dried over $MgSO_4$, and evaporated to an oil, which was purified via column chromatography on 1 Kg of silica gel eluted with 10% ether-hexane to give 20 g (26%) of the title compound as an oil.

MS (m/e) 266 (M+), 175 and 91. IR ($CHCl_3$) 1677, 1608, 1491 $cm^{-1}$. $^1$-NMR($CDCl_3$, 300 MHz)delta(ppm): 1.70 (m,1H), 2.03 (m,1H), 2.5-2.9 (m, 4H), 3.42 (dd, J=12, 3 Hz, 1H), 3.79 (s, $OCH_3$), 6.98 (dd, J=8, 2 Hz, ArH), 7.07 (d, J=8 Hz, ArH), 7.2 (m, 5ArH) and 7.49 (d, J=2 Hz, ArH).

EXAMPLE 137

2-Benzyl-3,4-dihydro-7-hydroxy-1(2H)-naphthalenone

A mixture of 9.00 g (33.8 mmol) of the title product of the preceding Example in 32 ml acetic acid and 32 ml concentrated HBr was heated at reflux for 8 hours. The reaction was cooled and slowly added to 150 ml ice and water. The precipitated needle crystals were collected by filtration and dried in vacuo to give 8.46 g (99%) of the title compound. A portion was recrystallized from ether/hexane, 158°-160° C. (dec.).

MS (m/e) 252 (M+), 174, 161, 133, 115, 106 and 91. IR (KBr) 1677, 1610 $cm^{-1}$. $^1$H-NMR($CDCl_3$-DMSO-$d_6$, 300 MHz)delta(ppm): 1.57 (m, 1H), 1.90 (m, 1H), 2.4-2.7 (m, 4H), 3.28 (dd, J=14, 3 Hz, 1H), 6.83 (dd, J=8, 2 Hz, ArH), 6.91 (d, J=8 Hz, ArH), 7.08 (m, 5 ArH), 7.33 (d, J=2 Hz, ArH) and 8.86 (s, OH).

Analysis calculated for $C_{17}H_{16}O_2$: C, 80.93; H, 6.39% Found: C, 81.25; H, 6.16%.

EXAMPLE 138

2-Benzyl-7-(2-quinolyl)methoxy-3,4-dihydro-1(2H)-naphthalenone

A mixture of 3.87 g (15.4 mmol) of the title product of the preceding Example, 4.7 g (22.9 mmol) 2-chloromethylquinoline, 17.9 g (54.9 mmol) cesium carbonate and 220 mg (0.849 mmol) cesium iodide in 33 ml acetone was heated at reflux for 15 hours. The reaction was cooled, diluted with ether and filtered. Evaporation of the filtrate gave an oil. This crude product was crystallized from ether-hexane to give 4.17 g (69%) of the title compound, m.p. 117°-118° C.

MS (m/e) 393 (M+), 143, 142, 115 and 91. IR ($CHCl_3$) 1678, 1604, 1568 $cm^{-1}$. $^1$-NMR($CDCl_3$, 300 MHz)delta(ppm): 1.72 (m, 1H), 2.06 (m, 1H), 2.5-3.0 (m, 4H), 3.46 (m, 1H), 5.40 (s, $OCH_3$), 7.2 (m, 7H), 7.52 (dd, J=8, 8 Hz, 1ArH), 7.65 (m, 3ArH), 7.80 (d, J=8 Hz, ArH), 8.07 (d, J=8 Hz, ArH) and 8.17 (d, J=8 Hz, ArH).

Analysis calculated for $C_{27}H_{23}NO_2$: C, 82.42; H, 5.89; N, 3.56%. Found: C, 82.32; H, 5.91; N, 3.51%.

EXAMPLE 139 cis- and trans-2-Benzyl-1,2,3,4-tetrahydro-7-(2-quinolyl)methoxy-1-naphthol

To a 0° C. solution of 3.00 g (7.63 mmol) of the title product of the preceding Example in 100 ml 1:1 methanol:tetrahydrofuran was added portionwise 1.5 g (39.5 mmol) of sodium borohydride and the reaction stirred for 15 hours. The reaction was concentrated on a rotating evaporator and the residue dissolved in a mixture of ethyl acetate and saturated NaCl. The organic layer was washed with saturated NaCl, dried over $MgSO_4$ and evaporated to a solid, which was purified via medium pressure liquid chromatography on silica gel eluted with 66% ether-hexane to give in order of elution 1.09 g (36%) of cis-title product and 1.68 g (56%) of trans-title product as oils. Crystallization was achieved from diisopropyl ether-dichloromethane to give 850 mg of the cis and 1.30 g of the trans isomer.

cis-isomer. m.p. 113°-115° C.; MS (m/e) 395 (M+), 286, 142, 130, 115 and 91. IR ($CHCl_3$) 3596, 3435, 1602, 1576 $cm^{-1}$. $^1$-NMR($CDCl_3$, 300 MHz)delta(ppm): 1.5-1.9 (m, 3H), 1.96 (m, 1H), 2.5-2.84 (m, 2H and OH), 2.90 (m, 1H), 4.42 (bs, OCH), 5.31 (s, $OCH_2$), 6.96 (dd, J=8, 2 Hz, ArH), 6.92 (d, J=2 Hz, ArH), 6.99 (J=8 Hz, ArH), 7.22 (m, 5ArH), 7.50 (dd, J=8, 8 Hz, ArH), 7.60 (d, J=8 Hz, ArH), 7.69 (dd, J=8, 8 Hz, ArH), 7.78 (d, J=8 Hz, ArH), 8.03 (d, J=8 Hz, ArH) and 8.13 (d, J=8 Hz, ArH).

Analysis calculated for $C_{27}H_{25}NO_2$: C, 82.00; H, 6.37; N, 3.54% Found: C, 82.11; H, 6.36; N, 3.50% trans-isomer. m.p. 112°-113° C.; MS (m/e) 395 (M+), 304, 303, 286, 143, 142, 115 and 91. IR ($CHCl_3$) 3578, 3350, 1601, 1576 $cm^{-1}$. $^1$-NMR($CDCl_3$, 300 MHz)delta(ppm): 1.20 (m, 1H), 1.9 (m, 3H), 2.43 (dd, J=12, 8 Hz, 1H), 2.62 (m, 1H and OH), 3.03 (dd, J=13, 5 Hz, 1H), 4.19 (dd, J=7, 7 Hz, OCH), 5.32 (s, $OCH_2$), 6.92 (dd, J=8, 2 Hz, ArH), 6.94 (d, J=8 Hz, ArH), 7.15 (m, 5ArH), 7.48 (dd, J=8, 8 Hz, ArH), 7.62 (d, J=8 Hz, ArH), 7.62 (dd, J=8, 8 Hz, ArH), 7.76 (d, J=8 Hz, ArH), 8.02 (d, J=8 Hz, ArH) and 8.12 (d, J=8 Hz, ArH).

Analysis calculated for $C_{27}H_{25}NO_2$: C, 82.00; H, 6.37; N, 3.54% Found: C, 82.18; H, 6.39; N, 3.49%

EXAMPLE 140 trans-2-Benzyl-1,2,3,4-tetrahydro-7-(2-quinolyl)methoxy-1-naphthol Hydrochloride To a 0° C. solution of 1.00 g (2.53 mmol) of trans-title product of the preceding Example in 100 ml ethanol was added 2.53 ml of 1N hydrochloric acid (2.53 mmol). The reaction solvent was evaporated on a rotating evaporator, and the residue diluted with 100 ml ethanol and evaporated, a process which was repeated 3× to give dry material. The residue was crystallized from dichloromethane-ether to give 855 mg (78%) of the title compound, m.p. 183°–185° C. $^1$-NMR(CDCl$_3$, 300 MHz)delta(ppm): 1.40 (m, 1H), 1.8–2.05 (m, 2H), 2.47 (dd, J=13, 8 Hz, 1H), 2.73 (m, 2H), 3.19 (dd, J=14, 4 hz, 1H), 4.50 (d, J=7 Hz, OCH), 5.85 (d, J=15 Hz, OCH$_2$ 1H), 5.99 (d, J=15 Hz, OCH$_2$ 1H), 6.86 (dd, J=8, 2 Hz, ArH), 6.97 (d, J=8 Hz, ArH), 7.26 (m, 5ArH), 7.54 (d, J=2 Hz, ArH), 7.86 (dd, J=8, 8 Hz, ArH), 8.08 (m, 3ArH), 8.75 (d, J=8 Hz, ArH) and 8.98 (d, J=8 Hz, ArH).

EXAMPLE 141

1R,2R- and 1S,2S-(trans)-2-Benzyl-1,2,3,4-tetrahydro-7-(2-quinolyl)methoxy-1-naphthyl R-O-Acetylmandelate To a 0° C. solution of 2.00 g (10.3 mmol) of (R)-O-acetylmandelic acid and 1.26 g (10.3 mmol) of 4-N,N-dimethylaminopyridine in 16 ml CH$_2$Cl$_2$ was added 3.40 g (8.60 mmol) of trans-title product of Example 139, followed by 1.95 g (9.46 mmol) of dicyclohexylcarbodiimide. The reaction was then stirred at 25° C. for 24 hours. The reaction was filtered and the filtrate evaporated to a crude oil. This oil was purified via column chromatography on 500 g of silica gel eluted with 50% ether-hexane to give in order of elution 1.93 g (39%) of the 1R,2R-title product and 2.03 g (41%) of the 1S,2S-title product. The former was crystallized from ether/hexane.

1R,2R-diastereomer m.p. 150°–151° C.; MS (m/e) 571 (M+), 378, 296, 286, 261, 241, 142, 125, 111, 97 and 85. IR (CHCl$_3$) 1741, 1602, 1600 cm$^{-1}$. $^1$-NMR(CDCl$_3$, 300 MHz)delta(ppm): 1.28 (m, 1H), 1.94 (m, 1H), 2.22 (s, CH$_3$CO), 2.24 (m, 1H), 2.36 (m, 1H), 2.66 (m, 2H), 2.96 (dd, J=13, 3 hz, 1H), 4.94 (d, J=15 Hz, OCH$_2$ 1H), 5.04 (d, J=15 Hz, OCH$_2$ 1H), 5.90 (d, J=7 Hz, OCH), 5.94 (s, OCH), 6.36 (d, J=2 Hz, ArH), 6.81 (dd, J=8, 2 Hz, ArH), 6.96 (d, J=8 Hz, ArH), 7.1–7.3 (m, 9ArH), 7.56 (m, 3ArH), 7.75 (dd, J=8 Hz, ArH), 7.85 (d, J=8 Hz, 1ArH), 8.11 (d, J=8 Hz, 1ArH) and 8.20 (d, J=8 Hz, ArH).

Analysis calculated for C$_{37}$H$_{33}$NO$_5$: C, 77.74; H, 5.83; N, 2.45%. Found: C, 78.30; H, 5.87; N, 2.41%.

1S,2S-diastereomer. $^1$-NMR(CDCl$_3$, 300 MHz)delta(ppm): 1.20 (m, 1H), 1.77 (m, 1H), 1.97 (m, 1H), 2.15 (m, 1H), 2.26 (s, CH$_3$CO), 2.45 (dd, J=15, 2 hz, 1H), 2.65 (m, 2H), 5.36 (AB pattern, OCH$_2$), 5.91 (d, J=7 Hz, OCH), 5.98 (s, OCH), 6.85–7.04 (m, 5ArH), 7.2 (m, 4ArH), 7,38 (m, 3ArH), 7.55 (m, 2ArH), 7.72 (m, 2ArH), 7.84 (d, J=8 Hz, 1ArH), 8.11 (d, J=8 Hz, ArH) and 8.21 (d, J=8 Hz, ArH).

EXAMPLE 142

1R,2R-2-Benzyl-1,2,3,4-tetrahydro-7-(2-quinolyl)methyl-1-naphthol

A mixture of 1.70 g (2.98 mmol) of 1R,2R-title product of the preceding Example and 4.75 g (34.4 mmol) of anhydrous K$_2$CO$_3$ in 35 ml tetrahydrofuran, 35 ml methanol and 9 ml water was stirred at 25° C. for 20 hours. The reaction was concentrated on a rotating evaporator and the residue dissolved in a mixture of 300 ml water and 100 ml ether. The combined organic layer and two further 100 ml ether extracts were dried over MgSO$_4$ and evaporated. The resultant solid was recrystallized from CH$_2$Cl$_2$/hexane to give 1.10 g (93%) of present title compound, m.p. 130°–132° C.

IR (CHCl$_3$) 3580, 3387, 1602, 1580 cm$^{-1}$. MS (m/e) 395 (M+), 376, 366, 348, 303, 286, 253, 143, 142, 115 and 91. $^1$-NMR(CDCl$_3$, 300 MHz)delta(ppm): 1.25 (m, 1H), 1.80 (d, J=7 Hz, OH), 1.84–2.6 (m, 2H), 2.48 (dd, J=16, 10 hz, 1H), 2.67 (m, 2), 3.07 (dd, J=15, 6 Hz, 1H), 4.43 (dd, J=7, 7 Hz, OCH), 5.37 (s, OCH$_2$), 6.85 (dd, J=8, 2 Hz, ArH), 6.98 (d, J=8 Hz, ArH), 7.1–7.4 (m, 6ArH), 7.52 (dd, J=8, 8 Hz, ArH), 7.66 (d, J=8 Hz, ArH), 7.71 (dd, J=8, 8 Hz, ArH), 7.81 (d, J=8 Hz, ArH), 8.06 (d, J=8 Hz, ArH) and 8.16 (d, J=8 Hz, ArH).

Analysis calculated for C$_{27}$H$_{25}$NO$_2$: C, 82.00; H, 6.37; N, 3.54%. Found: C, 81.90; H, 6.42; N, 3.51%.

[alpha]$_D^{20}$ = −55.3° (methanol c=0.01).

1S,2S-2-Benzyl-1,2,3,4-tetrahydro-7-(2-quinolyl)methoxy-1-naphthol

Using the method of the preceding Example, 700 mg (1.23 mmol) of the 1S,2S-title product of Example 141 gave 393 mg (81%) of present title compound, recrystallized from dichloromethane/diisopropyl ether, m.p. 131°–132° C.

IR (CHCl$_3$) 3581, 3375, 1602, 1493 cm$^{-1}$. MS (m/e) 396 (M+), 376, 303, 286, 253, 143, 142, 115 and 91. [alpha]$_D^{20}$ = +55.26° (methanol c=0.01026).

EXAMPLE 144 trans-2-Benzyl-1,2,3,4-tetrahydro-7-(2-quinolyl)methoxy-1-naphthyl 4-Piperidinobutyrate Dihydrochloride To a 0° C. solution of 935 mg (4.52 mmol) of 4-piperidinobutyric acid hydrochloride, 733 mg (6.01 mmol) 4-(N,N-dimethylamino)pyridine and 1.49 g (3.77 mmol) of the trans-title product of Example 139 in 7.5 ml CH$_2$Cl$_2$ was added 852 mg (4.14 mmol) dicyclohexylcarbodiimide. The resultant reaction mixture was stirred 15 hours at 25° C., then filtered and the filtrate evaporated to an oil. The latter was purified via column chromatography on 120 g silica gel eluted with 10% methanol-CH$_2$Cl$_2$ to yield a second oil, which was dissolved in 100 ml ethanol. 1N Hydrochloric acid (7.54 ml) was added, and the reaction concentrated to dryness on a rotating evaporator. The residue was twice dissolved in 100 ml ethanol and evaporated to give a solid. This solid was recrystallized from CH$_2$Cl$_2$ and diisopropyl ether to give 2.00 g (85%) of the title compound, m.p. 132°–135° C.

IR (KBr) 1745, 1648, 1606 cm$^{-1}$. MS (m/e) 549 (M+-2HCl), 405, 286, 170, 142, 98 and 91. $^1$H-NMR(DMSO-d$_6$, 300 MHz)delta(ppm): 1.3–2.1 (m), 2.1–3.0 (m), 3.36 (m, 2H), 5.47 (s, OCH$_2$), 5.73 (d, J=7 Hz, OCH), 6.80 (d, J=2 Hz, ArH), 7.00 (dd, J=8, 2 Hz, ArH), 7.10 (d, J=8 Hz, ArH), 7.13–7.32 (m, 5ArH), 7.73 (dd, J=8, 8 Hz, ArH), 7.81 (d, J=8 Hz, ArH), 7.92 (dd, J=8, 8 Hz, ArH), 8.12 (d, J=8 Hz, ArH), 8.18 (d, J=8 Hz, ArH) and 8.66 (d, J=8 Hz, ArH).

Analysis calculated for C$_{36}$H$_{42}$Cl$_2$N$_2$O$_3$·1.5H$_2$O: C, 66.66; H, 6.99; N, 4.32%. Found: C, 66.20; H, 6.82; N, 4.23%.

EXAMPLE 145

3,4-Dihydro-7-(2-quinolyl)methoxy-1(2H)-naphthalenone

By the method of Example 138, 5.00 g (30.9 mmol) of 7-hydroxy-3,4-dihydro-1(2H)naphthalenone and 9.91 g (46.3 mmol) of 2-chloromethylquinoline hydrochloride gave 3.5 g (37%) of the title compound.

MS (m/e) 303 (M+), 286, 274, 142, and 115. $^1$H-NMR(CDCl$_3$, 300 MHz)delta(ppm): 2.08 (m, 2H), 2.60 (t, J=7 Hz, CH$_2$), 2.87 (t, J=6 Hz, CH$_2$), 5.39 (s, OCH$_2$), 7.16 (d, J=2 Hz, ArH), 7.52 (dd, J=8, 8 Hz, ArH), 7.6-7.75 (m, 4ArH), 7.79 (d, J=8 Hz, ArH), 8.07 (d, J=8 Hz, ArH) and 8.16 (d, J=8 Hz, ArH).

EXAMPLE 146

2-(3-Pyridylmethylene)-7-(2-quinolyl)methoxy-3,4-dihydro-1(2H)-naphthalenone

A solution of 3.50 g (11.5 mmol) of the title product of the preceding Example, 2.47 g (23.1 mmol) of 3-pyridine carbaldehyde and 1.9 ml (23 mmol) of pyrrolidine in 12 ml methanol was heated at reflux for 22 hours. The reaction was cooled and added to 300 ml saturated NaCl and 150 ml ethyl acetate. The organic layer was combined with two further 150 ml ethyl acetate extracts, dried over MgSO$_4$, evaporated to dryness and the residue triturated with ether to give 2.95 g (66%) of the title compound, m.p. 147°-148° C.

MS (m/e) 392 (M+), 363, 300, 142, and 115. IR (CHCl$_3$) 1667, 1600, 1566 cm$^{-1}$. $^1$-NMR(CDCl$_3$, 300 MHz)delta(ppm): 2.90 (t, J=7 Hz, 2H), 3.08 (t, J=7 Hz, 2H), 5.43 (s, OCH$_2$), 7.1-7.4 (m, 3ArH), 7.54 (dd, J=8, 8 Hz, ArH), 7.4-7.9 (m, 6ArH), 8.08 (d, J=8 Hz, ArH), 8.19 (d, J=8 Hz, ArH), 8.54 (d, J=2 Hz, ArH) and 8.66 (s, vinyl H).

EXAMPLE 147

2-(3-Pyridylmethyl)-7-(2-quinolyl)methoxy-3,4-dihydro-1(2H)-naphthalenone and cis-2-(3-Pyridylmethyl)-7-(2-quinolyl)methoxy-1,2,3,4-tetrahydro-1-naphthol A mixture of 3.30 g (8.42 mmol) of the title product of the preceding Example and 500 mg of 10% Pd/C in 177 ml of tetrahydrofuran was stirred under 1 atmosphere of hydrogen. When hydrogen uptake ceased, the reaction was filtered and the filtrate evaporated to a solid. Column chromatography of this solid on 500 g of silica gel using 25% acetonitrile-dichloromethane as eluant gave in order of elution 1.35 g (41%) of ketonic title product as a solid, m.p. 115°-117° C., and 350 mg (11%) of the cis-naphthol title product, recrystallized from dichloromethane, m.p. 157°-160° C.

EXAMPLE 148 cis- and trans-1,2,3,4-Tetrahydro-2-(3-pyridylmethyl)-7-(2-quinolyl)methoxy-1-naphthol To a 0° C. solution of 1.35 g (3.43 mmol) of the ketonic title product of the preceding Example in 45 ml of 1:1 methanol:tetrahydrofuran was added 320 mg (8.57 mmol) of NaBH$_4$. The reaction was stirred for 2 hours and then added to 200 ml saturated NaCl and 150 ml CH$_2$Cl$_2$. The organic layer was combined with two additional 150 ml CH$_2$Cl$_2$ extracts, dried over MgSO$_4$, and evaporated to a solid, which was purified via column chromatography on 500 g of silica gel eluting with 10% isopropyl alcohol-CH$_2$Cl$_2$ to give in order of elution the title-cis-isomer, identical with the cis-isomer of the preceding Example, and the title-trans-isomer as an oil.

EXAMPLE 149

2-Benzylidene-6-methoxy-1-indanone

To a 0° C. mixture of 9.66 g (59.6 mmol) of 6-methoxy-1-indanone and 6.32 g (59.6 mmol) of benzaldehyde in 10 ml ethanol was added 9.66 ml of a 4% KOH in ethanol solution. The reaction was stirred 1 hour and then added to 300 ml water and the pH of the quench adjusted to 2 with 1N hydrochloric acid. The resultant mixture was extracted with 3×300 ml ether, and the extracts combined, dried over MgSO$_4$, evaporated and the residue triturated with ether to yield 10.8 g (72%) of present title compound as a solid. $^1$-NMR(CDCl$_3$, 300 MHz)delta(ppm): 3.80 (s, OCH$_3$), 3.92 (s, CH$_2$), 7.13 (dd, J=8, 2 Hz, ArH), 7.35 (m, 4ArH and vinyl H) and 7.6 (m, 3ArH).

EXAMPLE 150

2-Benzyl-6-methoxy-1-indanone

By the method of Example 147, 9.94 g (39.8 mmol) of the title product of the preceding Example and 100 g of 10% Pd/C in 500 ml ethyl acetate was converted to 8.04 g (80%) of present title compound as a solid from hexane.

MS (m/e) 252 (M+), 161 and 91. $^1$-NMR(CDCl$_3$, 300 MHz)delta(ppm): 2.62 (dd, J=13, 10 hz, 1H), 2.74 (d, J=13 hz, 1H), 2.92-3.12 (m, 2H), 3.34 (dd, J=16, 3 Hz, 1H), 3.80 (s, OCH$_3$), 7.08°-7 5 (m 8ArH)

EXAMPLE 151

2-Benzyl-6-hydroxy-1-indanone

By the method of Example 137, 8.00 g (31.7 mmol) of the title product of the preceding Example gave 7.44 g (97%) of present title compound, recrystallized from water-acetic acid, m.p. 140°-143° C.

MS (m/e) 238 (M+), 161, 147 and 91. IR (CHCl$_3$) 3665, 3583, 1701, 1618, 1602 cm$^{-1}$. $^1$-NMR(CDCl$_3$, 300 MHz)delta(ppm): 2.62 (dd, J=15, 12 hz, 1H), 2.74 (d, J=15 hz, 1H), 2.93-3.13 (m, 2H), 3.34 (dd, J=12, 3 Hz, 1H), 7.10 (dd, J=8, 2Hz, ArH) and 7.23 (m, 7ArH).

EXAMPLE 152

2-Benzyl-6-(2-quinolyl)methoxy-1-indanone

By the method of Example 138, 3.50 g (14.7 mmol) of the title product of the preceding Example and 4.80 g (22.4 mmol) of 2-chloromethylquinoline hydrochloride gave 890 mg (16%) of present title compound, recrystallized from ether, m.p. 104°-106° C.

MS (m/e) 379 (M+), 344, 143, 115 and 91. IR (CHCl$_3$) 1705, 1617, 1603, 1567 cm$^{-1}$. $^1$-NMR(CDCl$_3$, 300 MHz)delta(ppm): 2.60 (dd, J=13, 10 hz, 1H), 2.74 (dd, J=16, 3hz, 1H), 2.9-3.1 (m, 2H), 3.33 (dd, J=11, 3 Hz, 1H), 5.36 (s, OCH$_3$), 7.1-7.4 (m, 8ArH), 7.51 (dd, J=8, 8 Hz, ArH), 7.59 (d, J=8 Hz, ArH), 7.70 (dd, J=8, 8 Hz, ArH), 7.79 (d, J=8 Hz, ArH), 8.05 (d, J=8 Hz, ArH) and 8.15 (d, J=8 Hz, ArH).

EXAMPLE 153 cis- and trans-2-Benzyl-6-(2-quinolyl)methoxy-1-indanol

By the method of Example 139, 0.89 g (2.35 mmol) of the title product of the preceding Example gave in order of elution 220 mg (25%) of the cis-title product, m.p. 138°-139° C., and 459 mg (52%) of the trans-title product, m.p. 137°-138° C.

cis-isomer. MS (m/e) 381 (M+), 272, 142, 115 and 91. IR (CHCl$_3$) 3593, 3432, 1613, 1603, 1584, 1567 cm$^{-1}$. $^1$H-NMR(CDCl$_3$, 300 MHz)delta(ppm): 2.6-2.8 (m, 4H), 3.07 (dd, J=13, 6 hz, 1H), 4.92 (bs, with D$_2$O; d, J=6 Hz, OCH), 5.37 (s, OCH$_2$), 6.92 (dd, J=8, 2 Hz, ArH), 7.04 (d, J=2 Hz, ArH), 7.11 (d, J=8 Hz, ArH), 7.15-7.4 (m, 5ArH), 7.54 (dd, J=8, 2 Hz, ArH), 7.65 (d, J=8 Hz, ArH), 7.72 (dd, J=8, 8 Hz, ArH), 7.81 (d, J=8 Hz, ArH), 8.07 (d, J=8 Hz, ArH) and 8.17 (d, J=8 Hz, ArH).

Analysis calculated for $C_{26}H_{23}NO_2$: C, 81.B6: H. 6.08; N. 3.67% Found: C, 81.86; H, 6.00; N, 4.06%.

trans-isomer. MS (m/e) 381 (M+), 272, 142, 130, and 91. IR (CHCl$_3$) 3585, 3436, 1614, 1602, 1568 cm$^{-1}$. $^1$H-NMR(CDCl$_3$, 300 MHz)delta(ppm): 2.5 (m, 2H), 2.76 (dd, J=15, 9 hz, 1H), 2.9 (m, 1H), 3.06 (dd, J=12, 6 Hz, 1H), 4.88 (bs, with D$_2$O; d, J=6 Hz, OCH), 5.36 (s, OCH$_2$), 6.87 (dd, J=8, 2 Hz, ArH), 7.02 (m, 2ArH), 7.1-7.4 (m, 5ArH), 7.52 (dd, J=8, 2 Hz, ArH), 7.64 (d, J=8 Hz, ArH), 7.71 (dd, J=8, 8 Hz, ArH), 7.80 (d, J=8 Hz, ArH), 8.06 (d, J=8 Hz, ArH) and 8.16 (d, J=8 Hz, ArH).

Analysis calculated for $C_{26}H_{23}NO_2$: C, 81.86; H, 6.08; N, 3.67% Found: C, 81.51; H, 6.05; N, 3.57%.

EXAMPLE 154

2-Benzyl-6-(2-pyridyl)methoxy-1-indanone

By the method of Example 138, 3.50 g (14.7 mmol) of the title product of Example 151 and 3.61 g (22.0 mmol) of 2-chloromethylpyridine hydrochloride were converted to 3.40 g (69%) of present title compound, recrystallized from CH$_2$Cl$_2$-hexane, m.p. 94°-97° C.

MS (m/e) 329 (M+), 314, 300, 238, 93, 92 and 91. IR (CHCl$_3$) 1704, 1617, 1595, 1574 cm$^{-1}$. $^1$-NMR(CDCl$_3$, 300 MHz)delta(ppm): 2.61 (dd, J=15, 11 hz, 1H), 2.73 (dd, J=15, 4 Hz, 1H), 2.9-3.1 (m, 2H), 3.34 (dd, J=12, 4 Hz, 1H), 5.19 (s, OCH$_2$), 7.1-7.4 (m, 9ArH), 7.44 (d, J=8 Hz, ArH), 7.67 (dd, J=8, 8 Hz, ArH) and 8.56 (J=5 Hz, ArH).

EXAMPLE 155 cis- and trans-2-Benzyl-6-(2-pyridyl)-methoxy-1-indanol

By the method of Example 139, the title product of the preceding Example (3.40 g, 10.3 mmol) was converted to present title products, giving in order of elution 810 mg (24%) of cis-title product, m.p. 124.5°-125.5° C. and 1.32 g (39%) of trans-title product, m.p. 112°-113° C., both recrystallized from CH$_2$Cl$_2$/isopropyl ether.

cis-isomer. MS (m/e) 331 (M+), 313, 240, 222, 115 and 91. IR (CHCl$_3$) 3591, 1613, 1596, 1574 cm$^{-1}$. $^1$-NMR(CDCl$_3$, 300 MHz)delta(ppm): 2.75 (m, 4H), 2.09 (dd, J=12, 6 hz, 1H), 4.95 (d, J=6 Hz, OCH), 5.20 (s, OCH$_2$), 6.90 (dd, J=8, 2 Hz, ArH), 7.02 (d, J=2 Hz, ArH), 7.12 (d, J=8 Hz, ArH), 7.2-7.4 (m, 6 ArH), 7.52 (d, J=8 Hz, ArH), 7.72 (dd, J=8, 8 Hz, ArH) and 8.57 (d, J=5 Hz, ArH).

Analysis calculated for $C_{22}H_{21}NO_2$: C, 79.73; H, 6.39; N, 4.23%. Found: C, 79.38; H, 6.32; N, 4.11% trans-isomer. MS (m/e) 331 (M+), 240, 239, 222, 148 and 91. IR (CHCl$_3$) 3586, 3411, 1613, 1596, 1575 cm$^{-1}$. $^1$H-NMR(CDCl$_3$, 300 MHz)delta(ppm): 2.55 (m, 2H), 2.77 (dd, J=14, 8 hz, 1H), 2.92 (m, 1H), 3.09 (dd, J=12, 6 Hz, 1H), 4.89 (d, J=6 Hz, OCH), 5.19 (s, OCH$_2$), 6.85 (dd, J=8, 2 Hz, ArH), 7.00 (d, J=2 Hz, ArH), 7.05 (d, J=8 Hz, ArH), 7.15-7.4 (m, 6 ArH), 7.51 (d, J=8 Hz, ArH), 7.70 (dd, J=8, 8 Hz, ArH) and 8.56 (d, J=5 Hz, ArH).

Analysis calculated for $C_{22}H_{21}NO_2$: C, 79.73; H, 6.39; N, 4.23%. Found: C, 79.67; H, 6.37; N, 4.16%.

EXAMPLE 156

3,4-Dihydro-7-methoxy-2-phenoxy-1(2H)-naphthalenone

A mixture of 2.95 g (31.4 mmol) of phenol, 25.5 g (78.2 mmol) of cesium carbonate and 320 mg (1.23 mmol) of cesium iodide in 64 ml of acetone was heated at reflux for 40 minutes and then cooled to 0° C. To this 0° C. mixture was added 8.00 g (31.4 mmol) of 2-bromo-3,4-dihydro-7-methoxy-1(2H)-naphthalenone. The resultant reaction mixture was stirred 3 hours at 0° C. and 15 hours at 25° C., then filtrated. The filtrate was evaporated to an oil which was purified via column chromatography on 400 g of silica gel, eluting with 25% ether-hexane, to give 5.14 g (61%) of present title product as an oil, crystallized from ether-hexane, m.p. 94.5°-96.5° C.

MS (m/e) 268 (M+), 174, 173, 160, 147, 131, 120 115 and 103. IR (CHCl$_3$) 1696, 1610, 1598 cm$^{-1}$. $^1$H-NMR(CDCl$_3$)delta(ppm): 2.3-2.7 (m, 2H), 3.0-3.4 (m, 2H), 3.82 (s, OCH$_3$), 4.88 (dd, J=8, 6 Hz, OCH) and 6.9-7 6 (m, 8ArH).

Analysis calculated for $C_{17}H_{16}O_3$: C, 76.10; H, 6.01%. Found: C, 75.75; H, 5.95%.

EXAMPLE 157 cis- and trans-1,2,3,4-Tetrahydro-7-methoxy-2-phenoxy-1-naphthol

By the method of Example 139, 2.86 g (10.8 mmol) of title product of the preceding Example gave 2.88 g (100%) of a mixture of present title products as a solid.

MS (m/e) 270 (M+), 176, 159, 147 and 121. IR (CHCl$_3$) 3560, 1611, 1597, 1588 cm$^{-1}$. $^1$H-NMR(CDCl$_3$, 300 MHz)delta(ppm): 1.9 (m, 1H), 2.3 (m, 1H), 2.65 (m, 1H), 2.85 (m, 1H), 3.79 (s, OCH$_3$), 4.45, 4.69, 4.85 (m, 2H), 6.79, 7.0, 7.25 (m., 8ArH).

EXAMPLE 158 cis- and trans-2-Phenoxy-1,2,3,4-tetrahydro-1,7-naphthalenediol

To a solution of 2.80 g (10.4 mmol) of the title products of the preceding Example in 5 ml of hexamethylphosphoramide (distilled in vacuo from sodium was added 15.66 ml (about 42 mmol) of a solution of lithium n-propylmercaptide (made from 74.6 mmol of propanethiol in 75 ml of tetrahydrofuran and 44 ml of 1.6N n-butyl-lithium in hexane, followed by dilution with 70 ml hexamethylphosphoramide). The reaction solution was heated at 105° C. for 4.5 hours and then stirred for 15 hours at 25° C. The reaction was added to 200 ml water containing 2.6 ml concentrated hydrochloric acid. The quenched reaction was extracted with two 100 ml portions of ether. The combined ether extracts were washed with water and saturated NaCl, dried over MgSO$_4$, and evaporated to a solid. Recrystallization from benzene gave 1.94 g (73%) of present title products as a mixture of cis and trans-isomers, m.p. 140°-157° C.

MS (m/e) 256 (M+), 162, 145 and 133. IR (KBr) 1615, 1597, 1588 cm$^{-1}$. $^1$-NMR(CDCl$_3$, 300 MHz)delta(ppm): 1.85 (m, 1H), 2.18 (m, 1H), 2.5-2.9 (m, 2H), 4.39, 4.55, 4.7 (m, 2H), 6.64, 6.85, 7.15 (m, 8ArH).

Analysis calculated for $C_{16}H_{16}O_3$: C, 74.98; H, 6.29%. Found: C, 74.79; H, 6.26%.

EXAMPLE 159 cis- and trans-2-Phenoxy-7-(2-quinolyl)methoxy-1,2,3,4-tetrahydro-1-naphthol By the method of Example 138, 1.82 g (7.16 mmol) of the title product of the preceding Example and 2.30 g (10.8 mmol) of 2-chloromethylquinoline hydrochloride gave 2.2 g of a cis-trans mixture of the title compounds after silica gel column chromatography. Separation of isomers was achieved via HPLC on a 21.4 mm×25 cm Dynamax Macro HPLC Si column eluted with 15% ether-dichloromethane (16 ml/min) to give the less polar cis-isomer (186 mg, 6%) and the more polar trans-isomer (28 mg, 1%) as pure fractions.

cis-isomer. m.p. 118° C.; MS (m/e) 397 (M+), 304, 286, 274, 143, 142, 116 and 115. IR (CHCl$_3$) 3562, 1609, 1599, 1583 cm$^{-1}$. $^1$-NMR(CDCl$_3$, 300 MHz)delta(ppm): 2.0 (m, 1H), 2.33 (m, 1H), 2.7 (m, 1H), 2.93 (m, 1H), 4.71 (ddd, J=3.02, 3.02, 8.44 Hz, ArOCH), 4.87 (s, OCH), 5.39 (s, OCH$_2$), 6.9-7.1 (m, 5ArH), 7.15-7.35 (m, 3ArH), 7.54 (dd, J=8, 8 Hz, ArH), 7.7 (m, 2ArH), 7.83 (d, J=8 Hz, ArH), 8.08 (d, J=8 Hz, ArH) and 8.19 (d, J=8 Hz, ArH).

Analysis calculated for C$_{26}$H$_{23}$NO$_3$: C, 78.57; H, 5.83; N, 3.52%. Found: C, 78.30; H, 5.82; N, 3.33%.

trans-isomer. $^1$-NMR(CDCl$_3$, 300 MHz)delta(ppm): 1.85 (m, 1H), 2.22 (m, 1H), 2.82 (m, 2H), 4.44 (ddd, J=2.77, 6.85, 9.82 Hz, ArOCH), 4.84 (d, J=7 Hz, OCH), 5.35 (s, OCH$_2$), 6.8-7.1 (m, 5ArH), 7.24 (m, 3ArH), 7.50 (dd, J=8, 8 Hz, ArH), 7.65 (m, 2ArH), 7.78 (d, J=8 Hz, ArH), 8.04 (d, J=8 Hz, ArH) and 8.14 (d, J=8 Hz, ArH).

EXAMPLE 160

3(2H)-Benzylidene-6-methoxy-1-(p-toluenesulfonyl)-4(1H)-quinolinone

By the method of Example 146, 25.0 g (75.5 mmol) of 6-methoxy-1-(p-toluenesulfonyl)-2,3-dihydro-4(1H)quinolinone (J. Am. Chem. Soc., Vol. 71, p. 1901, 1949) and 12.0 g (113 mmol) of benzaldehyde were converted to 20.0 g (63%) of present title product recrystallized from ether-hexane, m.p. 131°-132° C.

MS (m/e) 419 (M+), 264 and 221. IR (CHCl$_3$) 1672, 1599, 1569 cm$^{-1}$. $^1$-NMR(CDCl$_3$)delta(ppm): 2.32 (s, ArCH$_3$), 3.83 (s, OCH$_3$), 5.05 (d, J=2H, CH$_2$), 7.0-7.6 (m, 10ArH, vinyl H) and 7.75 (d, J=8 Hz, ArH).

Analysis calculated for C$_{24}$H$_{21}$NO$_4$S: C, 68.72; H, 5.05; N, 3.34%. Found: C, 68.85; H, 4.98; N, 3.17%.

EXAMPLE 161

6-Methoxy-1-(p-toluenesulfonyl)-3-benzyl-2,3-dihydro-4(1H)-quinolinone

By the method of Example 147, 19.9 g (47.4 mmol) of the title product of the preceding Example was converted to 13.8 g (69%) of present title compound, m.p. 101°-103° C.

MS (m/e) 421 (M+), 266 and 91. IR (CHCl$_3$) 1683, 1604 cm$^{-1}$. $^1$-NMR(CDCl$_3$, 300 MHz)delta(ppm): 2.2-2.5 (m, 2H), 2.38 (s, ArCH$_3$), 3.28 (dd, J=15, 2 Hz, 1H), 3.56 (dd, J=13, 12 Hz, 1H), 3.62 (s, OCH$_3$), 4.24 (dd, J=15, 5 Hz, 1H), 7.0 (m, 2ArH), 7.11 (m, 2ArH), 7.25 (m, 6ArH), 7.39 (d, J=2 Hz, ArH) and 7.77 (d, J=8 Hz, Analysis calculated for C$_{24}$H$_{23}$NO$_4$S: C, 68.39; H, 5.50; N, 3.32%. Found: C, 68.52; H, 5.51; N, 3.28%.

EXAMPLE 162

6-Methoxy-3-benzyl-2,3-dihydro-4(1H)-quinolinone

A mixture of 9.71 g (23.1 mmol) of the title product of the preceding Example in 78 ml acetic acid and 48 ml concentrated hydrochloric acid was refluxed for 8 hours. The reaction was added to 1 liter ice and water and the precipitate collected by filtration to yield 6.2 g (100%) of present title compound, m.p. 108°-111° C.

MS (m/e) 267 (M+), 190, 176 and 91. IR (KBr) 1638 cm$^{-1}$. $^1$H-NMR(CDCl$_3$)delta(ppm): 2.4-3.5 (m, 5H), 3.73 (s, OCH$_3$), 6.64 (d, J=8 Hz, ArH), 6.96 (d, J=2 Hz, ArH) and 7.3 (m, 6ArH).

EXAMPLE 163

6-Hydroxy-3-benzyl-2,3-dihydro-4(1H)-quinolinone

By the method of Example 137, 6.16 g (23.0 mmol) of the title product of the preceding Example was converted to 2.52 g (43%) of the title compound, m.p. 143°-149° C.

MS (m/e) 253 (M+), 176, 162 and 91. IR (KBr) 1640 cm$^{-1}$. $^1$H-NMR(DMSO-d$_6$ 300 MHz)delta(ppm): 2.5-2.7 (m, 2H), 2.9-3.3 (m, 3H), 6.25 (s, NH), 6.64 (d, J=8 Hz, ArH), 6.84 (dd, J=8, 2 Hz, ArH), 7.01 (d, J=2 Hz, ArH), 7.25 (m, 5ArH) and 8.81 (s, OH).

Analysis calculated for C$_{16}$H$_{15}$NO$_2$: C, 75.87; H, 5.97; N, 5.53%. Found C, 75.61; H, 5.94; N, 5.37%.

EXAMPLE 164

6-Hydroxy-1-(p-tolu-enesulfonyl)-3-benzyl-2,3-dihydro-4(1H)-quinolinone

To a solution of 2.19 g (8.66 mmol) of the title product of the preceding Example in 13 ml pyridine was added (gradually) 1.65 g (8.66 mmol) of p-toluenesulfonyl chloride. The reaction was stirred 1 hour and then added to 200 ml 1N hydrochloric acid. The quenched mixture was extracted with ethyl acetate, and the organic extract washed with 1N HCl and saturated NaCl, dried over MgSO$_4$, evaporated and the residue triturated with ether-hexane to give 2.88 g (82%) of present title compound, recrystallized from ether, m.p. 200°-205° C.

MS (m/e) 407 (M+), 252 and 91. IR (KBr) 1687, 1604 cm$^{-1}$. $^1$H-NMR(CDCl$_3$+DMSO-d$_6$, 300 MHz)delta(ppm): 2.1-2.3 (m, 2H), 2.32 (s, ArCH$_3$), 3.20 (m, 1H), 3.47 (t, J=12 Hz, 1H), 4.15 (dd, J=14, 4 Hz, 1H), 6.8-7.3 (m, 11ArH), 7.61 (d, J=8 Hz, ArH) and 8.96 (s, OH).

Analysis calculated for C$_{23}$H$_{21}$NO$_5$S.$\frac{1}{4}$H$_2$O: C, 66.33; H, 5.32; N, 3.36%. Found: C, 66.57; H, 5.29; N, 3.30%.

EXAMPLE 165

1-p-Toluenesulfonyl)-3-benzyl-6-(2-quinolyl)methoxy-2,3-dihydro-4(1H)-quinolinone A mixture of 2.88 g (7.08 mmol) of the title product of the preceding Example, 1.38 g (7.79 mmol) 2-chloromethylquinoline, 2.93 g (21.2 mmol) of anhydrous K$_2$CO$_3$ and 1.17 g (7.79 mmol) NaI in 7 ml acetone was heated at reflux for 20 hours. The reaction was cooled, filtered and the filtrate evaporated. Crystallization from ether-hexane gave 2.19 g (56%) of present title compound, m.p. 165°-175° C.

MS (m/e) 548 (M+), 393, 154, 142, 115 and 91. IR (KBr) 1687, 1604 cm$^{-1}$. $^1$H-NMR(CDCl$_3$, 300 MHz)delta(ppm) 2.2-2.5 (m, 2H), 2.39 (s, ArCH$_3$), 3.29 (dd, J=15, 2 Hz, 1H), 3.57 (t, J=15 Hz, 1H), 4.25 (dd, J=15, 5 Hz, 1H), 5.40 (s, OCH$_2$), 7.03, 7.12 (m, 4ArH), 7.3 (m, 6ArH), 7.57 (m, 2ArH), 7.65 (d, J=8 Hz, ArH), 7.74 (dd, J=8, 8 Hz, ArH), 7.82 (m, 2ArH), 8.08 (d, J=8 Hz, ArH) and 8.21 (d, J=8 Hz, ArH).

EXAMPLE 166

3-Benzyl-6-(2-quinolyl)methoxy)-2,3-dihydro-4(1H)-quinolinone

A mixture of 2.05 g (3.74 mmol) of title product of the preceding Example, 13 ml of acetic acid, 8 ml concentrated hydrochloric acid and 2 ml water was heated at reflux for 9 hours. The reaction was added to 250 ml ice and water, adjusted to pH 6 with 6N NaOH (about 45 ml) and then adjusted to pH 8 by addition of solid NaHCO$_3$. This mixture was extracted with CH$_2$Cl$_2$ and the extract dried over MgSO$_4$, evaporated and the residue triturated with ether to yield 850 mg (58%) of present title compound, m.p. 174°–176° C.

MS (m/e) 394 (M+), 252, 143, 115 and 91. $^1$H-NMR(DMSO-d$_6$), 300 MHz)delta(ppm): 2.62 (m, 1H), 2.9–3.2 (m, 3H), 3.29 (m, 1H), 5.27 (s, OCH$_2$), 6.51 (s, NH), 6.74 (d, J=8 Hz, ArH), 7.1–7.3 (m, 9ArH), 7.6 (m, 2ArH), 7.76 (dd, J=8, 8 Hz, ArH), 7.98 (m, 2ArH) and 8.37 (d, J=8 Hz, ArH).

EXAMPLE 167 cis- and trans-3-Benzyl-6-(2-quinolyl)methoxy-1,2,3,4-tetrahydro-4-quinolinol

By the method of Example 139, 810 mg (2.06 mmol) of the title product of the preceding Example was converted to present title compound. Purification via column chromatography on 300 g of silica gel eluted cis-title product, m.p. 163°–164° C., and 260 mg (32%) of the trans-title product, m.p. 152°–153° C., both recrystallized from CH$_2$Cl$_2$/diisopropyl ether.

cis-isomer. MS (m/e) 396 (M+), 254, 143, 117 and 91. IR (CHCl$_3$) 1616, 1600, 1560 cm$^{-1}$. $^1$H-NMR(DMSO-d$_6$, 300 MHz)delta(ppm): 1.86 (m, 1H), 2.8 (m, 2H), 2.98 (m, 1H), 3.3 (m, 1H covered by H$_2$O peak), 4.26 (bs, OH), 4.97 (d, J=5 Hz, OCH), 5.19 (s, OCH$_2$), 5.46 (s, NH), 6.38 (d, J=8 Hz, ArH), 6.75 (m, 2ArH), 7.1–7.4 (m, 6ArH), 7.6 (m, 2ArH), 7.75 (dd, J=8, 8 Hz, ArH), 7.97 (dd, J=8, 8 Hz, ArH) and 8.36 (d, J=8 Hz, ArH).

Analysis calculated for C$_{26}$H$_{22}$N$_2$O$_2$.¼H$_2$O: C, 78.27; H, 5.68; N, 7.02% Found: C, 78.35; H, 6.25; N, 6.92%.

trans-isomer. MS (m/e) 396 (M+), 254, 143, 117 and 91. IR (CHCl$_3$) 1619, 1601, 1561 cm$^{-1}$. $^1$H-NMR(DMSO-d$_6$, 300 MHz)delta(ppm): 1.92 (m, 1H), 2.31 (dd, J=12, 10 Hz, 1H), 2.67 (dd, J=15, 6 Hz, 1H), 2.78 (m, 1H), 3.09 (m, 1H), 4.18 (t, J=6 Hz, OCH, with D$_2$O: d, J=5.8 Hz), 5.15 (d, J=6 Hz, OH), 5.26 (s, OCH$_2$), 5.46 (s, NH), 6.44 (d, J=8 Hz, ArH), 6.76 (bd, J=8 Hz, ArH), 6.92 (bs, ArH), 7.1–7.3 (m, 5ArH), 7.63 (dd, J=8, 8 Hz, ArH), 7.69 (d, J=8 Hz, ArH), 7.80 (dd, J=8, 8 Hz, ArH), 8.02 (m, 2ArH), and 8.22 (d, J=8 Hz, ArH).

Analysis calculated for C$_{26}$H$_{22}$N$_2$O$_2$.¼H$_2$O: C, 78 27; H, 5.68; N, 7.02% Found: C, 78.32; H, 5.80; N, 6.89%.

EXAMPLE 168

3-Benzylidene-6-methoxythiochroman-4-one

By the method of Example 1, 39.9 g (0.206 mol) of 6-methoxythiochroman-4-one (Chem. Abstracts 66:46292n) and 21.8 g (0.206 mol) of benzaldehyde gave 54.8 g (95%) of present title compound, m.p. 124°–126° C.

MS (m/e) 282 (M+), 265, 253, 194, 177, 166 151, 138, 122 and 115. IR (CHCl$_3$) 1661, 1594 cm$^{-1}$. $^1$H-NMR(CDCl$_3$)delta(ppm): 3.85 (s, OCH$_3$), 4.05 (d, J=1.5 Hz, CH$_2$), 6.92 (dd, J=8, 2 Hz, ArH), 7.1–7.4 (m, 6ArH), 7.63 (d, J=2 Hz, ArH) and 7.70 (bs, vinyl H).

EXAMPLE 169

3-Benzyl-6-methoxythiochroman-4-one

By the method of Example 2, except to use methanol as solvent, 52.0 g (0.184 mol) of the title product of the preceding Example gave 39.8 g (76%) of present title compound, recrystallized from CH$_2$Cl$_2$/diisopropyl ether, m.p. 66°–68° C.

MS (m/e) 284 (M+), 251, 229, 193, 180, 166 150, 138, 123 and 91. IR (CHCl$_3$) 1669, 1600 cm$^{-1}$. $^1$H-NMR(CDCl$_3$)delta(ppm): 2.6–3.5 (m, 5H), 3.89 (s, OCH$_3$), 6.97 (dd, J=8, 2 Hz, ArH), 7.08 (bs, ArH), 7.28 (m, 5ArH) and 7.62 (d, J=2 Hz, ArH).

EXAMPLE 170

3-Benzyl-6-hydroxythiochroman-4-one

By the method of Example 3, 39.8 g (0.140 mol) of the title product of the preceding Example gave 37.1 g (98%) of present title compound, m.p. 73°–77° C.

MS (m/e) 270 (M+), 251, 237, 179, 166 153, 152, 124, 115 and 91. IR (KBr) 1662, 1594, 1579, 1552 cm$^{-1}$. $^1$H-NMR(CDCl$_3$+DMSO-d$_6$)delta(ppm): 2.5–3.5 (m, 5H), 6.9–7.4 (m, 7ArH), and 7.52 (d, J=2 Hz, ArH).

EXAMPLE 171

3-Benzyl-6-(2-quinolyl)methoxythiochroman-4-one

By the method of Example 55, 36.0 g (0.133 mol) of the title product of the preceding Example and 26.0 g (0.147 mol) of 2-chloromethylquinoline gave 20.0 g (37%) of present title compound, recrystallized from CH$_2$Cl$_2$/diisopropyl ether, m.p. 127°–130° C.

MS (m/e) 411 (M+) 320, 142, 117, 116, 115 and 91. IR (CHCl$_3$) 1669, 1598 cm$^{-1}$. $^1$H-NMR(CDCl$_3$, 300 MHz)delta(ppm): 2.74–2.91 (m, 2H), 2.96 (m, 1H), 3.07 (dd, J=12, 3 Hz, 1H), 3.28 (dd, J=15, 4 Hz, 1H), 5.35 (s, OCH$_2$), 7.06–7.32 (m, 7ArH), 7.50 (dd, J=8, 8 Hz, ArH), 7.60 (d, J=8 Hz, ArH), 7.69 (dd, J=8, 8 Hz, ArH), 7.78 (m, 2ArH), 8.05 (d, J=8 Hz, ArH), and 8.14 (d, J=8 Hz, ArH).

Analysis calculated for C$_{26}$H$_{21}$NO$_2$S: C, 75.89; H, 5.14, N, 3.40% Found: C, 75.72; H, 5.12; N, 3.33%.

EXAMPLE 172 cis- and trans-3-Benzyl-6-(2-quinolyl)methoxythiochroman-4-ol

By the methods of Example 4, 2.91 g (7.08 mmol) of the title product of the preceding Example gave in order of elution 1.45 g (50%) of the cis-isomer, recrystallized from ether/hexane, m.p. 93°–108° C. and 1.13 g (39%) of the trans-isomer, recrystallized from CH$_2$Cl$_2$/diisopropyl ether, m.p. 128° C.

cis-isomer. MS (m/e) 413 (M+) 322, 277, 215, 182, 143, 142, 117, 116, 115 and 91. IR (KBr) 1618, 1599, 1568 cm$^{-1}$. $^1$H-NMR(CDCl$_3$, 300 MHz)delta(ppm): 2.2 (m, 1H), 2.61 (dd, J=12, 2 Hz, 1H), 2.72 (dd, J=14, 8 Hz, 1H), 2.92 (dd, J=14, 8 Hz, 1H), 3.10 (t, J=12 Hz, 1H), 4.46 (s, OCH), 5.26 (s, OCH$_2$), 6.82 (dd, J=8, 2 Hz, ArH), 6.89 (s, ArH), 6.98 (d, J=8 Hz, ArH), 7.1–7.3 (m, 5ArH), 7.50 (dd, J=8, 8 Hz, ArH), 7.56 (d, J=8 Hz, ArH), 7.68 (dd, J=8, 8 Hz, ArH), 7.77 (d, J=8 Hz, ArH), 8.01 (d, J=8 Hz, Ar) and 8.12 (d, J=8 Hz, ArH).

Analysis calculated for $C_{26}H_{23}NO_2S$: C, 75.52; H, 5.61; N, 3.39% Found: C, 75.63; H, 5.53; N, 3.26%.

trans-isomer. MS (m/e) 413 (M+) 271, 143, 142, 117, 116, 115 and 91. IR (KBr) 1617, 1598, 1565 cm$^{-1}$. $^1$H-NMR(CDCl$_3$, 300 MHz)delta(ppm): 2.35–2.7 (m, 4H), 3.34 (dd, J=15, 3 Hz, 1H), 4.43 (d, J=4 Hz, OCH), 5.31 (s, OCH$_2$), 6.88 (dd, J=8, 2 Hz, ArH), 7.00 (d, J=2 Hz, ArH), 7.05 (d, J=8 Hz, ArH), 7.1–7.3 (m, 5ArH), 7.52 (dd, J=8, 8 Hz, ArH), 7.62 (d, J=8 Hz, ArH), 7.68 (dd, J=8, 8 Hz, ArH), 7.80 (d, J=8 Hz, ArH), 8.05 (d, J=8 Hz, ArH) and 8.16 (d, J=8 Hz, ArH).

Analysis calculated as for cis-isomer: Found: C, 75.63; H, 5.53; N, 3.26%.

EXAMPLE 173 cis- and trans-3-Benzyl-6-(2-quinolyl)methoxythiochroman-4-one-1-oxide and

3-Benzyl-6-(2-quinolyl)methoxythiochroman-4-one-1,1-dioxide

To a −5° to 0° C. solution of 12.0 g (29.2 mmol) of the title product of Example 171 in 100 ml CH$_2$Cl$_2$ was slowly added a solution of 3-chloroperbenzoic acid (8.02 g, 46.6 mmol) in 50 ml CH$_2$Cl$_2$. The reaction mixture was added to additional CH$_2$Cl$_2$ and saturated NaHCO$_3$, and the organic layer separated, dried over MgSO$_4$ and evaporated to a solid, which was purified via column chromatography on 1 Kg of silica gel eluted with CH$_2$Cl$_2$ and ether to give in order of elution 650 mg (5%) of 1,1-dioxide, 1.16 g (9.3%) of cis-1-oxide and 6.56 g (52.6%) of trans-1-oxide.

1,1-dioxide, recrystallized from CH$_2$Cl$_2$/diisopropyl ether, m.p. 177°–178° C. MS (m/e) 443 (M+), 143, 142, 117, 116, 115 and 91. IR (CHCl$_3$) 1695, 1619, 1590, 1571 cm$^{-1}$. $^1$H-NMR(CDCl$_3$, 300 MHz)delta(ppm): 2.92 (dd, J=14, 10 Hz, 1H), 3.4 (m, 2H), 3.52 (dd, J=14, 5 Hz, 1H), 3.72 (m, 1H), 5.48 (s, OCH$_2$), 7.17 (m, 2ArH), 7.25 (m, 3ArH), 7.39 (dd, J=8, 2 Hz, ArH), 7.58 (m, 2ArH), 7.76 (m, 2ArH), 7.83 (d, J=8 Hz, ArH), 7.89 (d, J=8 Hz, ArH), 8.09 (d, J-8 Hz, ArH) and 8.21 (d, J=8 Hz, ArH).

Analysis calculated for $C_{26}H_{21}NO_4S$: C, 70.41; H, 4.77; N, 3.16%. Found: C, 70.19; H, 4.93; N, 3.10%.

trans-1-oxide, recrystallized from CH$_2$Cl$_2$/diisopropyl ether, m.p. 176°–179° C. MS (m/e) 427 (M+), 143, 142, 117, 116, 115 and 91. IR (KBr) 1684 cm$^{-1}$. $^1$H-NMR(CDCl$_3$, 300 MHz)delta(ppm): 2.8–3.1 (m, 3H), 3.48 (dd, J=12, 2 Hz, 1H), 3.56 (dd, J=12, 3 Hz, 1H), 5.45 (s, OCH$_2$), 7.1–7.35 (m, 6ArH), 7.42 (dd, J=8, 2 Hz, ArH), 7.54 (dd, J=8, 8 Hz, ArH), 7.60 (d, J=8 Hz, ArH), 7.73 (ddd, J=8, 8, 1.5 Hz, ArH), 7.8 (m, 2ArH), 8.07 (d, J=8 Hz, ArH) and 8.19 (d, J=8 Hz, ArH).

Analysis calculated for $C_{26}H_{21}NO_3S$: C, 73.05; H, 4.95; N, 3.28%. Found: C, 72.98; H, 5.21; N, 3.25%.

cis-1-oxide, recrystallized from CH$_2$Cl$_2$/diisopropyl propyl ether, m.p. 149°–151° C. MS (m/e) 427 (M+), 411, 410, 143, 142, 115, 105 and 91. IR (CHCl$_3$) 1693, 1588, 1567 cm$^{-1}$. $^1$H-NMR(CDCl$_3$, 300 MHz)delta(ppm): 2.8–3.1 (m, 2H), 3.35 (dd, J=12, 3 Hz, 1H), 3.49 (dd, J=15, 5 Hz, 1H), 4.02 (m, 1H), 5.48 (s, OCH$_2$), 7.1–7.9 (m, 12ArH), 8.08 (dd, J=8 Hz, ArH), and 8.20 (d, J=8 Hz, ArH).

Analysis calculated as for cis-isomer: Found: C, 73.25; H, 5.18; N, 3.26%.

EXAMPLE 174 trans-3-Benzyl-6-(2-quinolyl)methoxythiochroman-4-ol-1,1-dioxide

To a 0° C. solution of 400 mg (0.903 mmol) of the 1,1-dioxide title product of the preceding Example in 6 ml methanol, 2 ml tetrahydrofuran and 2 ml CH$_2$Cl$_2$ was added 25 mg (0.657 mmol) of sodium borohydride. After minutes, the reaction was diluted with 2 ml water and the precipitate which formed collected by filtration. Drying of the solid in vacuo gave 391 mg (97%) of present title compound, m.p. 190°–191° C.

MS (m/e) 445 (M+), 354, 263, 143, 142, 115, 105 and 91. IR (CHCl$_3$) 3573, 3390, 1597, 1571 cm$^{-1}$. $^1$H-NMR(DMSO-d$_6$+CDCl$_3$)delta(ppm): 2.25 (dd, J=14, 11 Hz, 1H), 2.42 (m, 1H), 2.46 (dd, J=13, 10 Hz, 1H), 2.8 (dd, J=12, 4 Hz, 1H), 2.99 (dd, J=14, 5 Hz, ArH), 4.09 (t, J=8 Hz, OCH; with D$_2$O: d, J=9.23 Hz), 5.04 (s, OCH$_2$), 5.49 (d, J=8 Hz, OH), 6.69 (dd, J=8, 2 Hz, ArH), 6.75–6.95 (m, 5ArH), 7.07 (d, J=2 Hz, ArH), 7.1–7.4 (m, 4ArH), 7.46 (d, J=8 Hz, ArH), 7.63 (d, J=8 Hz, ArH) and 7.84 (d, J=8 Hz, ArH).

Analysis calculated for $C_{26}H_{23}NO_4S \cdot \frac{1}{4}H_2O$: C, 69.39; H, 5.26; N, 3.11% Found: C, 69.58; H, 5.01; N, 3.08%.

EXAMPLE 175 r-3-Benzyl-6-(2-quinolyl)methoxythiochroman-t-4-ol-t-1-oxide (For comment re nomenclature, refer to Example 99).

By the method of the preceding Example without isolation of the t-3-benzyl-r-4-ol isomer, 2.00 g (4.68 mmol) of trans-1-oxide title product of Example 173 was converted to 1.45 g (72%) of present title compound, m.p. 213°–215° C.

MS (m/e) 429 (M+), 412, 312, 311, 294, 143, 142, 117, 116, 115 and 91. $^1$H-NMR(CDCl$_3$, 300 MHz)delta(ppm): 2.41 (dd, J=14, 10 Hz, 1H), 2.61 (dd, J=13, 8 Hz, ArH), 3.05 (m, 2H), 3.25 (dd, J=14, 5 Hz, 1H), 4.25 (d, J=9 Hz, OH), 4.39 (dd, J=9, 7 Hz, OCH; with D$_2$O: d, J=7.26 Hz), 6.98 (dd, J=8, 2 Hz, ArH), 7.1–7.3 (m, 5ArH), 7.36 (d, J=2 Hz, ArH), 7.5–7.6 (m, 3ArH), 7.71 (ddd, J=8, 8, 1.5 Hz, ArH), 7.79 (d, J=8 Hz, ArH), 8.05 (d, J=8 Hz, ArH) and 8.15 (d, J=8 Hz, ArH).

Analysis calculated for $C_{26}H_{23}NO_3S$: C, 72.70; H, 5.40; N, 3.26% Found C, 72.55; H, 5.42; N 3 23%.

EXAMPLE 176 r-3-Benzyl-6-(2-quinolyl)methoxythio chroman-c- and t-4-ol-c-1-oxide (For comment re nomenclature, refer to Example 99).

To a 10° C. mixture of 600 mg (1.41 mmol) of the cis-1-oxide title product of Example 173 in 4 ml methanol, 2 ml tetrahydrofuran and 4 ml CH$_2$Cl$_2$ was added 54 mg (1.42 mmol) of sodium borohydride. After 15 minutes the reaction solution was diluted with H$_2$O and added to additional CH$_2$Cl$_2$ and saturated NaCl. The organic layer was separated over Na$_2$SO$_4$ and evaporated to an oil, which was crystallized from CH$_2$Cl$_2$ and diisopropyl ether to give 554 mg (92%) of present title compound as a 2:1 mixture of title trans-4-ol-1-oxide:cis-4-ol-1-oxide, m.p. 133°–140° C.

MS (m/e) 429 (M+), 412, 294, 143, 142, 117, 116, and 91. IR (CHCl$_3$) 3575, 3350, 1597 and 1572 cm$^{-1}$. $^1$H-NMR(CDCl$_3$+D$_2$O, 300 MHz)delta(ppm): 4.50 (d, J=2.64 Hz, cis-(1,4) OCH) and 4.79 (d, J=7.85 Hz, trans-(1,4) OCH).

Analysis calculated for $C_{26}H_{23}NO_3S \cdot \frac{1}{4}H_2O$: C, 71.95; H, 5.46; N, 3.23%
Found: C, 71.98; H, 5.11; N, 3.13%.

EXAMPLE 177

3-Benzylidene-6-methoxy-4-chromanone

By the method of Example 1, 20.0 g (0.112 mol) 6-methoxy-4-chromanone and 11.9 g (0.112 mol) benzaldehyde gave 25.1 g (84%) of present title compound, m.p. 118° C.

MS (m/e) 266 (M+), 151, 150, 115 and 107. IR (CHCl$_3$) 1668, 1610 cm$^{-1}$. $^1$H-NMR(CDCl$_3$)delta(ppm): 3.85 (s, OCH$_3$), 5.29 (d, J=2 Hz, CH$_2$), 6.86 (d, J=8 Hz, ArH), 7.00 (d, J=2 Hz, ArH), 7.1-7.5 (m, 6ArH) and 7.83 (t, J=2 Hz, vinyl H).

Analysis calculated for $C_{17}H_{14}O_3$: C, 76.68; H, 5.30%. Found: C, 76.64; H, 5.08%.

EXAMPLE 178

3-Benzyl-6-methoxy-4-chromanone

By the method of Example 2, using CH$_3$OH as solvent, 6.85 g (25.8 mmol) of the title product of the preceding Example was converted to 6.04 g (88%) of present title compound, m.p. 71°-72° C.

MS (m/e) 268 (M+), 237, 177, 150, 107 and 91. IR (CHCl$_3$) 1682, 1617, 1586 cm$^{-1}$. $^1$H-NMR(CDCl$_3$)delta(ppm): 2.6-3.4 (m, 3H), 3.83 (s, OCH$_3$), 4.2 (m, CH$_2$), 6.80 (d, J=8 Hz, ArH), 6.98 (d, J=2 Hz, ArH) and 7.2 (m, 6ArH).

Analysis calculated for $C_{17}H_{16}O_3$: C, 76.10; H, 6.01%. Found: C, 76.31; H, 5.90%.

EXAMPLE 179

3-Benzyl-6-hydroxy-4-chromanone

By the method of Example 3, 5.50 g (20.5 mmol) of the title product of the preceding Example was converted to 5.11 g (98%) of present title compound, m.p. 140°-143° C.

$^1$H-NMR(CDCl$_3$)delta(ppm): 2.6-3.6 (m, 3H), 4.3 (m, CH$_2$), 6.35 (bs, OH), 6.82 (d, J=8 Hz, ArH), 7.15 (dd, J=8, 2 Hz, ArH), 7.3 (m, 5ArH) and 7.51 (d, J=2 Hz, ArH).

EXAMPLE 180

3-Benzyl-6-(2-quinolyl)methoxy-4-chromanone

By the method of Example 138, 4.96 g (19.5 mmol) of title product of the preceding Example and 4.18 g (19.5 mmol) of 2-chloromethylquinoline hydrochloride gave 2.58 g (33%) of present title compound.

$^1$H-NMR(CDCl$_3$)delta(ppm): 2.66 (dd, J=15, 12 Hz, 1H), 2.86 (8 line m, 1H), 3.24 (dd, J=14, 4 Hz, 1H), 4.10 (dd, J=14, 10 Hz, 1H), 4.29 (dd, J=14, 10 Hz, 1H), 5.34 (s OCH$_2$), 6.89 (d, J=8 Hz, ArH), 7.25 (m, 8ArH), 7.53 (m, 2ArH), 7.62 (d, J=8 Hz, ArH), 7.70 (dd, J=8, 8 Hz, ArH), 7.80 (d, J=8 Hz, ArH), 8.07 (d, J=8 Hz, ArH) and 8.17 (d, J=8 Hz, ArH).

EXAMPLE 181 cis- and trans-3-Benzyl-6-(2-quinolyl)methoxy-4-chromanol

By the method of Example 139, 2.58 g (6.53 mmol) of title product of the preceding Example gave in order of elution (on 150 g silica gel with 66% ether-hexane as eluant), and after recrystallization from CH$_2$Cl$_2$/diisopropyl ether, 853 mg (33%) of the cis-isomer, m.p. 107°-108° C., and 710 mg (27%) of the trans-isomer, m.p. 148°-149° C.

cis-isomer. MS (m/e) 397 (M+), 261, 142, 115 and 91. IR (CHCl$_3$) 1619, 1601, 1566 cm$^{-1}$. $^1$H-NMR(CDCl$_3$, 300 MHz)delta(ppm): 1.99 (d, J=6 Hz, OH), 2.28 (m, CH), 2.63 (dd, J=13, 7 Hz, 1H), 2.86 (dd, J=13, 7 Hz, 1H), 4.02 (d, J=9 Hz, 1H), 4.45 (dd, J=8, 4 Hz, OCH), 5.26 (s, OCH$_2$), 6.75 (d, J=8 Hz, ArH), 6.87 (m, 2ArH), 7.25 (m, 5ArH), 7.52 (m, ArH), 7.60 (d, J=8 Hz, ArH), 7.70 (dd, J=8, 8 Hz, ArH), 7.80 (d, J=8 Hz, ArH), 8.04 (d, J=8 Hz, ArH) and 8.14 (d, J=8 Hz, ArH).

Analysis calculated for $C_{26}H_{23}NO_3$: C, 78.57; H, 5.38; N, 3.52% Found: C, 78.61; H, 5.80; N, 3.47%.

trans-isomer. MS (m/e) 397 (M+), 255, 142, 115 and 91. IR (CHCl$_3$) 1619, 1601, 1566 cm$^{-1}$. $^1$H-NMR(CDCl$_3$, 300 MHz)delta(ppm): 2.05 (d, J=6 Hz, OH), 2.18 (m, 1H), 2.52 (dd, J=14, 10 Hz, 1H), 2.70 (dd, J=14, 6 Hz, 1H), 3.93 (dd, J=13, 4 Hz, 1H), 4.16 (dd, J=12, 2 Hz, 1H), 4.43 (bt, OCH), 5.32 (s, OCH$_3$), 6.80 (d, J=8 Hz, ArH), 6.92 (dd, J=8, 2 Hz, ArH), 7.00 (d, J=2 Hz, ArH), 7.1-7.3 (m, 5ArH), 7.54 (dd, J=8, 8 Hz, ArH), 7.66 (d, J=8 Hz, ArH), 7.72 (dd, J=8, 8 Hz, ArH), 7.82 (d, J=8 Hz, ArH), 8.06 (d, J=8 Hz, ArH) and 8.18 (d, J=8 Hz, ArH).

Analysis calculated for $C_{26}H_{23}NO_3$: C, 78.57; H, 5.38; N, 3.52%. Found: C, 78.54; H, 5.76; N, 3.47%.

EXAMPLE 182

3-Benzyl-6-(2-pyridyl)methoxy-4-chromanone

By the method of Example 138, 5.00 g (19.7 mmol) of the title product of Example 179 and 4.84 g (29.5 mmol) of 2-chloromethylpyridine hydrochloride gave 5.6 g (82%) of present title compound.

EXAMPLE 183 cis- and trans-3-Benzyl-6-(2-pyridyl)methoxy-4-chromanol

By the method of Example 139, 5.60 g (16.2 mmol) of title product of the preceding Example gave, in order of elution (600 g silica gel, eluted with ether) and after recrystallization from ether-hexane, 3.59 g (54%) of the cis-isomer, m.p. 125° C., and 1.97 g (35%) of the trans-isomer, m.p. 126°-127° C.

cis-isomer. MS (m/e) 347 (M+), 255, 209, 191, 167, 137, 117 and 91. IR (CHCl$_3$) 3653, 3340, 1595, 1574 cm$^{-1}$. $^1$H-NMR(CDCl$_3$, 300 MHz)delta(ppm): 2.29 (m, 1H), 2.85 (dd, J=13, 7 Hz, 1H), 2.87 (dd, J=13, 7 Hz, 1H), 4.03 (d, J=7 Hz, CH$_2$), 4.47 (d, J=3 Hz, OCH), 5.10 (s, OCH$_2$), 6.75 (d, J=8 Hz, ArH), 6.83 (m, 2ArH), 7.1-7.4 (m, 6ArH), 7.47 (d, J=8 Hz, ArH), 7.69 (dd, J=8, 8 Hz, ArH) and 8.53 (d, J=5 Hz, ArH).

Analysis calculated for $C_{22}H_{21}NO_3$: C, 76.06; H, 6.09; N, 4.03% Found C, 75.87; H, 6.32; N, 4.12%.

trans-isomer. MS (m/e) 347 (M+), 255, 211, 191, 167, 117 and 91. IR (CHCl$_3$) 3583, 3376, 1595, 1573 cm$^{-1}$. $^1$H-NMR(CDCl$_3$, 300 MHz)delta(ppm): 2.19 (m, 1H), 2.52 (dd, J=14, 9 Hz, 1H), 2.72 (dd, J=14, 7 Hz, 1H), 3.90 (dd, J=12, 6 Hz, 1H), 4.16 (dd, J=12, 2 Hz, 1H), 4.43 (d, J=5 Hz, OCH), 5.14 (s, OCH$_3$), 6.78 (d, J=8 Hz, ArH), 6.90 (dd, J=8, 2 Hz, ArH) 6.95 (d, J=2 Hz, ArH), 7.1-7.4 (m, 6ArH), 7.51 (d, J=8 Hz, ArH), 7.71 (dd, J=8, 8 Hz, ArH) and 8.54 (d, J=5 Hz, ArH).

Analysis calculated for $C_{22}H_{21}NO_3$: C, 76.06; H, 6.09; N, 4.03% Found: C, 75.93; H, 6.31; N, 4.30%.

EXAMPLE 184 trans-3-Benzyl-6-(2-pyridyl)methoxy-4-chromanol Hydrochloride

By the method of Example 118, 800 mg (2.31 mmol) of title product of the preceding Example gave 841 mg (95%) of present title compound, crystallized from ethanol-ether, m.p. 138°-140° C.

MS (m/e) 347 (M+-HCl), 255, 211, 191, 137, and 91. IR (KBr) 3355, 1615, 1527, 1491 cm$^{-1}$. $^1$H-NMR(DMSO-d$_6$, 300 MHz)delta(ppm): 2.10 (m, 1H), 2.44 (dd, J=14, 8 Hz, 1H), 2.77 (dd, J=14, 6 Hz, 1H), 3.84 (dd, J=12, 6 Hz, 1H), 4.05 (dd, J=12, 2 Hz, 1H), 4.30 (d, J=6 Hz, OCH), 5.38 (s, OCH$_3$), 6.76 (d, J=8 Hz, ArH), 6.93 (dd, J=8, 2 Hz, ArH) 7.08 (d, J=2 Hz, ArH), 7.1-7.4 (m, ArH), 7.82 (dd, J=8 Hz, ArH), 7.94 (d, J=8 Hz, ArH), 8.36 (dd, J=8, 8 Hz, ArH) and 8.82 (d, J=5 Hz, ArH).

Analysis calculated for C$_{22}$H$_{22}$ClNO$_3$.H$_2$O: C, 65.75; H, 6.02; N, 3.49% Found: C, 65.58; H, 6.14; N, 3.05%.

EXAMPLE 185

6-Hydroxy-3-[3,4-(methylenedioxy)benzylidene]-4-chromanone

By the method of Example 1, 5.7 g (34.8 mmol) of 6-hydroxy-4-chromanone and 5.21 g (34.8 mmol) of piperonol gave 9.21 g (90%) of present title compound, tlc (60% ether-hexane) Rf 0.30.

$^1$H-NMR(DMSO-d$_6$)delta(ppm): 5.33 (d, J=2 Hz, CH$_2$), 6.10 (s, OCH$_2$O), 7.0 (m, 5ArH), 7.15 (m, ArH) and 7.61 (t, J=2 Hz, vinyl H).

EXAMPLE 186

6-Hydroxy-3-[3,4-(methylenedioxy)benzyl]-4-chromanone

By the method of Example 2, 9.00 g (30.4 mmol) of the title product of the preceding Example gave 7.15 g (79%) of present title compound, tlc (60% ether-hexane) Rf 0.38.

$^1$H-NMR(CDCl$_3$+DMSO-d$_6$)delta(ppm): 2.3-3.3 (m, 3H), 3.9-4.5 (m, 2H), 5.96 (s, OCH$_2$O) and 6.6-7.6 (m, 6ArH).

EXAMPLE 187

3-[3,4-(Methylenedioxy)benzyl]-6-(2-quinolyl)methoxy-4-chromanone

By the method of Example 138, 6.90 g (23.1 mmol) of title product of the preceding Example and 4.96 g (23.1 mmol) of 2-chloromethylquinoline hydrochloride gave 5.40 g (53%) of present title compound, tlc (10% ether-dichloromethane), Rf 0.39.

$^1$H-NMR(DMSO-d$_6$)delta(ppm): 2.55 (m, 1H), 3.0 (m, 2H), 4.08 (dd, J=12, 12 Hz, 1H), 4.27 (dd, J=12, 5 Hz, 1H), 5.35 (s, OCH$_2$), 5.97 (s, OCH$_2$O), 6.62 (d, J=8 Hz, ArH), 6.78 (m, 2ArH), 6.98 (d, J=8 Hz, ArH), 7.30 (m, 2ArH), 7.60 (m, 2ArH), 7.76 (dd, J=8, 8 Hz, ArH), 7.98 (m, 2ArH) and 8.38 (d, J=8 Hz, ArH).

EXAMPLE 188 cis- and trans-3-[3,4-(Methylenedioxy)benzyl]-6-(2-quinolyl)methoxy-4-chromanol

By the method of Example 139, 3.92 g (8.92 mmol) of title product of the preceding Example gave in order of elution (on 400 g silica gel, eluted with 25% ethyl acetate-dichloromethane) and after recrystallization from dichloromethane-diisopropylether, 1.91 g (49%) of the cis-isomer, m.p. 140°-143° C., and 1.16 g (30%) of the trans-isomer, m.p. 153°-155° C.

cis-isomer. MS (m/e) 441 (M+), 281, 261, 251, 160, 142, 135 and 115. IR (CHCl$_3$) 3590, 3355, 1619, 1601, 1566 cm$^{-1}$. $^1$H-NMR(CDCl$_3$, 300 MHz)delta(ppm): 1.85 (d, J=6 Hz, OH), 2.17 (m, 1H), 2.51 (dd, J=14, 7 Hz, 1H), 2.71 (dd, J=13, 8 Hz, 1H), 3.97 (d, J=8 Hz, 2H), 4.41 (bt, OCH; with D$_2$D, O: J=3.37 Hz), 5.24 (s, OCH$_2$), 5.89 (s, OCH$_2$O), 6.65 (m, 4ArH), 6.83 (m, 2ArH), 7.48 (dd, J=8, 8 Hz, ArH), 7.57 (d, J=8 Hz, ArH), 7.67 (dd, J=8, 8 Hz, ArH) 7.76 (d, J=8 Hz, ArH), 8.00 (d, J=8 Hz, ArH) and 8.11 (d, J=8 Hz, ArH).

Analysis calculated for C$_{27}$H$_{23}$NO$_5$: C, 73.46; H, 5.25; N, 3.17% Found: C, 73.73; H, 5.15; N, 3.12%.

trans-isomer. MS (m/e) 141 (M+), 281, 261, 251, 160, 143, 142, 135 and 115. IR (CHCl$_3$) 3590, 3355, 1619, 1601, 1566 cm$^{-1}$. $^1$H-NMR(CDCl$_3$, 300 MHz)delta(ppm): 2.08 (m, 1H), 2.40 (dd, J=15, 11 Hz, 1H), 2.58 (dd, J=14, 6 Hz, 1H), 3.87 (dd, J=12, 5 Hz, 1H), 4.12 (dd, J=11, 2 Hz, 1H), 4.38 (bt, OCH; With D$_2$O: d, J=3.96 Hz), 5.28 (s, OCH$_2$), 5.89 (s, OCH$_2$O), 6.54 d, J=8 Hz, ArH), 6.62 (d, J=2 Hz, ArH), 6.67 (d, J=8 Hz, ArH), 6.75 (d, J=8 Hz, ArH), 6.89 (dd, J=8, 2 Hz, ArH), 6.95 (d, J=2 Hz, ArH), 7.50 (dd, J=8, 8 Hz, ArH), 7.62 (d, J=8 Hz, ArH), 7.66 (dd, J=8, 8 Hz, ArH), 7.68 (d, J=8 Hz, ArH), 8.02 (d, J=8 Hz, ArH) and 8.14 (d, J=8 Hz, ArH).

Analysis calculated for C$_{27}$H$_{23}$NO$_5$: C, 73.46; H, 5.25; N, 3.17% Found: C, 73.89; H, 5.08; N, 3.16%.

EXAMPLE 189

6-Hydroxy-3-(3,4-dimethoxybenzylidene)-4-chromanone

By the method of Example 1, 5.00 g (30.5 mmol) of 6-hydroxy-4-chromanone and 5.06 g (30.5 mmol) of veratraldehyde gave 4.29 g (45%) of present title compound, tlc (66% ether-hexane) Rf 0.13.

EXAMPLE 190 trans-6-Hydroxy-3-(3,4-dimethoxybenzyl)-4-chromanol

To a 0° C. suspension of 1.20 g (33.6 mmol) of lithium aluminum hydride in 26 ml tetrahydrofuran was added (slowly) a suspension of 4.19 g (13.4 mmol) of title product of the preceding Example in 30 ml tetrahydrofuran. The reaction mixture was heated to reflux for 30 minutes, then cooled to 0° C. and quenched with water. The quenched reaction was acidified with 60 ml 10% sulfuric acid and extracted with ether. The organic extract was dried over MgSO$_4$ and evaporated. The crude product was purified via column chromatography on 400 g of silica gel eluted with 50% ethyl acetate/CH$_2$Cl$_2$ to yield (after crystallization from dichloromethane-isopropyl ether) 900 mg (21%) of present title compound, m.p. 165°-166° C.

MS (m/e) 316 (M+), 152, 137, 121 and 107. IR (KBr) 1593, 1515, 1495 cm$^{-1}$. $^1$H-NMR(CDCl$_3$+DMSO-d$_6$)delta(ppm): 2.05 (m, 1H), 2.34 (dd, J=15, 10 Hz, 1H), 2.59 (dd, J=15, 6 Hz, 1H), 3.45 (d, J=6 Hz, OH), 3.76 (s, 2OCH$_3$), 4.05 (dd, J=12, 2 Hz, 1H), 4.26 (t, J=6 Hz, OCH), 6.5-6.8 (m, 6ArH) and 7.91 (s, OH).

Analysis calculated for C$_{18}$H$_{20}$O$_5$.½H$_2$O. C, 67.86; H, 6.41% Found: C, 67.81; H, 6.37%.

EXAMPLE 191 trans-3-(3,4-Dimethoxybenzyl)-6-(2-quinolyl)methoxy-4-chromanol

By the method of Example 138, 700 mg (2.22 mmol) of the title product of the preceding Example and 711 mg (3.32 mmol) of 2-chloromethylquinoline hydrochloride gave 700 mg (69%) of present title compound, recrystallized from ethyl acetate-ether, m.p. 175° C.

MS (m/e) 457 (M+), 306, 261, 176, 152, 151, 144, 143 and 115 IR (KBr) 1617, 1599, 1570 cm$^{-1}$. $^1$H-NMR(DMSO-d$_6$, 300 MHz)delta(ppm): 2.00 (m, 1H), 2.29 (dd, J=14, 9 Hz, 1H), 2.61 (dd, J=14, 6, 1H), 3.70 (s, 2OCH$_3$), 3.77 (dd, J=12, 6 Hz, 1H), 3.99 (dd, J=12, 2 Hz, 1H), 4.19 (bs, OCH), 5.28 (s, OCH$_2$), 5.43 (bs, OH), 6.57 (d, J=8 Hz, ArH), 6.66 (d, J=8 Hz, ArH), 6.72 (bs, ArH), 6.78 (d, J=8 Hz, ArH), 6.85 (dd, J=8, 2 Hz, ArH), 6.99 (d, J=2 Hz, ArH), 7.57 (dd, J=8, 8 Hz, ArH), 7.62 (d, J=8 Hz, ArH), 7.74 (dd, J=8, 8 Hz, ArH), 7.96 (m, ArH) and 8.37 (d, J=8 Hz, ArH).

Analysis calculated for C$_{28}$H$_{27}$NO$_5$: C, 73.51; H, 5.95; N, 3.06%. Found: C, 73.28; H, 5.92; N, 2.92%.

EXAMPLE 192

3S,4R- and 3R,4S-3-Benzyl-6-(2-quinolyl)methoxy-4-chromanyl R-O-Acetylmandelate

By the method of Example 6, 19.97 g (50.30 mol) of the trans-title product of Example 181 and 11.71 g (60.36 mol) of (R)-(−)-O-Acetylmandelic acid gave in order of elution (2.7 kg silica gel, eluted with 10% ether-toluene) and after recrystallization from dichloromethane-ether 10.87 g (37.7%) of the 3S,4R-diastereomer, m.p. 142°-145° C., and 5.97 g (20.7%) of the 3R,4S-diastereomer. The absolute configuration of these diastereoisomers was determined by X-ray crystallography.

3S,4R-diastereoisomer: MS (m/e) 573 (M+), 396, 380, 288, 261, 237, 142 and 91. IR (CHCl$_3$) 1740, 1612, 1599 cm$^{-1}$. $^1$H-NMR(CDCl$_3$, 300 MHz)delta(ppm): 2.16 (s, CH$_3$CO), 2.33 (m, 1H), 2.47 (dd, J=12, 10 Hz, 1H), 2.71 (dd, J=12, 6 Hz, 1H), 3.90 (dd, J=12, 3 Hz, 1H), 4.05 (dd, J=12, 2 Hz, 1H), 5.04 (d, J=14 Hz, 1H), 5.11 (d, J=14 Hz, 1H), 5.63 (d, J=3 Hz, OCH), 5.81 (s, CH), 6.52 (d, J=2 Hz, ArH), 6.74 (d, J=8 Hz, ArH), 6.87 (dd, J=8, 2 Hz, ArH), 7.1-7.45 (m, 10ArH), 7.51 (dd, J=8, 8 Hz, ArH), 7.57 (d, J=8 Hz, ArH), 7.70 (dd, J=8, 8 Hz, ArH), 7.80 (d, J=8 Hz, ArH), 8.05 (d, J=8 Hz, ArH) and 8.15 (d, J=8 Hz, ArH). [alpha]$_D^{20}$= +0.69° (acetone, c=0.0116)

Analysis calculated for C$_{36}$H$_{31}$NO$_6$: C, 75.38; H, 5.45; N, 2.44%. Found: C, 75.54; H, 5.47; N, 2.45%.

3R,4S-diastereoisomer: MS (m/e) 573 (M+), 380, 288, 260, 237, 142 and 91. IR (CHCl$_3$) 1740, 1599 cm$^{-1}$. $^1$H-NMR(CDCl$_3$, 300 MHz)delta(ppm): 1.99 (m, 1H), 2.18 (s, CH$_3$CO), 2.37 (dd, J=12, 10 Hz, 1H), 2.53 (dd, J=12, 6 Hz, 1H), 3.76 (d, J=3.29 Hz, CH$_2$), 5.28 (s, OCH$_2$), 5.68 (d, J=3 Hz, OCH), 5.87 (s, CH), 6.77 (d, J=8 Hz, ArH), 6.90 (d, J=2 Hz, ArH), 6.94 (dd, J=8, 2 Hz, ArH), 7.01 (d, J=8 Hz, ArH), 7.1-7.45 (m, 9ArH), 7.51 (dd, J=8, 8 Hz, ArH), 7.7 (m, 2H), 7.80 (d, J=8 Hz, ArH), 8.06 (d, J=8 Hz, ArH) and 8.18 (d, J=8 Hz, ArH). [alpha]$_D^{20}$= −41.65° (acetone, c=0.0121)

Analysis calculated for C$_{36}$H$_{31}$NO$_6$: C, 75.38; H, 5.45; N, 2.44%. Found: C, 75.13; H, 5.51; N, 2.39%.

EXAMPLE 193

3S-Benzyl-6-(2-quinolyl)methoxy-4R-chromanol

By the method of Example 7, the 3S,4R-diastereomer of the preceding Example gave 6.42 g (87%) of the title compound, recrystallized from CH$_2$Cl$_2$-diisopropyl ether, m.p. 137°-138° C.

MS, IR and $^1$H-NMR were identical to those of the racemic trans-title product of Example 181, and of the 3R,4S-enantiomer of the next Example. [alpha]$_D^{20}$= +21.6° (methanol, c=0.0101)

Analysis calculated for C$_{26}$H$_{23}$NO$_3$: C, 78.57; H, 5.38; N, 3.52%. Found: C, 78.19; H, 5.74; N, 3.50%.

EXAMPLE 194

3R-Benzyl-6-(2-quinolyl)methoxy-4S-chromanol

By the method of Example 7, 5.91 g (10.3 mmol) of the 3R,4S-diastereomer of Example 192 gave 3.76 g (92%) of present title compound, recrystallized from CH$_2$Cl$_2$-diisopropyl ether, m.p. 138° C.

MS, IR and $^1$H-NMR were identical to those of the racemic trans-title product of Example 181, and of the 3S,4R-enantiomer of the preceding Example. [alpha]$_D^{20}$= −21.9° (methanol, c=0.0122)

Analysis calculated for C$_{26}$H$_{23}$NO$_3$: C, 78.57; H, 5.38; N, 3.52%. Found: C, 78.32; H, 5.75; N, 3.47%.

By the methods of Examples 192-194, the title products of Examples 47, 48 and 50 were resolved into enantiomeric cis- and trans-3-(3-methoxycarbonylbenzyl)-6-(2-quinolyl)methoxy-4-chromanols and cis-3-(3-methoxycarbonylbenzyl)-6-(5-fluoro-2-benzothiazolyl)methoxy-4-chromanol which in turn were hydrolyzed to the corresponding enantiomeric acids: cis-3-(3-carboxybenzyl)-6-(2-quinolyl)methoxy-4-chromanol, m.p. 181°-181.5° C., [alpha]$_D^{25}$= +10.9° (tetrahydrofuran); trans-(+)-3-(3-carboxybenzyl)-6-(2-quinolyl)methoxy-4-chromanol, m.p. 208°-210° C., [alpha]$_D^{25}$= +2.4° (tetrahydrofuran); cis-(+)-3R-(3-carboxybenzyl)-6-(5-fluoro-2-benzothiazolyl)methoxy-4R-chromanol, m.p. 186°-188° C., [alpha]$_D^{25}$= +86.4° (tetrahydrofuran).

EXAMPLE 195

3-Benzyl-6-(2-quinolyl)methoxy-4-chromanyl 4-Piperidinobutyrate Dihydrochloride

To a 0° C. mixture of 980 mg (8.04 mmol) 4-(N,N-dimethylamino)pyridine, 1.25 g (6.04 mmol) of 4-piperidinobutyric acid hydrochloride and 2.00 g (5.04 mmol) of the trans-title product of Example 181 in 10 ml of dichloromethane was added 1.14 g (5.54 mmol) of dicyclohexyl carbodiimide. The resultant mixture was stirred for 15 hours at 25° C. and then filtered. The filtrate was evaporated and the residue purified via column chromatography on 150 g of silica gel eluted with 10% methanol-dichloromethane to give an oil. This oil was dissolved in ethanol and acidified with 10.1 ml of 1N hydrochloric acid. The solvent was removed on a rotating evaporator and the residue crystallized from dichloromethane-diisopropyl ether to give 2.97 g (95%) of present title compound, m.p. 145°-150° C. $^1$H-NMR(CDCl$_3$, 300 MHz)delta(ppm): 1.25 (m,), 1.8 (m), 2.22 (m), 2.38 (m), 2.47 (dd, J=14, 9 Hz, 1H), 2.60 (dd, J=12, 6 Hz, 1H), 2.81 (m), 2.9-3.2 (m), 3.46 (m), 3.99 (dd, J=12, 2 Hz, 1H), 4.04 (dd, J=12, 2 Hz, 1H), 5.64 (d, J=3 Hz, OCH), 5.76 (d, J=20 Hz, 1H), 5.82 (d, J=20 Hz, 1H), 6.81 (d, J=8 Hz, ArH), 6.96 (m, 2ArH), 7.1-7.3 (m, 5ArH), 7.82 (dd, J=8, 8 Hz, ArH), 8.01 (dd, J=8, 8 Hz, ArH), 8.08 (d, J=8 Hz, ArH), 8.12 (d, J=8 Hz, ArH) and 8.82 (m, 2ArH).

Analysis calculated for C$_{35}$H$_{40}$Cl$_2$N$_2$O$_4$.H$_2$O: C, 65.52; H 6.60; N 4.37% Found: C, 65.69; H, 6.40; N, 4.37%.

EXAMPLE 196

3S-Benzyl-6-(2-quinolyl)methoxy-4R-chromanyl 4-Piperidinobutyrate

By the method of Example 195, 3.21 g (8.09 mmol) of the title product of Example 193 and 2.01 g (9.70 mmol) of 4-piperidinobutyric acid hydrochloride gave 4.45 g (88%) present title product as a solid.

MS (m/e) 550 (M+-2 HCl), 407, 379, 288, 237, 169, 147, 142, 115, 98 and 91. IR (CHCl$_3$) 1730, 1647, 1602 cm$^{-1}$.

Analysis calculated for C$_{35}$H$_{40}$Cl$_2$N$_2$O$_4$: C, 67.40; H, 6.46; N, 4.49%. Found: C, 67.56; H, 6.57; N, 4.40%.

[alpha]$_D^{20}$= +44.20° (methanol, c=0.0119).

EXAMPLE 197

3R-Benzyl-6-(2-quinolyl)methoxy-4S-chromanyl 4-Piperidinobutyrate

By the method of Example 195, 1.88 g (4.74 mmol) of the title product of Example 194 and 1.18 g (5.68 mmol) of 4-piperidinobutyric acid hydrochloride gave 2.68 g (91%) present title product as a solid.

MS (m/e) 550 (M+-2 HCl), 407, 379, 288, 237, 170, 169, 147, 142, 115, 98 and 91. IR (CHCl$_3$) 1730, 1646, 1602 cm$^{-1}$.

Analysis calculated for C$_{35}$H$_{40}$Cl$_2$N$_2$O$_4$: C, 67.40; H, 6.46; N, 4.49%. Found: C, 67.58; H, 6.55; N, 4.41%.

[alpha]$_D^{20}$= -43 38° (methanol, c=0.0114).

EXAMPLE 198 trans-3-Benzyl-6-(2-quinolyl)methoxy-4-chromanyl Hemisuccinate

To a solution of 1.00 g (2.52 mmol) of the trans-title product of Example 181 in 8 ml pyridine was added 277 mg (27.7 mmol) of succinic anhydride and the reaction heated at 80° C. for 12 hours. The reaction was evaporated in vacuo to an oil which crystallized upon addition of ether. Recrystallization from dichloromethane-diisopropyl ether gave 912 mg (73%) of present title product, m.p. 175°-176° C.

MS (m/e) 497 (M+), 396, 379, 362, 261, 237, 142 and 91. IR (KBr) 1731, 1703 cm$^{-1}$. $^1$H-NMR(CDCl$_3$, 300 MHz)delta(ppm): 2.30 (m, 1H), 2.4-2.8 (m, 6H), 3.83 (dd, J=12, 6 Hz, 1H), 4.00 (dd, J=12, 2 Hz, 1H), 5.29 (d, J=15 Hz, 1H), 5.22 (d, J=15 Hz, 1H), 5.75 (d, J=6 Hz, OCH), 6.70 (d, J=8 Hz, ArH), 6.84 (dd, J=8, 2 Hz, ArH), 6.94 (d, J=2 Hz, ArH), 7.1-7.3 (m, 5ArH), 7.52 dd, J=8, 8 Hz, ArH), 7.70 (m, 2ArH), 7.79 (d, J=8 Hz, ArH), 8.15 (d, J=8 Hz, ArH) and 8.21 (d, J=8 Hz, ArH).

Analysis calculated for C$_{30}$H$_{27}$NO$_6$: C, 72.42; H, 5.47; N, 2.82%. Found: C, 72.16; H, 5.43; N, 2.70%.

EXAMPLE 199 trans-3-Benzyl-6-(2-quinolyl)methoxy-4-chromanyl Hemisuccinate Ester, Sodium Salt To a solution of 300 mg (0.604 mmol) of the title product of the preceding Example in 50 ml ethanol was added 0.604 ml of 1N sodium hydroxide. The reaction solution was evaporated in vacuo and the residue triturated with ether to give a quantitative yield of present title product as a solid.

EXAMPLE 200 trans-3-Benzyl-6-(2-quinolyl)methoxy-4-chromanyl Hemisuccinate Ester, Ethanolamine Salt To a solution of 300 mg (0.604 mmol) of the title product of Example 198 in 50 ml dichloromethane was added 36.8 mg (0.604 mmol) of ethanolamine. The reaction solution was evaporated in vacuo and the residue triturated with ether to give a quantitative yield of present title product as a solid.

EXAMPLE 201

6-Methoxy-3-(2-pyridyl)methylene-4-chromanone

By the method of Example 1, 20.0 g (0.112 mol) of 6-methoxy-4-chromanone and 18.0 g (0.168 mol) of 2-pyridinecarbaldehyde gave 17.5 g (60%) of present title product, m.p. 109°-111° C.

MS (m/e) 267 (M+), and 117. IR (CHCl$_3$) 1668, 1611, 1586, 1564 cm$^{-1}$. $^1$H-NMR(CDCl$_3$, 300 MHz)delta(ppm): 3.80 (s, OCH$_3$), 5.83 (d, J=2 Hz, CH$_2$), 6.89 (d, J=8 Hz, ArH), 7.17 (dd, J=8, 2 Hz, ArH), 7.2 (m, ArH), 7.39 (d, J=2 Hz, ArH), 7.46 (d, J=8 Hz, ArH), 7.70 (m, 2ArH) and 8.67 (d, J=2 Hz, vinyl H).

Analysis calculated for C$_{16}$H$_{13}$NO$_3$: C, 71.90; H, 4.90; N, 5.24%. Found: C, 71.98; H, 4.90; N, 5.22%.

EXAMPLE 202

6-Methoxy-3-(2-pyridylmethyl)-4-chromanone

By the method of Example 2, 154 g (0.577 mol) of title product of the preceding Example gave 128 g (82%) of present title product, m.p. 112°-114° C.

MS (m/e) 269 (M+), 254, 177, 118, 107 and 93. IR (KBR) 1684, 1641, 1620, 1588, 1565 cm$^{-1}$. $^1$H-NMR(CDCl$_3$, 300 MHz)delta(ppm): 2.82 (dd, J=14, 9 Hz, 1H), 3.29 (m, 1H), 3.39 (dd, J=14, 4 Hz, 1H), 3.74 (s, OCH$_3$), 4.17 (dd, J=10, 9 Hz, 1H), 4.45 (dd, J=11, 5 Hz, 1H), 6.84 (d, J=8 Hz, ArH), 7.02 (dd, J=8, 2 Hz, ArH), 7.08 (dd, J=8, 8 Hz, ArH), 7.18 (dd, J=8, 2 Hz), 7.27 (d, J=2 Hz, ArH), 7.56 (ddd, J=8, 8, 2 Hz, ArH) and 8.47 (d, J=5 Hz, ArH).

Analysis calculated for C$_{16}$H$_{15}$NO$_3$: C, 71.13; H, 5.57; N, 5.12%. Found: C, 71.36; H, 5.61; N, 5.12%.

EXAMPLE 203

6-Hydroxy-3-(2-pyridylmethyl)-4-chromanone

By the method of Example 3, 128 g (0.474 mol) of the title product of the preceding Example gave 104 g (86%) of present title product, crystallized from ethyl acetate, m.p. 150°-151° C.

MS (m/e) 255 (M+), 163, 137, 118, 117 and 93. IR (KBR) 1691, 1645, 1616, 1599, 1566 cm$^{-1}$. $^1$H-NMR(DMSO-d$_6$)delta(ppm): 2.81 (dd, J=16, 10 Hz, 1H), 3.2-3.3 (m, 2H and H20), 4.20 (t, J=12 Hz, 1H), 4.36 (dd, J=12, 4 Hz, 1H), 6.88 (d, J=8 Hz, ArH), 7.01 (dd, J=8, 2 Hz, ArH), 7.10 (d, J=2 Hz, ArH), 7.22 (dd, J=8, 8 Hz, ArH), 7.31 (d, J=8 Hz, ArH), 7.72 (dd, J=8, 8 Hz, ArH), 8.47 (d, J=5 Hz, ArH) and 9.50 (bs, OH).

EXAMPLE 204 cis- and trans-6-Hydroxy-3-(2-pyridylmethyl)-4-chromanol

By the method of Example 4, 11.5 g (45.1 mmol) of the title product of the preceding Example gave a crude mixture of isomers. This mixture was purified and the isomers separated via column chromatography on 830 g of silica gel eluted with 10% isopropanol-60% ethyl acetate-30% dichloromethane chromatography to give, in order of elution, 4.27 g (31%) or cis-isomer, m.p. 153°-155° C. and 5.50 g (40%) of trans-isomer, m.p. 146°-147° C.

cis-isomer. MS (m/e) 257 (M+), 240, 147, 118 and 93 IR (KBr) 1617, 1599, 1569 cm$^{-1}$. $^1$H-NMR(DMSO-d6)delta(ppm): 2.41 (m, 1H), 2.68 (m, 1H), 2.96 (dd, J=14, 6 Hz, 1H), 3.91 (m, 2H), 4.35 (bs, OCH), 5.36 (d, J=7 Hz, OH), 6.6 (m, 3ArH), 7.22 (m, ArH), 7.31 (d, J=8 Hz, ArH), 7.72 (dd, J=8, 8 Hz, ArH), 8.48 (bs, ArH) and 8.81 (s, OH).

Analysis calculated for $C_{15}H_{15}NO_3$: C, 70.02; H, 5.88; N, 5.44%. Found: C, 69,86; H, 5.82; N, 5.33%.

trans-isomer. MS (m/e) 257 (M+), 240, 118 and 93. IR (KBr) 1613, 1595, 1570 cm$^{-1}$. $^1$H-NMR(DMSO-d)delta(ppm): 2.32 (m, 1H), 2.61 (dd, J=13, 8 Hz, 1H), 2.88 (dd, J=13, 5 Hz, 1H), 3.82 (dd, J=12, 6 Hz, 1H), 4.07 (dd, J=12, 2 Hz, 1H), 4.25 (t, J=6 Hz, OCH; with D20 d, J=6 Hz), 5.47 (d, J=6 Hz, OH), 6.58 (bs, 2ArH), 7.75 (bs, ArH), 7.24 (d, J=8 Hz, ArH), 7.72 (dd, J=8, 8 Hz, ArH), 8.51 (d, J=4 Hz, ArH) and 8.84 (s, OH).

Analysis calculated for $C_{15}H_{15}NO_3 \cdot \frac{1}{8}H_2O$: C, 69.42; H, 5.92; N, 5.40%. Found: C, 69.61; H, 5.86; N, 5.35%.

EXAMPLE 205 cis-3-(2-Pyridylmethyl)-6-(2-quinolyl)methoxy-4-chromanol

By the method of Example 5, 5.00 g (19.5 mmol) of the cis-title product of the preceding Example and 3.54 g (20.0 mmol) of 2-chloromethylquinoline gave 4.41 g (57%) of present title product, recrystallized from $CH_2Cl_2$-diisopropyl ether, m.p. 115°-118° C.

MS (m/e) 398 (M+), 306, 288, 256, 142, 118 and 93. IR (KBr) 1618, 1594, 1566 cm$^{-1}$. $^1$H-NMR(CDCl$_3$ 300, MHz)delta(ppm): 2.38 (m, 1H), 2.84 (dd, J=15, 5 Hz, 1H), 3.00 (dd, J=12, 11 Hz, 1H), 4.07 (m, 2H), 4.38 (d, J=3 Hz, OCH, with D$_2$O: d, J=3.63 Hz), 5.32 (s, OCH$_2$), 5.38 (bs, OH), 6.78 (d, J=8 Hz, ArH), 6.88 (dd, J=8, 2 Hz, ArH), 7.01 (d, J=2 Hz, ArH), 7.2 (m, 3H), 7.52 (dd, J=8, 8 Hz, ArH), 7.65 (m, 3ArH), 7.81 (d, J=8 Hz, ArH), 8.05 (d, J=8 Hz, ArH), 8.16 (d, J=8 Hz, ArH) and 8.54 (d, J=5 Hz, ArH).

Analysis calculated for $C_{25}H_{22}N_2O_3$: C, 75.36; H, 5.56; N, 7.03%. Found: C, 75.30; H, 5.52; N, 6.98%.

EXAMPLE 206 trans-3-(2-Pyridylmethyl)-6-2-quinolyl)methoxy-4-chromanone

By the method of Example 5, 4.00 g (15.6 mmol) of the trans-title product of Example 204 and 2.89 g (16.3 mmol) of 2-chloromethylquinoline gave 3.80 g (61%) of present title product, also crystallized from $CH_2Cl_2$-diisopropyl ether, m.p. 121°-123° C.

MS (m/e) 306, 288, 256, 144, 118 and 93. IR (KBr) 1658, 1619, 1589 cm$^{-1}$. $^1$H-NMR(CDCl +D$_2$O, 300 MHz)delta(ppm): 2.27 (m, 1H), 2.75 (dd, J=13, 6 Hz, 1H), 2.94 (dd, J=13, 7 Hz, 1H), 3.89 (dd, J=12, 6 Hz, 1H), 4.20 (dd, J=12, 2 Hz, 1H), 4.56 (d, J=6.26 Hz, OCH), 5.30 (s, OCH$_2$), 6.74 (d, J=8 Hz, ArH), 6.87 (dd, J=8, 2 Hz, ArH), 7.12 (m, 3ArH), 7.5-7.9 (m, 5ArH), 8.45 (d, J=8 Hz, ArH), 8.15 (d, J=8 Hz, ArH) and 8.44 (d, J=5 Hz, ArH).

Analysis calculated for $C_{25}H_{22}N_2O_3$: C, 75.36; H, 5.56; N, 7.03%. Found: C 75.11; H 5.64; N 6 95%

EXAMPLE 207 cis- and trans-6-(2-pyridyl)methoxy-3-(2-pyridylmethyl)-4-chromanol

By the method of Example 78, 10.0 g (38.9 mmol) of a mixture of the title products of Example 204 and 5.08 g (39.9 mmol) of 2-picolyl chloride gave, in order of elution (360 g silica gel eluted with 50% acetonedichloromethane as eluant), 3.30 g (24%) of cis-isomer, m.p. 85°-95° C., and 5.69 g (42%) of trans-isomer, m.p. 103°-104° C., both recrystallized from $CH_2Cl_2$-diisopropyl ether.

cis-isomer. MS (m/e) 348 (M+), 256, 238, 119, 118, 93 and 92. IR (CHCl$_3$) 3262, 1595, 1571 cm$^{-1}$. $^1$H-NMR(CDCl$_3$, 300 MHz)delta(ppm): 2.37 (m, 1H); 2.83 (dd, J=12, 5, 1H), 2.99 (dd, J=12, 11 Hz, 1H), 4.05 (m, 2H), 4.38 (d, J=4 Hz, OCH), 5.11 (s, OCH$_2$), 5.36 (bs, OH), 6.73 (d, J=8 Hz, ArH), 6.82 (dd, J=8, 2 Hz, ArH), 6.93 (d, J=2 Hz, ArH), 7.2 (m, 3ArH), 7.46 (d, J=8 Hz, ArH), 7.63 (m, 2ArH) and 8.52 (m, 2ArH).

Analysis calculated for $C_{21}H_{20}N_2O_3 \cdot \frac{3}{4}H_2O$: C, 69.69; H, 5.99; N, 7.74%. Found: C, 69.89; H, 5.69; N, 7.88%.

trans-isomer. MS (m/e) 348 (M+), 331, 256, 238, 118 and 93. IR (CHCl$_3$) 3200, 1595, 1571 cm$^{-1}$. $^1$H-NMR(CDCl$_3$, 300 MHz)delta(ppm): 2.47 (m, 1H), 2.79 (dd, J=15, 6 Hz, 1H), 2.95 (dd, J=13, 6 Hz, 1H), 3.92 (dd, J=11, 9 Hz, 1H), 4.21 (dd, J=11, 3 Hz, 1H), 4.59 (d, J=6 Hz, OCH), 4.98 (bs, OH), 5.14 (s, OCH$_2$), 6.73 (d, J=8 Hz, ArH), 6.82 (dd, J=8, 2 Hz, ArH), 7.15 (m, ArH), 7.49 (d, J=8 Hz, ArH), 7.60 ddd, J=8, 8, 2 Hz, ArH), 7.68 (ddd, J=8, 8, 2 Hz, ArH), 8.48 (d, J=6 Hz, ArH) and 8.54 (d, J=6 Hz, ArH).

Analysis calculated for $C_{21}H_{20}N_2O_3$: C, 72.40; H, 5.79; N, 8.04%. Found: C, 72.41; H, 5.52; N, 8.05%.

EXAMPLE 208

3R,4S- and 3S,4R-3-(2-Pyridylmethyl)-6-(2-quinolyl)methoxy-4-chromanyl R-O-Acetylmandelate By the method of Example 192, 4.78 g (12.0 mmol) of the title product of Example 206 and 3.20 g (16.5 mmol) of (R)-(−)-O-acetylmandelic acid gave in order of elution (from 1.2 kg silica gel eluted with 33% ethyl acetate-dichloromethane) and after crystallization from $CH_2Cl_2$-diisopropyl ether, 980 mg (14%) of 3R,4S-diastereomer, m.p. 97°-102° C., and 1.64 g (24%) of 3S,4R-diastereomer, m.p. 109°-110° C.

3R,4S-diastereomer. $^1$H-NMR(CDCl$_3$, 300 MHz)delta(ppm): 2.18 (s, CH$_3$CO), 2.33 (m, 1H), 2.64 (m, 2H), 3.85 (m, 2H), 5.28 (s, OCH$_2$), 5.72 (d, J=4 Hz, OCH), 5.87 (s, CH), 6.78 (d, J=8 Hz, ArH), 6.9 (m, 3ArH), 7.07 (dd, J=8, 8 Hz, ArH), 7.35 (m, 6ArH), 7.51 (dd, J=8, 8 Hz, ArH), 7.68 (m, 2ArH), 7.80 (d, J=8 Hz, ArH), 8.05 (d, J=8 Hz, ArH), 8.18 (d, J=8 Hz, ArH) and 8.48 (d, J=5 Hz, ArH).

3S,4R-diastereomer. $^1$H-NMR(CDCl$_3$, 300, MHz)delta(ppm): 2.17 (s, CH$_3$CO), 2.65 (bs, OH), 2.75 (dd, J=9, 9 Hz, 1H), 2.87 (dd, J=12, 6 Hz, 1H), 3.97 (dd, J=12, 3 Hz, 1H), 5.04 (d, J=14 Hz, 1H), 5.11 (d, J=14 Hz, 1H), 5.71 (d, J=4 Hz, OCH), 5.85 (s, CH), 6.55 (d, J=2 Hz, ArH), 6.73 (d, J=8 Hz, ArH), 6.87 (dd, J=8, 2 Hz, ArH), 7.09 (m, 2ArH), 7.25 (m, 3ArH), 7.38 (m, ArH), 7.55 (m, 3ArH), 7.71 (dd, J=8, 8 Hz, ArH), 7.81 (d, J=8 Hz, ArH), 8.07 (d, J=8 Hz, ArH), 8.17 (d, J=8 Hz, ArH) and 8.52 (d, J=4 Hz, ArH).

EXAMPLE 209

3R-(2-Pyridylmethyl)-6-(2-quinolyl)methoxy-4S-chromanol

By the method of Example 7, 949 mg (1.64 mmol) of S,3R-diastereomer of the preceding Example gave 470 mg (72%) of present title product, recrystallized from $CH_2Cl_2$-diisopropyl ether, m.p. 142°–143° C.

MS, IR and $^1$H-NMR are identical to those of the racemic trans-product of Example 206.

Analysis calculated for $C_{25}H_{22}N_2O_3 \cdot \frac{1}{4}H_2O$: C, 74.52; H, 5.63; N, 6.95% Found: C, 74.68; H, 5.54; N, 6.96%. $[alpha]_D^{20} = -18.51°$ (methanol, 0.01345).

EXAMPLE 210

3S-(2-Pyridylmethyl)-6-(2-quinolyl)methoxy-4R-chromanol

By the method of Example 7, 1.60 g (2.78 mmol) of S,4R-diastereomer of Example 208 gave 900 mg (82%) of present title product, recrystallized from $CH_2Cl_2$-diisopropyl ether, m.p. 142°–143° C.

MS, IR and $^1$H-NMR are identical to those of the racemic trans-product of Example 206.

Analysis calculated for $C_{25}H_{22}N_2O_3 \cdot \frac{1}{4}H_2O$: C, 74.52; H, 5.63; N, 6.95% Found: C, 74.71; H, 5.58; N, 6.98%. $[alpha]_D^{20} = +17.74°$ (methanol, 0.0155).

EXAMPLE 211 cis-3-(3-Pyridylmethyl)-6-(2-quinolyl)methoxy-4-chromanol Dihydrochloride

By the method of Example 184, cis-3-(3-pyridylmethyl)-6-(2-quinolyl)methoxy-4-chromanol (1.00 g, 2.51 mmol) was converted to 830 mg (70%) of the title dihydrochloride salt, crystallized from a mixture of ethanol, ether and water, m.p. 110° C. (dec.).

Analysis calculated for $C_{25}H_{24}Cl_2N_2O_2 \cdot 2H_2O$: C, 59.18; H, 5.56; N, 5.52% Found: C, 59.04; H, 5.32; N, 5.44%.

EXAMPLE 212 trans-3-(3-Pyridylmethyl)-6-(2-quinolyl)methoxy-4-chromanol Dihydrochloride

By the method of Example 184, trans-title product of Example 4 (560 mg, 1.41 mmol) was converted to mg (87%) of the title dihydrochloride, crystallized from acetone, ethanol and ether, m.p. 197° C.

Analysis calculated for $C_{25}H_{24}Cl_2N_2O_3 \cdot \frac{1}{4}H_2O$: C, 63.10; H, 5.19; N, 5.89% Found: C, 63.24; H, 5.16; N, 5.85%.

EXAMPLE 213

3-[4-(Ethoxycarbonyl and methoxycarbonyl)-2-pyridyl]methylene-6-(2-quinolyl)-methoxy-4-chromanone By the method of Example 1, 12.1 g (39.7 mmol) of the title product of Example 55 and 7.10 g (39.7 mmol) of 4-carboethoxy-2-pyridinecarbaldehyde gave 11.8 g (64%) of present title products, a mixture of methyl and ethyl esters. $^1$H-NMR(CDCl ) includes delta 1.40 (t, J=6, $CH_3CH_2$), 4.39 (q, J=6, $CH_3CH_2$), 3.95 (s, $CH_3$). $^1$H-NMR(CDCl$_3$, 300 MHz)delta(ppm): 1.40 (t, $\overline{J}=6$ Hz, CH$_3$), 3.95 (s, OCH$_3$), 4.39 (q, J=6, OCH$_2$ of ethyl ester), 5.36 (s, OCH$_2$), 5.81 (d, J=2 Hz, CH$_2$), 6.91 (d, J=8 Hz, ArH), 2.2 (m, 2ArH), 7.4–7.8 (m, 5ArH), 7.98 (bs, vinyl H), 8.05 (d, J=8 Hz, ArH), 8.15 (d, J=8 Hz, ArH) and 8.79 (d, J=5 Hz, ArH).

EXAMPLE 214

3-[4-(Ethoxycarbonyl and methoxycarbonyl)-2pyridyl]methyl-6-(2-quinolyl)methoxychromanone By the method of Example 2, 11.8 g (25.3 mmol) of the title product of the preceding Example in tetrahydrofuran gave 11.7 g (99%) of present title products as a mixture of ethyl and methyl esters.

$^1$H-NMR(CDCl$_3$, 300 MHz)delta(ppm): 1.35 (t, J=6 Hz, CH$_3$), 2.87 (dd, J=15, 10 Hz, 1H), 3.31 (m, 1H), 3.46 (m, 1H), 3.89 (s, OCH$_3$), 4.16 (t, J=11 Hz, 1H), 4.34 (q, J=6 Hz, OCH$_2$ of ester), 4.43 (dd, J=11, 5 Hz, 1H), 5.29 (s, OCH$_2$), 6.85 (d, J=8 Hz, ArH), 7.15 (m, ArH), 7.4–7.8 (m, 7ArH), 8.01 (d, J=8 Hz, ArH), 8.11 (d, J=8 Hz, ArH) and 8.59 (d, J=5 Hz, ArH).

EXAMPLE 215 cis- and trans-3-[4-(Hydroxymethyl)-2-pyridyl]methyl-6-(2-quinolyl)methoxy-4-chromanol By the method of Example 190, using sufficient LiAlH$_4$ to reduce both the ketone and ester groups, 11.7 g (25.0 mmol) of the title product of the preceding Example gave in order of elution (using 650 g silica gel eluted with acetone) 1.98 g (19%) of cis-title product as a glass and 2.04 g (20%) of trans-title product, crystallized from ethyl acetate, m.p. 147°–149° C.

cis-isomer. MS (m/e) 306 (M$^+$), 286, 148, 123 and 115. IR (KBr) 1608, 1561 cm$^{-1}$. $^1$H-NMR(CDCl$_3$, 300 MHz)delta(ppm): 2.26 (m, 1H), 2.71 (dd, J=14, 6 Hz, 1H), 2.87 (dd, J=14, 10 Hz, 1H), 3.95 (m, 2H), 4.25 (d, J=4 Hz, OCH), 4.62 (s, OCH$_2$), 5.18 (s, OCH$_2$), 6.65 d, J=8 Hz, ArH), 6.77 (dd, J=8, 2 Hz, ArH), 6.94 (d, J=2 Hz, ArH), 7.06 (d, J=6 Hz, ArH), 7.16 (d, J=8 Hz, ArH), 7.44 (dd, J=8, 8 Hz, ArH), 7.54 (d, J=8 Hz, ArH), 7.62 (ddd, J=8, 8, 1.5 Hz, ArH), 7.72 (d, J=8 Hz, ArH), 7.96 (d, J=8 Hz, ArH), 8.07 (d, J=8 Hz, ArH) and 8.32 (d, J=8 Hz, ArH).

Analysis calculated for $C_{26}H_{24}N_2O_4 \cdot \frac{1}{4}H_2O$: C, 70.65; H, 5.81; N, 6.34%. Found: C, 70.49; H, 5.80; N, 5.98%.

trans-isomer. MS (m/e) 306 (M$^+$), 148, 123, 115 and 94. IR (KBr) 1602, 1557 cm$^{-1}$. $^1$H-NMR(CDCl$_3$, 300 MHz)delta(ppm): 2.39 (m, 1H), 2.72 (dd, J=15, 6 Hz, 1H), 2.88 (dd, J=14, 7 Hz, 1H), 3.85 (dd, J=10, 8 Hz, 1H), 4.14 (dd, J=12, 2 Hz, 1H), 4.51 (d, J=7 Hz, OCH), 4.66 (s, OCH$_2$), 5.24 (s, OCH$_2$), 6.67 (d, J=8 Hz, ArH), 6.80 (dd, J=8, 2 Hz, ArH), 7.05 (m, 3ArH), 7.47 (dd, J=8, 8 Hz, ArH), 7.61 (d, J=8 Hz, ArH), 7.66 (dd, J=8, 8 Hz, ArH), 7.76 (d, J=8 Hz, ArH), 8.00 (d, J=8 Hz, ArH), 8.12 (d, J=8 Hz, ArH) and 8.33 (d, J=8 Hz, ArH).

Analysis calculated for $C_{26}H_{24}N_2O_4 \cdot H_2O$: C, 69.94; H, 5.87; N, 6.27%. Found C, 70.21; H, 5.49; N, 6.23%.

EXAMPLE 216

3-Benzyl-6-(6-fluoro-2-quinolyl)methoxy-4-chromanone

By the method of Example 55, 1.00 g (3.94 mmol) of the title product of Example 179 and 847 mg (4.33 mmol) of 6-fluoro-2-chloromethylquinoline gave 1.38 g (85%) of present title product, recrystallized from $CH_2Cl_2$-diisopropyl ether, m.p. 142°–143.5° C.

MS (m/e) 413 (M$^+$), 160, 134, and 91. IR (CHCl$_3$) 1687, 1628, 1609, 1585, 1567 cm$^{-1}$. $^1$H-NMR(CDCl$_3$, 300 MHz)delta(ppm): 2.62 (dd, J=15, 12 Hz, 1H), 2.88

(8-line m, 1H), 3.26 (dd, J=14, 4 Hz, 1H), 4.11 (dd, J=11, 8 Hz, 1H), 4.31 (dd, J=10, 4 Hz, 1H), 5.33 (s, OCH$_2$), 6.91 (d, J=8 Hz, ArH), 7.25 (m, 6ArH), 7.45 (m, ArH), 7.63 (d, J=8 Hz, ArH), 8.06 (dd, J=12, 8 Hz, ArH) and 8.12 (d, J=8 Hz, ArH).

Analysis calculated for C$_{26}$H$_{20}$FNO$_3$: C, 75.53; H, 4.88; N, 3.39%. Found: C, 75.53; H, 4.33; N, 3.44%.

EXAMPLE 217 cis- and trans-3-Benzyl-6-(6-fluoro-2-quinolyl)-4-chromanol

By the method of Example 4, 1.33 g (3.22 mmol) of the title product of the preceding Example gave, in order of elution (130 g silica gel eluted with 10% ether-dichloromethane), and following recrystallization from dichloromethane-diisopropyl ether, 691 mg (52%) of cis-title product, m.p. 145°–147° C. and 444 mg (33%) of trans-title product, m.p. 154°–155° C.

EXAMPLE 218

6-Benzyloxy-3-(1-imidazolyl)methyl-4-chromanone

A solution of 3.7 g of 6-benzyloxy-3-methylene-4-chromanone and 3.7 g of imidazole in 50 cc of DMF was heated at 60° C. for 1.5 hours. The reaction was allowed to cool, then poured into water and extracted with ethyl acetate. The combined organic layers were dried over Na and evaporated to give 4 g of crude product which was purified by recrystallization from CH$_2$Cl$_2$/ether to give 3 g of title product, m.p. 108°–110° C. MS calculated for C$_{20}$H$_{18}$N$_2$O$_3$: 334.1317; found: 334.1317.

EXAMPLE 219

6-Hydroxy-3-(1-imidazolyl)methyl-4-chromanone

By the method of Example 2, 3 g of the title product of the preceding Example was converted to 2 g of present title product, tlc (9:1 CH$_2$Cl$_2$:CH$_3$OH) Rf 0.5.

EXAMPLE 220 cis- and trans-6-Hydroxy-3-1-imidazolyl)methyl-4-chromanol

By the method of Example 39, 2 g of the title product of the preceding Example was converted to a mixture of title products, 1.8 g, tlc (9:1 CH$_2$Cl$_2$:CH$_3$OH) Rf 0.15 (cis-isomer) and 0.17 (trans-isomer).

EXAMPLE 221 cis- and trans-3-(1-Imidazolyl)methyl-6-(2-quinolyl)methoxy-4-chromanol

By the method of Example 13, 1.8 g of a mixture of cis- and trans-title products of the preceding Example were converted to a mixture of present cis- and trans-products which were separated on silica gel eluting with CH$_2$Cl$_2$/MeOH. Less polar cis-isomer (680 mg) was obtained; it was recrystallized from CH$_3$OH/ethyl acetate to give 500 mg of pure cis-title product, m.p. 168° C. MS calculated for C$_{23}$H$_{21}$N$_3$O$_3$: 387.1610; found: 387.1613.

More polar trans-isomer (720 mg) was recrystallized from tetrahydrofuran and ethyl acetate to give 440 mg of pure trans-title product, m.p. 142°–144° C.

EXAMPLE 222

6-Benzyloxy-3-(3-methoxycarbonyl)benzylidene)-4-chromanone

By the method of Example 1, 6-benzyloxy-4-chromanone (2.5 g, 0.0098 mol) was converted to present title product, 5.76 g, as a gum, tlc (9:1 CH$_2$Cl$_2$:hexane) Rf 0.5.

EXAMPLE 223

6-Hydroxy-3-(3-methoxycarbonyl)benzyl-4-chromanone

Title product of the preceding Example (5.74 g) in 167 ml of tetrahydrofuran and 83 ml of ethyl acetate was hydrogenated at 50 psig for 24 hours over 2.5 g of 10% Pd/C by which time tlc (9:1 CH$_2$Cl$_2$:ethyl acetate) indicated complete conversion to the desired product. The catalyst was recovered by filtration over diatomaceous earth and the filtrate stripped to dryness to yield present title product as a yellow gum, 3.0 g, tlc (9:1 CH$_2$Cl$_2$:hexane) Rf 0.07.

EXAMPLE 224 cis- and trans-3-(3-Methoxycarbonyl)benzyl-4,6-chromandiol

Title product of the preceding Example (4.38 g, 0.014 mol) and NaBH$_4$ (0.568 g, 0.015 mol) were combined in 65 ml CH$_3$OH and stirred for 30 minutes. Silica gel was then added and the mixture evaporated to dryness, charged onto a 25 cm×10 cm silica gel column, and mixed title products eluted with 2500 ml of 49:1 CH$_2$Cl$_2$:isopropanol to yield, after stripping, the fractions, 2.2 g of present mixed title products, tlc (29:1 CH$_2$Cl$_2$:isopropanol) Rf 0.31 (cis-isomer) and 0.28 (trans-isomer).

EXAMPLE 225 cis- and trans-3-(3-Methoxycarbonyl)benzyl-6-(2-pyridyl)methoxy-4-chromanol

By the method of Example 78, the title product of the preceding Example was converted to present title products, separated by column chromatography on silica gel eluted with 33:1 CH$_2$Cl$_2$:isopropanol to yield 0.463 g of the less polar cis-isomer, tlc (3×developed with 33:1 CH$_2$Cl$_2$:isopropanol) Rf 0.4, and a mixture of the above cis-isomer with more polar trans-isomer (Rf 0.3 in the same tlc system).

The cis-isomer was further purified by column chromatography with 3:2 toluene:ethyl acetate as eluant, reducing the yield to 0.422 g.

EXAMPLE 226 cis-3-(3-Carboxybenzyl)-6-(2-pyridyl)methoxy-4-chromanol

By the method of Example 42, the cis-title product of the preceding Example (0.42 g, 0.001 mol) was converted to present title product, purified by chromatography on silica gel using 6:1 CH$_2$Cl$_2$:CH$_3$OH as eluant and recrystallization from isopropyl ether/CH$_2$Cl$_2$/hexane, 0.26 g, m.p. 196.5°–197.5° C.; MS (m/e) calculated: 391.1424, found: 391.1425.

EXAMPLE 227 cis-3-(3-Methoxyphenoxy)-6-(2-pyridyl)methoxy-4-chromanyl Dimethylglycinate Ester Dihydrochloride Salt By the method of Example 117, 0.125 g of the cis-title product of Example 113 was converted to the free base form of present title product, purified by chromatography using 29:1 $CH_2Cl_2$:isopropanol as eluant, 0.061 g (37%), in turn converted to the dihydrochloride salt according to Example 118, 0.68 g, m.p. greater than 250° C. (decomposes without melting over 95°–150° C.). $^1$H-NMR(DMSO-d delta(ppm): 2.82 (s, 6H), 3.73 (s, 3H), 4.16–4.5 (m, 3H), 5.1–5.21 (m, 1H), 5.32 (s, 2H), 6.3–6.4 (m, 1H), 6.51–6.70 (m, 3H), 6.83–6.93 (m, 1H), 7.05 (s, 2H), 7.12–7.29 (m, 1H), 7.62–7.73 (m, 1H), 7.73–7.91 (m, 1H), 8.13–8.4 (m, 1H), 8.67–8.83 (m, 1H).

EXAMPLE 228

3-(3-Pyridyl)methylene-6-(2-quinolyl)methoxy-4-chromanone

By the method of Example 1, 3.40 g (11.1 mmol) of the title product of Example 55 and 1.19 g (11.1 mmol) of pyridine-3-carbaldehyde gave 1.6 g (36%) of present title product, m.p. 163°–165° C.

MS (m/e) 394 (M+), 302, 142, 116 and 115. IR (KBr) 1639, 1613, 1584 cm$^{-1}$.

EXAMPLE 229

3-(3-Pyridylmethyl)-6-(2-quinolyl)methoxy-4-chromanone

Method A

By the method of Example 2, 1.00 g (2.53 mmol) of the title product of the preceding Example gave 530 mg (53%) of present title product, crystallized from ethyl acetate-hexane, m.p. 108°–110° C.

MS (m/e) 396 (M+), 304, 142, 116, 115, 107 and 92. IR (KBr) 1681, 1614, 1601, 1574, 1562 cm$^{-1}$. $^1$H-NMR(CDCl$_3$, 300 Hz)delta(ppm): 2.73 (dd, J=14, 11 Hz, 1H), 2.89 (m, 1H), 3.13 (dd, J=15, 5 Hz, 1H), 4.11 (dd, J=12, 9 Hz, 1H), 4.34 (dd, J=15, 11 Hz, 1H), 5.34 (s, CH$_2$), 6.91 (d, J=8 Hz, ArH), 7.23 (m, 2ArH), 7.53 (m, 3ArH), 7.62 (d, J=8 Hz, ArH), 7.71 (dd, J=8, 8 Hz, ArH), 7.80 (d, J=8 Hz, ArH), 8.07 (d, J=8 Hz, ArH), 8.17 (d, J=8 Hz, ArH) and 8.47 (bs, ArH).

Analysis calculated for C$_{25}$H$_{20}$N$_2$O$_3$: C, 75.74; H, 5.09; N, 7.07%. Found: C, 75.64; H, 4.76; N, 6.97%.

Method B

To a 5° C. mixture of 22.2 g (55.7 mmol) of trans-title product of Example 5 in 75 ml of water was added 5.9 ml (111 mmol) of concentrated sulfuric acid. To this solution was added 300 ml acetone and then 79.6 ml (55.7 mmol) of 0.7M Jones Reagent was rapidly added. The resultant mixture was stirred 1 hour at 25° C. and then added to saturated sodium bicarbonate (300 ml). The quenched reaction mixture was extracted twice with 150 ml ethyl acetate and once with 150 ml dichloromethane. The combined organic extract was dried over magnesium sulfate and evaporated to a solid. Purification via column chromatography on silica gel eluted with 92:3:3–90:5:5 dichloromethane:isopropanol:ethyl acetate gave 18.5 g (84%) and recrystallization from ethyl acetate-hexane gave product identical with that of present Method A.

This method applied to the cis-title product of Example 5 produces the same product. Applied to 4 g of the product of Example 7, 3.2 g of 3S-(3-pyridyl)methyl-6-(2-quinolyl)methoxy-4-chromanone was produced, m.p. 111°–112° C., [alpha]$_D^{20}$= −4.246° (c=0.22, CH$_3$OH), converted to L-tartrate salt by the method of Example 297 below. Applied to 3.0 g of the product of Example 8, 2.1 g of 3R-(3-pyridyl)methyl-6-(2-quinolyl)methoxy-4-chromanone was produced, has the same m.p., but opposite rotation.

EXAMPLE 230 cis-3-(3-Pyridyl)methyl-6-(2-quinolyl)methoxy-4-chromanol

By the method of Example 4A, 5.00 g (12.6 mmol) of the title product of the preceding Example gave 3.75 g (74%) of present title product (after crystallization from chloroform-diisopropyl ether) identical with the same product produced according to the method of Example 5A.

EXAMPLE 231 trans-3-Benzyl-6-(6-chloro-2-pyridyl)methoxy-4-chromanol

By the method of Example 5, 0.50 g (1.96 mmol) of trans-3-benzyl-4,6-chromandiol and 445 mg (2.16 mmol) of 2-chloro-6-(bromomethyl)pyridine were converted to present title product purified by recrystallization from CH$_2$Cl$_2$/hexane, to yield 0.50 g (67%) of present title compound, m.p. 117°–119° C.

MS (m/e) 381 (M+), 363, (M+-H$_2$O), 137, 91 (100%); high resolution 363.0986 (M+-H$_2$O). IR (CHCl$_3$) 3674, 3577, 3011, 1602, 1588, 1491, 1261, 1157, 1013, 991, 852 cm$^{-1}$. $^1$H-NMR(DMSO-d$_6$)delta(ppm): 7.91 (t, J=7.8 Hz, 1H), 7.51 (d, J=7.8 Hz, 1H), 7.47 (d, J=7.8 Hz, 1H), 7.15–7.32 (m, 5H), 6.98 (d, J=3.7 Hz, 1H), 6.85 (dd, J=9.7, 3.7 Hz, 1H), 6.71 (d, J=9.7 Hz, 1H), 5.49 (d, J=5.7 Hz, 1H), 5.09 (s, 2H), 4.25 (t, J=5.7 Hz, 1H), 4.02 (dd, J=10.3, 3.1 Hz, 1H), 3.80 (dd, J=10.3, 6.0 Hz, 1H), 2.73 (dd, J=12.5, 6.1 Hz, 1H), 2.41 (dd, J=12.5, 8.6 Hz, 1H) and 2.03–2.10 (m, 1H).

EXAMPLE 232 trans-6--2-pyridyl)methoxy-3-(3-pyridyl)methyl-4-chromanol

By the method of Example 5, 500 mg (1.95 mmol) of trans-3-(3-pyridyl)methyl-4,6-chromandiol and 442 mg (2.14 mmol) of 2-chloro-6-(bromomethyl)pyridine were converted to present title product, purified by flash chromatography on a silica gel column using isopropyl alcohol:ethyl acetate:CH$_2$Cl$_2$, 1:2:17 as eluant, to yield 0.11 g (14%) of present title compound as a glass.

MS (m/e) 382 (M+), 256, 137, 9 (100%); high resolution 382.1039. IR (CHCl$_3$) 3589, 2923, 1587, 1491, 1421, 1261, 1157, 1140, 1012, 852 cm$^{-1}$. $^1$H-NMR(DMSO-d$_6$)delta(ppm): 8.42 (dd, J=5.0, 1.5 Hz, 1H), 8.38 (d, J=1.2 Hz, 1H), 7.85 (t, J=7.8 Hz, 1H), 7.61 (dt, J=7.8, 1.2 Hz, 1H), 7.47 (d, J=7.8 Hz, 1H), 7.43 (d, J=7.8 Hz, 1H), 7.33 (dd, J=7.8, 5.0 Hz, 1H), 6.96 (d, J=3.6 Hz, 1H), 6.83 (dd, J=8.5, 3.6 Hz, 1H), 6.68 (d, J=8.5 Hz, 1H), 5.53 (d, J=5.5 Hz, 1H), 5.07 (s, 2H), 4.24 (t, J=5.5 Hz, 1H), 4.00 (dd, J=10.9, 3.1 Hz, 1H), 3.78 (dd, J=10.9, 5.8 Hz, 1H), 2.72 (dd, J=13.9, 6.0 Hz, 1H), 2.43 (dd, J=13.9, 8.7 Hz, 1H) and 2.01–2.14 (m, 1H).

EXAMPLE 233 trans-3-Benzyl-6-(6-methyl-2-pyridyl)methoxy-4-chromanol

By the method of Example 5, 500 mg (1.96 mmol) of trans-3-benzyl-4,6-chromandiol and 401 mg of 2-(bromomethyl)-6-methyl pyridine were converted to present title product, purified by flash chromatography on silica gel using 1:1 ethyl acetate:hexane as eluant to yield 0.38 g (53%) of present title product as white crystals, m.p. 87°–90° C.

MS (m/e) 361 (M+), 343 (M+-H$_2$O), 91; high resolution 361.1692. IR (CHCl$_3$) 3586, 2923, 1598, 1492, 1454, 1257, 1230, 1014, 681 cm$^{-1}$. $^1$H-NMR(DMSO-d$_6$)delta(ppm): 7.67 (t, J=7.8 Hz, 1H), 7.08–7.32 (m, 7H), 6.95 (d, J=3.7 Hz, 1H), 6.81 (dd, J=9.7, 3.7 Hz, 1H), 6.67 (d, J=9.7 Hz, 1H), 5.47 (d, J=5.7 Hz, 1H), 5.04 (s, 2H), 4.25 (t, J=5.7 Hz, 1H), 4.02 (dd, J=10.3, 3.1 Hz, 1H), 3.78 (dd, J=10.3, 6.0 Hz, 1H), 2.72 (dd, J=12.5, 6.1 Hz, 1H), 2.40 (dd, J=12.5, 8.6 Hz, 1H) and 2.00–2.12 (m, 1H).

EXAMPLE 234 trans-6-(6-Methyl-2-pyridyl)methoxy-3-(3-pyridyl)-methyl-4-chromanol

By the method of Example 5, 0.50 g (1.95 mmol) of trans-3-(3-pyridylmethyl)-4,6-chromandiol and 400 mg (2.15 mmol) of 2-(bromomethyl)-6-methyl pyridine were converted to present title product, purified by flash chromatography on silica gel using ethyl acetate as eluant to yield purified title product, o.14 g (20%), m.p. 66°–68° C.

MS (m/e) 362 (M+, 100%), 344 (M+-H$_2$O), 256, 92; high resolution 362.1615. IR (CHCl$_3$) 3589, 2921, 1597, 1491, 1458, 1255, 1156, 1015, 850 cm$^{-1}$. $^1$H-NMR(DMSO-d$_6$)delta(ppm): 8.42 (dd, J=5.0, 1.5 Hz, 1H), 8.38 (d, J=1.2 Hz, 1H), 7.70 (t, J=7.8 Hz, 1H), 7.57 (dt, J=7.8, 1.2 Hz, 1H), 7.28 (dd, J=7.8, 5.0 Hz, 1H), 7.24 (d, J=7.8 Hz, 1H), 7.15 (d, J=7.8 Hz, 1H), 6.96 (d, J=3.6 Hz, 1H), 6.81 (dd, J=8.5, 3.6 Hz, 1H), 6.67 (d, J=8.5 Hz, 1H), 5.51 (d, J=5.5 Hz, 1H -OH), 5.05 (s, 2H), 4.24 (t, J=5.5 Hz, 1H), 4.00 (dd, J=10.9, 3.1 Hz, 1H), 3.78 (dd, J=10.9, 5.8 Hz, 1H), 2.72 (dd, J=13.9, 6.0 Hz, 1H), 2.43 (dd, J=13.9, 8.7 Hz, 1H) and 2.02–2.14 (m, 1H).

EXAMPLE 235 trans-6-(2-Pyridyl)methoxy-3-(3-pyridyl)methyl-4-chromanol

By the method of Example 5, 500 mg (1.95 mmol) of trans-3-(3-pyridyl methyl)-4,6-chromandiol and 266 mg (2.09 mmol) of 2-picolyl chloride were converted to present title product, purified by flash chromatography on 100 g silica gel using 1:19 CH$_3$OH:ether as eluant to yield 136 mg (20%) of present title compound as an oil.

MS (m/e) 348 (M+), 256, 92 (100%); high resolution 348.1429. IR (CHCl$_3$) 3592, 2957, 1595, 1491, 1262, 1206, 1015 cm$^{-1}$. $^1$H-NMR(DMSO-d$_6$)delta(ppm): 8.54 (dt, J=4.8, 1.8 Hz, 1H), 8.40 (dd, J=5.0, 1.5 Hz, 1H), 8.38 (d, J=1.2 Hz, 1H), 7.81 (dt, J=1.8, 7.8 Hz, 1H), 7.60 (dt, J=7.8, 1.2 Hz, 1H), 7.49 (d, J=7.8 Hz, 1H), 7.28–7.36 (m, 2H), 6.98 (d, J=3.6 Hz, 1H), 6.84 (dd, J=8.5, 3.6 Hz, 1H), 6.69 (d, J=8.5 Hz, 1H), 5.53 (d, J=6 Hz, 1H, -OH), 5.10 (s, 2H), 4.26 (t, J=6 Hz, 1H), 4.03 (dd, J=10.9, 3.1 Hz, 1H), 3.80 (dd, J=10.9, 5.8 Hz, 1H), 2.73 (dd, J=13.9, 6.0 Hz, 1H), 2.46 (dd, J=13.9, 8.7 Hz, 1H) and 2.04–2.16 (m, 1H).

EXAMPLE 236 cis-6-(3-Bromo-6-methyl-2-pyridyl)methoxy-3-(3-pyridyl)methyl-4-chromanol

By the method of Example 5, 203 mg (0.79 mmol) of the title product of Example 4A and 218 mg (0.82 mmol) of 3-bromo-2-(bromomethyl)-6-methylpyridine were converted to present title product, purified by flash chromatography on silica gel using ethyl acetate as eluant to yield 93 mg (38%) of purified title compound as a glass.

MS (m/e) 440 (M+), 442 (M+-H$_2$O), 256 (100%), 92; high resolution 440.0682. IR (CHCl$_3$) 3588, 2949, 1576, 1491, 1443, 1275, 1237, 1192, 1151, 1020 cm$^{-1}$. $^1$H-NMR(DMSO-d$_6$)delta(ppm): 8.49 (d, J=1.2 Hz, 1H), 8.44 (dd, J=5.0, 1.5 Hz, 1H), 7.97 (d, J=8.2 Hz, 1H), 7.74 (dt, J=7.8, 1.2 Hz, 1H), 7.35 (dd, J=7.8, 5.0 Hz, 1H), 7.22 (d, J=8.2 Hz, 1H), 6.92 (d, J=3.5 Hz, 1H), 6.86 (dd, J=9.0, 3.5 Hz, 1H), 6.69 (d, J=9.0 Hz, 1H), 5.47 (d, J=5.5 Hz, 1H, OH), 4.30 (t, J=5.5 Hz, 1H), 3.93 (d, J=6.9 Hz, 2H), 2.82 (dd, J=12.6, 7.7 Hz, 1H), 2.59 (dd, J=12.6, 7.3 Hz, 1H), 2.44 (s, 3H), 2.18–2.32 (m, 1H).

EXAMPLE 237 cis-6-(5-Bromo-6-methyl-2-pyridyl)methoxy-3-(3-pyridyl)methyl-4-chromanol

By the method of Example 5, 240 mg (0.93 mmol) of the title product of Example 4A and 270 mg (1.02 mmol) of 3-bromo-6-(bromomethyl)-2-methylpyridine were converted to present title product, purified by recrystallization from ether to yield 65 mg (16%) as a white solid, m.p. 134°–137° C.

MS (m/e) 440 (M+), 442 (M+-H$_2$O), 256 (100%), 92; high resolution 440.0714.

$^1$H-NMR(CDCl )delta(ppm): 8.59 (d, J=1.2 Hz, 1H), 8.51 (dd, J=5.0, 1.5 Hz, 1H), 7.80 (d, J=7.8 Hz, 1H), 7.69 (dt, J=7.8, 1.2 Hz, 1H), 7.33 (dd, J=7.8, 5.0 Hz, 1H), 15 7.19 (d, J=7.8 Hz, 1H), 6.75–6.90 (m, 3H), 5.01 (s, 2H), 4.45 (d, J=5.5 Hz, 1H), 4.07 (d, J=8.4 Hz, 2H), 2.95 (dd, J=12.6, 7.7 Hz, 1H), 2.70 (dd, J=12.6, 7.3 Hz, 1H), 2.63 (s, 3H) and 2.22–2.40 (m, 1H).

EXAMPLE 238 cis-(6-Methyl-2-pyridyl)methoxy-3-(3-pyridyl)methyl-4-chromanol

By the method of Example 5, 500 mg (1.95 mmol) of the title product of Example 4A and 544 mg (2.93 mmol) of 2-(bromomethyl)-6-methylpyridine were converted to present title product, purified by flash chromatography on silica gel using 1:19 CH$_3$OH:ether as eluant to yield 204.2 mg (29%) of the present compound.

IR (CHCl$_3$) 3591, 2952, 1597, 1491, 1459, 1425, 1277, 1242, 1152, 1073, 1023 cm$^{-1}$. $^1$H-NMR(DMSO-d$_6$)delta(ppm): 8.46 (d, J=1.2 Hz, 1H), 8.39 (dd, J=5.0, 1.5 Hz, 1H), 7.62–7.72 (m, 2H), 7.30 (dd, J=7.8, 5.0 Hz, 1H), 7.23 (d, J=7.8 Hz, 1H), 7.14 (d, J=7.8 Hz, 1H), 6.86 (d, J=3.6 Hz, 1H), 6.80 (dd, J=9.0, 3.5 Hz, 1H), 6.66 (d, J=9.0 Hz, 1H), 5.41 (d, J=5.5 Hz, 1H), OH), 5.02 (s, 2H), 4.28 (t, J=5.5 Hz, 1H), 3.91 (d, J=6.9 Hz, 2H), 2.77 (dd, J=12.6, 7.7 Hz, 1H), 2.53 (dd, J=12.6, 7.3 Hz, 1H), 2.46 (s, 3H) and 2.10–2.27 (m, 1H).

EXAMPLE 239

6-(6-Fluoro-2-quinolyl)methoxy-3-(3-pyridyloxy)-4-chromanone

By the method of Example 229, Method B, the title product of Example 75 (500 mg, 1.2 mmol) was converted to present title product, purified by flash chromatography on silica gel using 22:1 $CH_2Cl_2$:$CH_3OH$ as eluant, 202 mg; m.p. 188° C.; MS calculated: 416.1176; found: 416.0798.

EXAMPLE 240

(−)-cis-(6-Fluoro-2-quinolyl)methoxy-3-(3-pyridyloxy)-4-chromanyl Dimethylglycinate Ester By the method of Example 117, the title product of Example 115 (608 mg, 1.4 mmol) was converted to present title product, 578 mg; tlc (5:1 $CH_2Cl_2$:isopropanol) Rf 0.3; MS 503 (M+). By the method of Example 118, except to use 4 molar equivalents of HCl, this product was converted to its trihydrochloride salt, recrystallized from isopropanol and ether, 584 mg; m.p. 160°–165° C. (degassing), 180° C. (dec.); IR 1775 cm$^{-1}$.

EXAMPLE 241

(−)- and (+)-cis-3-(4-Methoxyphenoxy)-6-(2-pyridyl)methoxy-4-chromanol

By the methods of Examples 16–18, the title product of Example 110 (14 g) was resolved into present title products. Initial separation of the intermediate diastereomeric esters was achieved using gradient elution with 5:1, 4:1, 3:1 and finally 1:1 toluene:ethyl acetate to yield 11.87 g of the pure, less polar, (−)-cis isomer and 19.51 g of more polar, (+)-cis isomer, contaminated with some lp isomer. The latter was rechromatographed using 3:1, then 2:1 toluene:ethyl acetate to yield 15.32 g of the pure, more polar (+)-cis isomer. Hydrolysis per Example 18 gave: title (−)-cis isomer, 7.17 g; m.p. 117°–118.5° C.; exact mass calculated: 379.1454; found: 379.1437.

Analysis calculated for $C_{22}H_{21}NO_5$: C, 69.64; H, 5.58; N, 3.69%. Found: C, 69.53; H, 5.59; N, 3.77%.

title (+)-cis isomer, 8.21 g; m.p. 115.5°–117.5° C.; exact mass calculated: 379.1420; found: 379.1282. Analysis calculated as for (−)-isomer. Found: C, 69.46; H, 5.51; N, 3.74%.

EXAMPLE 242

(−)-cis-3-(4-Methoxyphenoxy)-6-(2-pyridyl)methoxy-4-chromanyl Dimethylglycinate Ester By the method of Example 117, the (−)-cis title product of the preceding Example (1.0 g) was converted to present title product, purified by chromatography on silica gel gradiently eluting with 7:1, 5:1 and 3:1 toluene:isopropanol to yield purified title product, 1.20 g; tlc Rf 0.1 (7:1 toluene:ethyl acetate); MS 464 (M+). The latter was converted to its dihydrochloride salt according to Example 118 and recrystallized from isopropanol to yield 1.12 g of dihydrochloride; m.p. 200°–203° C.; IR 1757 cm$^{-1}$.

Analysis calculated for $C_{26}H_{28}N_2O_6 \cdot 2HCl$: C, 57.61; H, 5.26; N, 5.17%. Found: C, 57.60; H, 5.62; N, 5.16%.

By the same method, the title product of Example 111 (0.41 g, 0.916 mol) was converted to (±)-cis-3-(4-methoxyphenoxy)-6-(6-fluoro-2-quinolyl)methoxy-4-chromanyl dimethylglycinate ester dihydrochloride, 0.44 g; m.p. 190°–195° C.; $^1$H-NMR(250 MHz, DMSO-d$_6$) includes delta 3.71 (s, 3H), 2.81 (s, 3H), 2.85 (s, 3H) and 5.34 (s, 2H).

Prepared in like manner were (±)-cis-6-(6-fluoro-2-quinolyl)methoxy-3-(3-pyridyloxy)-4-chromanyl dimethylglycinate trihydrochloride [m.p. 215°–217° C.; $^1$H-NMR (same conditions) includes delta 2.84 (s, 6H), 5.39 (s, 2H)]; and (±)-cis-6-(2-pyridyl)methoxy-3-(3-pyridyloxy)-4-chromanyl dimethylglycinate ester trihydrochloride [m.p. 190°–200° CC ; $^1$H-NMR (same conditions) includes 2.85 (s, 6H) and 5.33 (s, 2H)].

EXAMPLE 243

(+)- and (−)-cis-3-(3-Pyridyloxy)-6-(2-pyridyl)methoxy-4-chromanol

By the method of Examples 114–116, the title product of Example 78 (1.52 g) was resolved into title products. The intermediate carbamate diastereoisomers were separated by silica gel chromatography using $CHCl_3$:isopropanol as eluant followed by hplc on a Zorbax Sil packed column using 19:1 $CHCl_3$:$CH_3OH$ as eluant to yield 986 mg of lp, (−)-cis diastereomer and 875 mg of purified mp (+)-cis isomer. Hydrolysis of these diastereomers according to Example 115 gave:

title (−)-cis isomer, purified by chromatography using 7:1 $CH_2Cl_2$:isopropanol as eluant and recrystallization from toluene, 338 mg; m.p. 146.5–148.5; exact mass calculated: 350.1267; found: 350.1315.

Analysis calculated for $C_{20}H_{18}N_2O_4$: C, 68.56; H, 5.18; N, 8.00%. Found: C, 68.27; H, 5.09; N, 7.97%. [alpha]$_D$= −39° (c=0.1 CHCl$_3$).

title (+)-cis isomer, likewise chromatographed and recrystallized, 312 mg; m.p. 150.5–151.5; exact mass calculated as above; found: 350.1267.

Analysis calculated as above. Found: C, 67.91; H, 5.07; N, 7.98%. [alpha]$_D$=39° (c=0.1 CHCl$_3$).

EXAMPLE 244

(−)-cis-3-(4-Methoxyphenoxy)-6-(2-quinolyl)methoxy-4-chromanol

By the method of Examples 16–18, title product of Example 21 (9.10 g) was resolved via diastereomeric R(−)-O-acetylmandellate esters. Chromatography of these esters on silica gel using 49:1 $CH_2Cl_2$:isopropanol as eluant gave the pure, less polar (−)-cis ester, recrystallized from 1:1 toluene:hexane, 1.87 g; and 8.83 g of mixed (−)-cis and (+)-cis (less polar and more polar, respectively) suitable for recycling and further separation.

The pure (−)-cis ester was hydrolyzed according to Example 17 to yield present title product recrystallized from toluene, 1.13 g; m.p. 154°–156° C. [alpha]$_D$= −52.8° (c=0.1 CHCl$_3$).

EXAMPLE 245

(+)- and (−)-cis-3-(3-Pyridyloxy)-6-(2-quinolyl)methoxy-4-chromanol

By the method of Examples 16–18, title product of Example 78 (1.28 g) was converted to present title products. The intermediate diastereomeric esters were separated by chromatography using 53:43 $CHCl_3$:hexane containing 0.5% triethylamine. Following hydrolysis, each product was recrystallized from toluene to yield:

(+)-cis isomer, 292 mg; m.p. 156.5°–158.5° C.; exact mass calculated: 400.1423; found: 400.1395.

Analysis calculated for $C_{24}H_{20}N_2O_4.0.25H_2O$: C, 71.18; H, 5.10; N, 6.92%. Found: C, 71.39; H, 4.92; N, 6.77%. $[alpha]_D = +40.6°$.

(−)-cis isomer, 171 mg; m.p. 152°–153.5° C.; exact mass calculated as above; found: 400.1418.

Analysis calculated for $C_{24}H_{20}N_2O_4.0.75H_2O$: C, 69.63; H, 5.23; N, 6.77%. Found: C, 69.83; H, 4.84; N, 6.58%.

EXAMPLE 246

(+)-cis-3-(3-Pyridyloxy)-6-(2-quinolyl)methoxy-4-chromanyl Dimethylglycinate Ester Trihydrochloride By the methods of Example 240, title product of Example 76 (250 mg, 0.87 mmol) was converted to present title product, 320 mg; m.p. 165° C. (degassing); exact mass calculated: 485.1953; found: 485.1929.

By the same methods, the title products of the preceding Example were each converted to the corresponding optically active forms:

(+)-cis isomer, 181 mg from 184 mg; exact mass calculated: 485.1954; found: 485.1975.

Analysis calculated for $C_{28}H_{27}O_5N_3.3HCl.2H_2O$: C, 53.29; H, 5.43; N, 6.66%. Found: C, 53.42; H, 5.29; N, 6.61%.

(−)-cis isomer, 228 mg from 235 mg.

Analysis calculated for $C_{28}H_{27}N_3O_5.3HCl.2.5H_2O$: C, 52.54; H, 5.51; N, 6.57%. Found: C, 52.56; H, 5.35; N, 6.63%.

EXAMPLE 247

(±)-cis-3-(4-Methoxyphenoxy)-6-(4-methoxy-2-pyridyl)methoxy-4-chromanol

By the method of Example 13, the title product of Example 20 (494 mg, 3 mmol) and freshly prepared 4-methoxy-2-picolyl chloride (903 mg, 3 mmol) were converted to present title product, purified by chromatography on silica gel using 51:25:4 toluene:ethyl acetate:isopropanol as eluant and recrystallization from toluene, 564 mg; m.p. 80°–82° C.; tlc Rf 0.3 (19:1 $CH_2Cl_2$:isopropanol); exact mass calculated: 409.1531; found: 409.1530.

Analysis calculated for $C_{23}H_{23}NO_6$: C, 67.47; H, 5.66; N, 3.42%. Found: C, 67.13; H, 5.77; N, 3.39%.

EXAMPLE 248

(±)-cis-3-(3-Methoxyphenoxy)-6-(4-methoxy-2-pyridyl)methoxy-4-chromanol

According to the methods of the preceding Example, title product of Example 25 (267 mg, 1.7 mmol) was converted to present title product, 112 mg; m.p. 165°–166° C.; exact mass calculated: 409.1531; found: 409.1540.

EXAMPLE 249

(±)-cis-6-(4-Methoxy-2-pyridyl)methoxy-3-(3-pyridylmethyl)-4-chromanol and its Dihydrochloride By the method of the preceding Example, title product of Example 4A (612 mg) was converted to crude title product in free base form. The latter was taken up in 25 ml of methanol and 2N HCl (2.7 ml) was added. After stirring for 15 minutes, the mixture was stripped in vacuo. The residue was stirred with 20 ml of toluene and restripped three times and the residue triturated with ethyl acetate to yield present title dihydrochloride product, 1.07 g; m.p. 113° C., (degasses) 135° C., (dec.).

This preparation was repeated on 266 mg of the same starting material with purified free base of title product obtained by silica gel chromatography using 3:3:2 toluene:ethyl acetate:isopropanol as eluant and recrystallization from $CH_2Cl_2$, 119 mg; m.p. 66.5–68.5; exact mass calculated: 380.1372; found: 380.1379.

Analysis calculated for $C_{21}H_{20}N_2O_5$: C, 66.30; H, 5.30; N, 7.36%. Found: C, 66.55; H, 5.29; N, 7.24%.

EXAMPLE 250

(±)-cis-3-(3-(Methoxycarbonyl)benzyl)-6-(2-pyridyl)methoxy-4-chromanol

By the method of Example 13, the mixed title product of Example 46 (1.0 g, 3.18 mmol) and 2-picolyl chloride (444 mg, 3.48 mmol) were converted to a mixture of title product and the corresponding trans-isomer. Present title product was separated by two-fold silica gel chromatography, first with 33:1 $CH_2Cl_2$: isopropanol as eluant followed by 3:2 toluene:ethyl acetate as eluant to yield present, purified title product, 422 mg.

EXAMPLE 251

(±)-cis-3-(3-Carboxybenzyl)-6-(2-pyridyl)methoxy-4-chromanol

Title product of the preceding Example (422 mg) was combined with 11 ml of methanol and 5 ml 1N NaOH and then heated at reflux for 15 minutes, cooled, stripped in vacuo and the residue combined with 20 ml of toluene and restripped. The dried residue was chromatographed on silica gel using 6:1 $CH_2Cl_2:CH_3OH$ as eluant, and recrystallized from isopropyl ether/$CH_2Cl_2$/hexane to yield purified title product, 254 mg; m.p. 196.5°–197.5° C., exact mass calculated: 391.1424; found: 391.1425.

Analysis calculated for $C_{23}H_{21}NO_5.0.5H_2O$: C, 68.98; H, 5.29; N, 3.49%. Found: C, 69.10; H, 5.36; N, 3.58%.

EXAMPLE 252

6-(2-Pyridyl)methoxy-3-(3-pyridyloxy)-4-chromanone

By the method of Example 229, Method B, the title product of Example 78 (150 mg, 0.43 mmol) was converted to present title product, purified by silica gel chromatography using 19:1 $CH_2Cl_2$:isopropanol as eluant and recrystallization from toluene, 63 mg; m.p. 155°–156.5° C., exact mass calculated: 348.1114; found: 348.1035.

Analysis calculated for $C_{20}H_{16}N_2O_4.1.25H_2O$: C, 64.75; H, 5.03; N, 7.55%. Found: C, 64.94; H, 4.77; N, 7.29%.

EXAMPLE 253

3-(3-Pyridyloxy)-6-(2-quinolyl)methoxy-4-chromanone

By the method of Example 229, Method B, the title product of Example 76 (527 mg) and/or the corresponding trans-isomer was converted to present title product, purified by silica gel chromatography using 1:1 toluene:ethyl acetate containing 1% glacial acetic acid as eluant, 216 mg; m.p. 174°–175° C., exact mass calculated: 398.1266; found: 398.1232.

Analysis calculated for $C_{24}H_{18}N_2O_4$: C, 72.34; H, 4.55; N, 7.03%. Found: C, 72.10; H, 4.49; N, 6.97%.

EXAMPLE 254

6-Benzyloxy-3-(6-methyl-3-pyridyloxy)-4-chromanone

2-Methyl-5-hydroxypyridine (8.18 g, 0.025 mol) and 6-benzyloxy-3-bromo-4-chromanone (25.0 g, 0.075 mol) were converted to present chromatographed title product by the method of Example 72, 1.34 g; tlc Rf 0.25 (1:4 ethyl acetate:$CH_2Cl_2$); IR ($CHCl_3$) 1702, 1484 cm$^{-1}$.

By the same methods, 2-methyl-3-hydroxypyridine (7.30 g, 0.067 mol) was converted to 1.17 g of 6-benzyloxy-3-(2-methyl-3-pyridyloxy)-4-chromanone [$^1$H-NMR includes delta 2.48 (s, 3H), 4.6 (m, 2H) and 4.93 (dd, 1H); MS includes 361 (M+) and base peak at 91; IR ($CHCl_3$) 1697, 1486 cm$^{-1}$].

EXAMPLE 255

($\pm$)-cis-6-Benzyloxy-3-(6-methyl-3-pyridyloxy)-4-chromanol

By the method of Example 4, title product of the preceding Example (1.33 g, 0.0037 mol) was converted to present title product, 1.40 g, evidently contaminated with 10–15% of trans-isomer by $^1$H-NMR; tlc Rf 0.4 (19:1 $CH_2Cl_2$:$CH_3OH$); IR ($CHCl_3$) 3562 cm$^{-1}$.

By the same method, the isomeric product of the preceding Example (1.16 g, 3.21 mmol) was converted to ($\pm$)-cis-6-benzyloxy-3-(2-methyl-3-pyridyloxy)-4-chromanol, 1.12 g; m.p. 133°–134° C.; tlc Rf 0.28 (1:19 $CH_3OH$:$CH_2Cl_2$; Rf 0.58 (1:9 $CH_3OH$:$CH_2Cl_2$).

EXAMPLE 256

($\pm$)-cis-3-(6-Methyl-3-pyridyloxy)-4,6-chromandiol

By the method of Example 10, using 2 1 $CH_3OH$:THF as solvent, title product of the preceding Example was converted to present title product, purified by silica gel chromatography initially using 19:1 and then 9:1 $CH_3OH$:$CH_2Cl_2$; as eluant, 0.85 g; tlc Rf 0.14 (9:1 $CH_2Cl_2$:$CH_3OH$).

Alternatively, present title product (0.96 g) was prepared from 1.06 g of 6-methoxy-3-(6-methyl-3-pyridyloxy)-4-chromanone (Example 72) according to the method of Example 3.

By the same method, the isomeric product of the preceding Example (1.02 g) was converted to ($\pm$)-cis-3-(2-methyl-3-pyridyloxy)-4,6-chromandiol, 395 mg; tlc Rf 0.24 (1:9 $CH_3OH$:$CH_2Cl_2$); m.p. 240°–241° C.

EXAMPLE 257

($\pm$)-cis-6-(6-Fluoro-2-quinolyl)methoxy-3-(6-methyl-3-pyridyloxy)-4-chromanol By the method of Example 13, title product of the preceding Example (250 mg, 0.92 mmol) and (6-fluoro-2quinolyl)methyl chloride (179 mg, 0.92 mmol) were converted to present title product, purified by silica gel chromatography using gradient elution with 1:50, 1:19 and 1:10 $CH_3OH$:$CH_2Cl_2$, 262 mg; tlc Rf 0.28 (9:1 $CH_3OH$:$CH_2Cl_2$), m.p. 164°–165° C.; IR (KBr) 1501, 1483 cm$^{-1}$.

By the same method, the isomeric product of the preceding Example (270 mg, 0.99 mmol) was converted to ($\pm$)-cis-6-(6-fluoro-2-quinolyl)methoxy-3-(2-methyl-3-pyridyloxy)-4-chromanol, 325 mg; m.p. 158°–159° C.; tlc Rf 0.37 (1:9 $CH_3OH$:$CH_2Cl_2$); exact mass calculated: 432.1486; found: 432.1469; IR (KBr) 1491, 1457 cm$^{-1}$.

By the same method, substituting equivalent 5-fluoro-2-(chloromethyl)benzthiazole for 6-fluoro-2-(chloromethyl)quinoline, title product of the preceding Example (0.14 g, 0.51 mmol) was converted to 0.12 g of cis-6-(5-fluoro-2-benzthiazolyl)methoxy-3-(6-methyl-3-pyridyloxy)-4-chromanol, m.p. 186°–187° C.

EXAMPLE 258

($\pm$)-cis-3-(6-Methyl-3-pyridyloxy)-6-(2-quinolyl)methoxy-4-chromanol

By the method of the preceding Example, except to use 1:50 and then 1:19 $CH_3OH$:$CH_2Cl_2$ as eluant, title product of Example 256 (420 mg, 1.54 mmol) and (2-quinolyl)methyl chloride (274 mg, 2.54 mmol) were converted to present title product, 520 mg; m.p. 134°–136° C ; IR (KBr) 1618, 1571, 1494 cm$^{-1}$; tlc Rf 0.4 (9:1 $CH_2Cl_2$:$CH_3OH$).

By the same method, the isomeric product of Example 257 (300 mg, 1.10 mmol) was converted to ($\pm$)-cis-3-(2-methyl-3-pyridyloxy)-6-(2-quinolyl)methoxy-4-chromanol, 390 mg; m.p. 159°–160° C.; tlc Rf 0.35 (1:9 $CH_3OH$:$CH_2Cl_2$); $^1$H-NMR includes delta 5.33 (s, 2H), 2.39 (s, 3H); IR ($CHCl_3$) 3564, 1491 cm$^{-1}$; exact mass calculated: 414.1581; found: 414.1580.

EXAMPLE 259

(+)- and (−)-cis-3-(6-Methyl-3-pyridyloxy)-6-(2-quinolyl)methoxy-4-chromanol via Esters with N-(t-Butoxycarbonyl)-L-tryptophane Substituting a molar equivalent of N-(t-butoxycarbonyl-L-tryptophane for the O-acetyl mandelic acid in the method of Example 16, title product of the preceding Example (4.73 g, 11.4 mmol) was converted to present diastereomeric title products, separated by gsilica gel chromatography using 21:7:1 $CHCl_3$: hexane:isopropanol as eluant to yield 2.1 g of the less polar (+)-cis isomer and 1.51 g of the more polar (−)-cis isomer. These esters were hydrolyzed by stirring for 1 hour in aqueous methanol (20 ml methanol and 8 ml of 1N NaOH for each gram of ester). The reaction mixtures were diluted with water (20 ml/g), adjusted to pH 7 with 2N HCl and resolved title products recovered by filtration and purified by recrystallization from toluene:

(+)-cis-title product, 3R,4S, 715 mg; m.p. 128.5°–130° C.; exact mass calculated: 414.1580; found: 414.1572.

Analysis calculated for $C_{25}H_{22}N_2O_4 \cdot H_2O$: C, 69.34, H, 5.59; N, 6.48%. Found C, 69.34; H, 5.20; N, 6.30%. [alpha]$_D$= +44.7°.

(−)-cis-title product, 3S,4R, 720 mg; exact mass calculated as above; found: 414.1564.

[alpha]$_D$= −44.2°.

By the same method, the title product of Example 257 (1.9 g, 4.4 mmol) was converted to (+)-cis-6-(6-fluoro-2-quinolyl)methoxy-3-(6-methyl-3-pyridyloxy)-4-chromanol, m.p. 162°–163° C.; and to the corresponding (−)-isomer, m.p. 165°–167° C.

EXAMPLE 260

(+)- and (−)-cis-3-(6-Methyl-3-pyridyloxy)-6-(2-quinolyl)methoxy-4-chromanyl Dimethylglycinate Esters Trihydrochlorides By the methods of Example 240, the title products of the preceding Example (250 mg of each) were converted to present title products:

(+)-cis-title product, 317 mg; m.p. 155° C. (degassing) 180° C. (dec).

(−)-cis-title product, 220 mg; m.p. identical, as expected.

EXAMPLE 261

6-Methoxy-3-(5-pyrimidyl)methylene-4-chromanone

By the method of Example 1, 6-methoxy-4-chromanone (6.76 g, 0.038 mol) and pyrimidine-4-carbaldehyde (4.14 g, 0.038 mol) were converted to present title product, purified by flash chromatography on silica gel using 45:1 $CH_2Cl_2$:isopropanol as eluant, 2.03 g; MS 268 (M+).

EXAMPLE 262

6-Methoxy-3-(5-pyrimidylmethyl)-4-chromanone

By the method of Example 2, title product of the preceding Example (2.03 g) was converted to present title product without trituration, 2.96 g; MS 270 (M+).

EXAMPLE 263

6-Hydroxy-3-(5-pyrimidylmethyl)-4-chromanone

By the method of Example 3, title product of the preceding Example (2.05 g, 0.0076 mol) was converted to present title product, purified by the chromatographic method of Example 261, 269 mg; MS consistent with product.

EXAMPLE 264

($\pm$)-cis-3-(5-Pyrimidylmethyl)-4,5-chromandiol

By the method of Example 4, the title product of the preceding Example (264 mg, 1 mmol) was converted to present title product, purified by chromatography on silica gel using 19:1 $CH_2CL_2$:$CH_3OH$ as eluant, 125 mg; tlc Rf 0.18 (19:1 $CH_2Cl_2$:$CH_3OH$).

EXAMPLE 265

($\pm$)-cis-6-(6-Fluoro-2-quinolyl)methoxy-3-(5-pyrimidylmethyl)-4-chromanol

By the method of Example 75, title product of the preceding Example (125 mg, 0.48 mmol) was converted to present title product using first 14:1 and then 9:1 $CH_2Cl_2$:isopropanol as eluant, 37 mg; m.p. 188°–191° C.; exact mass calculated: 417.1489; found: 417.1508.

EXAMPLE 266

6-Benzyloxy-3-(3-(methoxycarbonyl)phenoxy)-4-chromanone

By the method of Example 72, 6-benzyloxy-3-bromo-4-chromanone (49.9 g, 0.15 mol) and methyl 3-hydroxybenzoate (22.8 g, 0.15 mol) were converted to present title product purified by chromatography on silica gel using $CH_2Cl_2$ as eluant, 2.19 g; tlc Rf 0.22 ($CH_2Cl_2$).

EXAMPLE 267

($\pm$)-cis-6-Benzyloxy-3-(3-(methoxycarbonyl)phenoxy-4-chromanone

Title product of the preceding Example (2.18 g, 5.4 mmol) was dissolved in 120 ml of THF. $CeCl_3.7H_2O$ (1.20 g, 0.32 mmol) was added and the mixture cooled to −40° C. and stirred under $N_2$. $NaBH_4$ (0.204 g, 0.54 mmol) was added and stirring continued for 25 minutes. To achieve complete conversion to product, additional $CeCl_3.7H_2O$ (1.0 g) and $NaBH_4$ (0.102 g) were added and stirring continued for 15 minutes. The reaction was quenched by adding 2 ml of acetone and warming the reaction mixture to room temperature. It was then stripped of solvent and the residue distributed between 150 ml $H_2O$ and 100 ml ethyl acetate. The aqueous layer was separated and extracted 1×100 ml fresh ethyl acetate. The organic layers were combined, washed with brine, dried ($Na_2SO_4$), stripped to 2.41 g of oil and chromatographed on silica gel using 1:19 ethyl acetate:$CH_2Cl_2$ as eluant, 1.34 g; tlc Rf 0.52 (1:9 $CH_3OH$:$CH_2Cl_2$).

EXAMPLE 268

($\pm$)-cis-3-(3-(Methoxycarbonyl)phenoxy-4,6-chromandiol

By the method of Example 12, the title product of the preceding Example (1.34 g) was converted to present title product, purified by silica gel chromatography using 1:4 ethyl acetate:$CH_2Cl_2$ alone and then with 1% $CH_3OH$ as eluants, 935 mg; tlc Rf 0.30 (1:19 $CH_3OH$:$CH_2Cl_2$); MS 316 (M+), 138 (base peak).

EXAMPLE 269

($\pm$)-cis-6-(Substituted)methoxy-3-(3-(methoxycarbonyl)phenoxy)-4-chromanol

By the method of Example 15, title product of the preceding Example was converted to the following present title products:

(a) 6-(5-fluoro-2-benzthiazolyl)methoxy derivative, 726 mg from 547 mg (1.73 mmol), using gradient elution with 1:99, 1:49 and 1:24 $CH_3OH$:$CH_2Cl_2$; tlc Rf 0.48 (1:19 $CH_3OH$:$CH_2Cl_2$); MS 481 (M+), 166 (base peak); IR ($CHCl_3$) 1722, 1489 cm$^{-1}$.

(b) 6-(2-quinolyl)methoxy derivative, 411 mg from 322 mg (1.02 mmol), using 1:99 and then 1:49 $CH_3OH$:$CH_2Cl_2$ as eluant; tlc Rf 0.47 (1:19 $CH_3OH$:$CH_2Cl_2$); MS 457 (M+), 142 (base peak); IR (KBr) 1725, 1499 cm$^{-1}$.

(c) 6-(6-fluoro-2-quinolyl)methoxy derivative 454 mg from 320 mg (1.01 mmol), eluant as (b); tlc Rf 0.63 (1:19 $CH_3OH$:$CH_2Cl_2$); IR (KBr) 3415, 1722 cm$^{-1}$.

(d) 6-(2-pyridyl)methoxy derivative, 363 mg from 359 mg (1.13 mmol), eluant as (a); tlc Rf 0.29 (1:19 $CH_3OH$:$CH_2Cl_2$); MS 407 (M+), 93 (base peak); IR ($CHCl_3$) 3565, 1721, 1490 cm$^{-1}$.

EXAMPLE 270

($\pm$)-cis-6-(Substituted)methoxy-3-(3-carboxyphenoxy)-4-chromanol

By the method of Example 251, the products of the preceding Example were hydrolyzed to present title products as follows:

(a) 6-(5-fluoro-2-benzthiazolyl)methoxy derivative, 383 mg from 620 mg, recrystallized from 1:19 $CH_3OH$:$CH_2Cl_2$; m.p. 211°–212° C.; tlc Rf 0.27 (1:9 $CH_3OH$:$CH_2Cl_2$); exact mass calculated: 467.0839; found: 467.0658.

(b) 6-(2-quinolyl)methoxy derivative 336 mg from 400 mg, not recrystallized; m.p. 144°–145° C.; tlc Rf 0.30 (1:9 $CH_3OH$:$CH_2Cl_2$); MS 443 (M+), 142 (base peak); exact mass calculated: 443.1369; found: 443.1468.

(c) 6-(6-fluoro-2-quinolyl)methoxy derivative, 306 mg from 445 mg, not recrystallized; m.p. 128°–130° C.; tlc Rf 0.27 (1:9 $CH_3OH$:$CH_2Cl_2$); MS 461 (M+), 160 (base peak); IR (KBr) 1699, 1498 cm$^{-1}$; exact mass calculated: 461.1275; found: 461.1253.

(d) 6-(2-pyridyl)methoxy derivative, 79 mg from 344 mg, chromatographed with 1:9 $CH_3OH$:$CH_2Cl_2$ as eluant and recrystallized from 1:19 $CH_3OH$:$CH_2Cl_2$; m.p. 174°–176° C.; tlc Rf 0.20 (1:9 $CH_3OH$:$CH_2Cl_2$); MS 393 (M+; base peak), 137; IR (KBr) 3325, 1703, 1498 cm$^{-1}$.

EXAMPLE 271

(+)- and (-)-trans-3-(3-Pyridylmethyl)-6-(2-quinolyl)methoxy-4-chromanol

By the methods of Examples 6, 7 and 8, trans-title product of Example 5 (3.30 g, 8.28 mmol) was resolved via its diastereomeric R-(−)-O-acetylmandelate esters:

diastereomer A, 1.2 g; MS 574 (M+), 142 (base peak); IR (KBr) 1743, 1673, 1618, 1600, 1575 cm$^{-1}$.

diastereomer B, 0.9 g; m.p. 108°-110° C.; MS 574 (M+), 142 (base peak); IR (KBr) 1745, 1671, 1617, 1599, 1574 cm$^{-1}$.

Analysis calculated for $C_{35}H_{30}N_2O_6 \cdot 0.25H_2O$: C, 72.59; H, 5.31; N, 4.84%. Found: C, 72.55; H, 5.15; N, 4.77%.

Following hydrolysis, title products were obtained as follows:

(−)-trans-isomer (from A), 0.88 g; m.p. 150°-151° C.; [alpha]$_D^{20}$ = −30.8° (CH$_3$OH, c=0.006); IR (KBr) 1638, 1621, 1601, 1575 cm$^{-1}$.

Analysis calculated for $C_{25}H_{22}N_2O_3 \cdot 0.25H_2O$: C, 74.52; H, 5.63; N, 6.95%. Found: C, 74.68; H, 5.51; N, 7.10%.

(+)-trans-isomer (from B), 0.84 g; m.p. 151°-152.5° C.; [alpha]$_D^{20}$ = +30.6° (CH$_3$OH, c=0.005); IR identical with (−)-isomer.

EXAMPLE 272

6-Methoxy-3-(4-pyridyl)methylene-4-chromanone

By the method of Example 1, 6-methoxy-4-chromanone (26.7 g, 0.15 mol) and pyridine-4-carbaldehyde were converted to present title product, 13.5 g; m.p. 170°-171.5° C.; IR (KBr) 1675, 1616, 1598, 1552 cm$^{-1}$.

Analysis calculated for $C_{16}H_{13}NO_3$: C, 71.90; H, 4.90; N, 5.24%. Found: C, 71.76; H, 4.90; N, 5.29%.

EXAMPLE 273

6-Methoxy-3-(4-pyridylmethyl)-4-chromanone

By the method of Example 2, title product of the preceding Example (3.50 g,) was converted to present title product, recrystallized from ethyl acetate/hexane, 3.2 g; m.p. 91°-92.5° C.; MS 269 (M+), 150 (base peak); IR (KBr) 1676, 1618, 1604, 1588, 1561 cm$^{-1}$.

Analysis calculated for $C_{16}H_{15}NO_3$: C, 71.36; H, 5.61; N, 5.20%. Found: C, 71.35; H, 5.58; N, 5.03%.

EXAMPLE 274

6-Hydroxy-3-(4-pyridylmethyl)-4-chromanone

By the method of Example 3, the title product of the preceding Example (7.5 g) was converted to present title product, recrystallized from ethyl acetate, 25 5.2 g; m.p. 188°-189.5° C.; MS 255 (M+), 93 (base peak); IR (KBr) 1688, 1633, 1611, 1587, 1560 cm$^{-1}$.

EXAMPLE 275 cis- and trans-3-(4-Pyridylmethyl)-4,6-chromandiol

By the method of Example 5, title product of the preceding Example (5.0 g, 19.6 mmol) was converted to a mixture of title products, 4.8 g; MS 257 (M+); IR (KBr) 1610, 1561 cm$^{-1}$; $^1$H-NMR (300 MHz, CDCl$_3$) includes delta 4.18 and 4.26 (bs, ratio of 2.7:2.1, C$\underline{H}$OH).

EXAMPLE 276

(±)-cis- and (±)-trans-3-(4-Pyridylmethyl)-6-(2-quino-lyl)methoxy-4-chromanol

By the method of Example 5, except to use KOC(CH$_3$)$_3$ as base, the mixed title product of the preceding Example (4.0 g, 0.016 mol) was converted to present title products, separated by chromatography on silica gel using 8:1:1 CH$_2$Cl$_2$:ethyl acetate:diisopropyl ether as eluant to yield title products as follows:

(±)-cis-isomer, recrystallized from chloroform-diisopropyl ether, 1.2 g; m.p. 115°-117° C.; MS 398 (M+), 142 (base peak); IR (KBr) 1621, 1603, 1571, 1557 cm$^{-1}$.

Analysis calculated for $C_{25}H_{22}N_2O_3$: C, 75.36; H, 5.57; N, 7.03%. Found: C, 75.08; H, 5.55; N, 6.87%.

(±)-trans-isomer, recrystallized from CH$_2$Cl$_2$-diisopropyl ether, 0.90 g; m.p. 145.5°-147° C.; MS 398 (M+), 142 (base peak); IR (KBr) 1619, 1601, 1560 cm$^{-1}$.

Analysis calculated for $C_{25}H_{22}NO_3$: C, 75.36; H, 5.57; N, 7.03%. Found: C, 75.31; H, 5.51; N, 6.89%.

EXAMPLE 277

3S,4S-3-(3-Pyridylmethyl)-6-(2-quinolyl)methoxy-4-chromanyl Dimethylglycinate Ester Trihydrochloride By the methods of Example 240, the 3S,4S-title product of Example 6 (1.0 g, 2.51 mmol) was converted to present title product, recrystallized from ethanolether, 900 mg; m.p. 148° C. (dec.).

Analysis calculated for $C_{29}H_{32}Cl_3N_3O_4 \cdot 0.25H_2O$: C, 58.30; H, 5.48; N, 7.03%. Found: C, 58.08; H, 5.08; N, 6.94%.

EXAMPLE 278

3S,4S-3-(3-Pyridylmethyl)-6-(2-quinolyl)methoxy-4-chromanol L-Lysine Ester

By the method of Example 117, 3S,4S-title product of Example 6 (0.50 g, 1.26 mmol) and N(epsilon)-(t-butoxycarbonyl)-L-lysine (160 mg, 1.32 mmol) were coupled to form the intermediate N-t-boc protected ester, recrystallized from CHCl$_3$-hexane, 700 mg; m.p. 109°-111° C.

Analysis calculated for $C_{41}H_{50}N_4O_8$: C, 67.75; H, 6.93; N, 7.71%. Found: C, 67.99; H, 7.14; N, 7.77%.

Intermediate prepared in this manner (1.1 g, 1.52 mmol) was dissolved in 100 ml of dioxane saturated with dry HCl, stirred for 12 hours at room temperature, and title product recovered by filtration; exact mass calculated: 526.2580; found: 526.2549.

EXAMPLE 279

3S,4S-3-(3-Pyridylmethyl)-6-(2-quinolyl)methoxy-4-chromanyl 4-Piperidinobutyrate Ester Trihydrochloride By the methods of Example 144, using 1:9 CH$_3$OH:ether as eluant on chromatography of the free base, 3S,4S-title product of Example 6 (1.0 g, 2.5 mmol) was converted to present title product, isolated as trihydrochloride by bubbling dry HCl into a solution of the free base in ether, 331 mg; m.p. 74°-78° C.; MS 551 (M+), 168 (base peak); IR (nujol) 3359, 3372, 2913, 2865, 1642, 1494, 1457, 1377, 1210, 500, 453 cm$^{-1}$.

EXAMPLE 280

3S,4S-3-(3-Pyridylmethyl)-6-(2-quinolyl)methoxy-4-chromanol Acetate Ester

To 3S,4S-title product of Example 6 (0.398 g, 1.0 mmol) in 10 ml $CH_2Cl_2$, stirring under $N_2$, was added 10 ml of acetic anhydride. After stirring for 2 days, the reaction mixture was stripped of volatiles in vacuo and the residue flash chromatographed on silica gel using ethyl acetate as eluant to yield title product as an oil, 385 mg; MS 440 (M+), 142 (base peak). $^1$H-NMR (DMSO-$d_6$)delta(ppm) 8.45 (d, 1H), 8.42 (dd, 1H), 8.38 (d, 1H), 7.99 (d, 1H), 7.97 (d, 1H), 7.60–7.77 (m, 4H), 7.30 (dd, 1H), 6.97 (dd, 1H), 6.87 (d, 1H), 6.77 (d, 1H), 5.67 (d, 1H), 5.25 (AB quartet, 2H), 4.09 (dd, 1H), 3.92 (t, 1H), 2.51–2.65 (m, 3H), 1.99 (s, 3H).

EXAMPLE 281

(±)-cis-6-(5-Fluoro-2-benzothiazolyl)methoxy-3-(3-(hydroxymethyl)benzyl-4-chromanol By the method of Example 215, the title product of Example 50 (2.0 g) was converted to present product, purified without chromatography by recrystallization from THF/ethyl acetate, 1.20 g; m.p. 192°–194° C.; exact mass calculated: 451.1253; found: 451.1213.

EXAMPLE 282

(±)-trans-3-(6-Methyl-3-pyridyloxy)-4,6-chromandiol

Above Example 256 was repeated on 6.02 g of Example 255 title product. Following chromatography, the product (4.04 g) was further purified by trituration with 100 ml $CH_2Cl_2$ to yield the (±)-cis-title product of Example 256 (2.54 g). The mother liquor was stripped to yield crude (±)-trans-title product, 0.5 g; tlc Rf 0.35 (1:9 $CH_3OH:CH_2Cl_2$); $^1$H-NMR indicates 20% contamination with the (±)-cis-isomer.

EXAMPLE 283

(±)-trans-3-(6-Methyl-3-pyridyloxy)-6-(2-quinolyl)-4-chromanol

Without further purification, the product of the preceding Example (160 mg, 0.59 mmol) was reacted by the method of Example 5 to yield present title product, separated and purified by chromatography on silica gel using gradient elution with 1:99, 1:49, 1:25 and 1:12.5 $CH_3OH:CH_2Cl_2$, 113 mg; tlc Rf 0.48 (1:9 $CH_3OH:CH_2Cl_2$).

EXAMPLE 284

6-Benzyloxy-3-(3-pyridyloxy)-4-chromanone

To a solution of 3-hydroxypyridine (8.56 g, 90.0 mmol) in 300 ml anhydrous DMF was added portionwise 3.6 g of 60% NaH in oil (90 mmol. 1.0 eq.). Stirring 0.5 hour was followed by the addition of 30.0 g (90.0 mmol, 1.0 eq.) of 3-bromo-6-benzyloxy-4-chromanone in one portion. After 1 hour, the reaction was poured into 1 liter $H_2O$ and extracted 3×250 ml ethyl acetate. The organic layers were combined, washed 1×100 ml $H_2O$, 1×100 ml 10% LiCl and 1×100 ml brine, then dried over $Na_2SO_4$. Filtration and solvent removal afforded 40 g crude product. Silica gel chromatography with 1:4 ethyl acetate:$CH_2Cl_2$ as eluant afforded 1.13 g (3.6%) of purified title product; m.p. 133°–134° C.

EXAMPLE 285 cis- and trans-6-Benzyloxy-3-(3-pyridyloxy)-4-chromanol

Title product of the preceding Example (2.38 g, 6.85 mmol) was dissolved in 120 ml methanol and 80 ml THF. After cooling to 0°–5°, $NaBH_4$ (285 mg, 7.54 mmol, 1.1 eq.) was added in one portion. After 75 minutes, the reaction mixture was warmed to room temperature and concentrated in vacuo. Dilution with 600 ml of ethyl acetate was followed by washing 2×100 ml $H_2O$ and 1×100 ml brine. The organic layer was dried ($Na_2SO_4$), concentrated and dried to yield 2.4 g of present title products; $^1$H-NMR(250 MHz, $CDCl_3$)delta 2Hs 5.05 (s, 2H) with small shoulder 5.02 (5% by integration). The major compound is cis (95%) and the minor compound is trans (5%). MS 349.0 (M+), 91.0 (base peak).

EXAMPLE 286 cis- and trans-3-(3-Pyridyloxy)-4,6-chromandiol

To a solution of the mixed title product of the preceding Example (6.82 g) in 150 ml methanol and 75 ml THF was added 2.5 g of 10% Pd/C (50% water wet) and the mixture hydrogenated at 50 psig for 24 hours. Catalyst was recovered by filtration, the mother liquor stripped of solvent, and the residue chromatographed on silica gel using gradient elution with from 1:19 to 1:9 methanol:$CH_2Cl_2$ to yield present title product as a white powder; 4.42 g; MS 295 (M+, base peak).

EXAMPLE 287

(±)-trans-6-(6-Fluoro-2-quinolyl)methoxy-3-(3-pyridyloxy)-4-chromanone

According to the methods of Example 75, the mixed title products of the preceding Example (2.75 g, 10.6 mmol) were converted to present, chromatographed title product as a 10:1 cis:trans mixture, 3.29 g. Recrystallization from isopropyl ether/$CH_2Cl_2$ gave 2.8 g of purified (±)-cis isomer of title product (identical with the product of Example 75). The mother liquor was stripped to yield 1.1 g of a product enriched in trans-isomer as an oil, which was chromatographed on silica gel (1:24 $CH_3OH:CH_2Cl_2$ as eluant) to yield 0.76 g of a 3:2 cis:trans mixture as a white foam. Final isolation of the title (±)-trans-isomer was achieved using reverse phase hplc, with 40% $CH_3CN$/60% 0.1M $NH_4OAc$ (pH 4.3) as the mobile phase, detection at 254 nm, a flow rate of 6.3 ml/minute and a Dupont Zorbax C-8 ® 9.6 mm×25 cm column as stationary phase. The 3:2 cis:trans mixture was dissolved in 3.3 ml of the mobile phase and injected 0.11 ml on each preparative run. The retention times for the cis and trans-isomers were 15 and 16 minutes, respectively. The product fractions from ten runs were combined and stripped to yield 60.2 mg of the cis-isomer and present title (±)-trans-isomer, 50.5 mg; m.p. 163°–165° C.; MS calculated: 418.1330; found: 418.1214.

EXAMPLE 288

6-Methoxy-3-(2- and 3-(trifluoromethyl)phenyl)methylene-4-chromanones

Present title products were each prepared from 6-methoxy-4-chromanone (26.7 g, 0.15 mol) and 2- or 3-(trifluoromethyl)benzaldehyde (29.6 g, 0.17 mol) according to the method of Example 1 to yield 34 g of the 2-isomer (m.p. 130°-131° C.) and 23 g of the 3-isomer (m.p. 116°-117° C.), respectively.

EXAMPLE 289

3-(2- and 3-(Trifluoromethyl)benzyl-6-methoxy-4-chromanones

By the method of Example 2, the title products of the preceding Example were converted to present title products, each triturated with hexane:

2-isomer: 23 g from 33 g; m.p. 72°-73° C.; MS 336 (M+); IR (KBr) 1687, 1658, 1623, 1609, 1583 cm$^{-1}$.

3-isomer: 9 g from 20 g;

Analysis calculated for $C_{18}H_{15}F_3O_3$: C, 64.29; H, 4.50%. Found: C, 64.37; H, 4.42%.

EXAMPLE 290

6-Hydroxy-3-(2- and 3-(trifluoromethyl)benzyl-4,6-chromanols

By the method of Example 3, the title products of the preceding Example were converted to present title products:

2-isomer: 16.5 g from 21 g; isolated from cyclohexane; m.p. 115°-116° C.; MS 322 (M+), 136 (base peak); IR (KBr) 1683, 1624, 1610, 1587 cm$^{-1}$.

Analysis calculated for $C_{17}H_{13}F_3O_3$: C, 63.36; H, 4.07%. Found: C, 63.35; H, 4.08%.

3-isomer: 6.4 g from 9 g; isolated as solid from acetone/hexane; tlc Rf 0.23 (8:2:1 hexane:ethyl acetate:diisopropyl ether).

EXAMPLE 291 cis- and trans-3-(2- and 3-(Trifluoromethyl)benzyl-4,6-chromandiols

By the method of Example 4, the title products of the preceding Example were converted to present title products:

2-isomer: 7.5 g from 8 g; 2:3 cis:trans mixture; MS 324 (M+); IR (KBr) 1647, 1621, 1608 cm$^{-1}$; $^1$H-NMR(300 MHz, d$_6$-DMSO) includes delta (ppm) 4.24 (dd, J=6, 6Hz) and 4.39 (bs), C$\underline{H}$—OH, integrated to show the 2:3 cis:trans ratio.

3-isomer: 6 g from 6 g; 9:8 cis:trans mixture; $^1$H-NMR (same conditions) includes delta (ppm) 4.26 (d, J=6 Hz) and 4.33 (d, J=3 Hz), C$\underline{H}$—OH, integrated to show the 9:8 cis:trans ratio.

EXAMPLE 292

(±)-cis- and (+)-trans-6-(2-Quinolyl)methoxy-3-(2- and 3-(trifluoromethyl)benzyl)-4-chromanol By the method of Example 5, each of the cis-trans mixtures of the preceding Example were converted to chromatographically separated title products:

from 6 g of cis/trans 2-isomer: 1.3 g of (±)-cis-isomer; m.p. 119°-120.5° C.; MS 465 (M+); IR (KBr) 1621, 1600, 1584, 1570 cm$^{-1}$; 3 g of cis-trans mixture suitable for recycling; and 0.4 g of (±)-trans-isomer; m.p. 110°-112° C. (from CHCl$_3$/hexane), MS 465 (M+); IR (KBr) 1607, 1583, 1569 cm$^{-1}$.

from 5.3 g of cis/trans 3-isomer: 0.6 g of (±)-cis-isomer; m.p. 149°-150° C. (from CH$_2$Cl$_2$/hexane); IR (KBr) 1670, 1617, 1602, 1565 cm$^{-1}$; 3.7 g as cis-trans mixture suitable for recycling; and 0.4 g of trans-isomer; m.p. 147°-148° C. (from CH$_2$Cl$_2$/hexane); IR (KBr) 1617, 1597, 1584 and 1564 cm$^{-1}$.

EXAMPLE 293

3-(6-Methyl and 6-methoxy-3-pyridyl)methylene-6-(2-quinolyl)methoxy-4-chromanones By the method of Example 1, 6-(2-quinolyl)methoxy-4-chromanone and the appropriate 6-substituted-3-pyridine carbaldehyde were converted to present title products:

6-methyl analog: 3.38 g from 4.20 g of the chromanone; m.p. 185°-186° C. from CH$_3$OH/CH$_2$Cl$_2$.

6-methoxy analog: 6.23 g from 7.0 g of the chromanone; m.p. 155°-158° C. from CHOH/diisopropyl ether.

EXAMPLE 294

3-(6-Methyl- and 6-methoxy-3-pyridyl)methyl-6-(2-quinolyl)methoxy-4-chromanones

By the method of Example 2, the products of the preceding Example were converted to present title products:

6-methyl analog: 2.78 g from 3.28 g; m.p. 108°-110° C. (from CH$_2$Cl$_2$:diisopropyl ether); MS 410 (M+); IR (KBr) 1680, 1637, 1614, 1601, 1584, 1560 cm$^{-1}$.

6-methoxy analog: 3.71 g from 5.90 g; m.p. 98°-99° C. (from CH$_2$Cl$_2$:diisopropyl ether); MS 426 (M+); IR (KBr) 1686, 1639, 1611, 1571 cm$^{-1}$.

EXAMPLE 295

(±)-cis- and (±)-trans-3-(6-Methyl- and 6-methoxy-3-pyridyl)methyl-6-(2-quinolyl)methoxy-4-chromanols By the method of Example 5, each of the title products of the preceding Example were converted to present chromatographically separated cis- and trans-isomers, each isolated from CH$_2$Cl$_2$/diisopropyl ether:

from 2.0 g of the 6-methyl analog, 0.516 g of the cis-isomer; m.p. 121°-123° C.; MS 412 (M+); and 0.48 g of the trans-isomer; m.p. 164°-165° C.; MS 412 (M+).

from 2.48 g of the methoxy analog, 1.08 g of the cis-isomer; m.p. 132°-133° C.; MS 428 (M+); IR (CHCl$_3$) 3589, 3388, 1610, 1571 cm$^{-1}$; and 0.75 g of the trans-isomer; m.p. 144°-145° C.; MS 428 (M+); IR (CHCl$_3$) 3582, 3374, 1610, 1572 cm$^{-1}$.

EXAMPLE 296

3S,4S-3-(1-Oxo-3-pyridyl)methyl-6-(2-quinolyl)methoxy-4-chromanol

The title product of Example 7 (1.0 g, 2.5 mmol) and m-chloroperbenzoic acid (0.55 g, 3.19 mmol) in 100 ml of CH$_2$Cl$_2$ was stirred for 12 hours. The reaction mixture was then washed with saturated NaHCO$_3$, dried (MgSO$_4$), stripped of solvent and the residue chromatographed on silica gel using 8:1:1 CH$_2$Cl$_2$:ethyl acetate:isopropanol and finally recrystallized from ethyl acetate and diisopropyl ether to yield purified title product, 0.29 g; m.p. 163°-164° C.; exact mass calculated: 414.1487; found: 414,1579; [alpha]$_D^{20}$ = −65.38° (ethanol).

Analysis calculated for $C_{25}H_{22}N_2O_4 \cdot 0.5H_2O$: C, 70.91; H, 5.47; N, 6.62%. Found: C, 71.01; H, 5.39; N, 6.37%.

EXAMPLE 297

Acid Addition Salts of 3S,4S-3-(3-Pyridylmethyl)-6-(2-quinolyl)methoxy-4-chromanol

Dihydrochloride

To a solution of 500 mg (1.26 mmol) of the title product of Example 7 in $CH_2Cl_2$ was added an excess of dichloromethane saturated with saturated $HCl/CH_2Cl_2$. The solvent was evaporated and the residue recrystallized from ethanol-ether to give 495 mg (84%) of the dihydrochloride salt hydrate; m.p. 135° C. (dec.).

Analysis calculated for $C_{25}H_{24}Cl_2M_2O_3.0.5H_2O$: C, 62.51; H, 5.24; N, 5.83%. Found: C, 62.21; H, 5.17; N, 5.72%.

Mono L-Tartrate

A mixture of 398 mg (1.0 mmol) of the title product of Example 7 and 300 mg (2.0 mmol) of L-tartaric acid in 20 ml acetone was heated to obtain a solution and then cooled to 25° C. Pentane (80 ml) was added causing precipitation. The precipitate was collected and recrystallized from acetone-pentane to give 187 mg (34%) of the mono L-tartrate hydrate; m.p. 152°–154° C.

Analysis calculated for $C_{29}H_{28}N_2)_9.1.25H_2O$: C, 61.00; H, 5.38; N, 4.91%. Found: C, 60.66; H, 5.00; N, 4.74%.

Diphosphate

To a solution of 500 mg (1.26 mmol) of title product of Example 7 in methanol was added 0.172 ml (2.51 mmol) of 85% phosphoric acid. The mixture was heated to give a solution and then cooled to 25° C. The precipitate formed was filtered to yield 390 mg (45%) of the diphosphate salt solvated with one equivalent phosphoric acid; m.p. 148°–150° C.

Analysis calculated for $C_{25}H_{28}N_2O_{11}P_2.H_3PO_4$: C, 43.36; H, 4.51; N, 4.05%. Found: C, 43.69; H, 4.50; N, 4.05%.

Mono Fumarate

A mixture of 500 mg (1.26 mmol) of title product of Example 7 and 291 mg (2.51 mmol) of fumaric acid in acetone was heated to obtain a solution and then cooled to 25° C. The precipitate formed was collected to yield 500 mg (77%) of the mono fumarate salt; m.p. 165°–166° C.

Analysis calculated for $C_{29}H_{26}N_2O_7$: C, 67.69; H, 5.09; N, 5.45%. Found: C, 67.63; H, 5.04; N, 5.22%.

EXAMPLE 298

7-Methoxy-3-(3-pyridyl)methylene-4-chromanone

By the method of Example 1, 7-methoxy-4-chromanone (10 g, 56 mmol) and 3-pyridine carbaldehyde (5.2 g, 73 mmol) were converted to present title product, isolated directly from the reaction mixture by cooling to 0° C., 11.9 g; m.p. 176°–178° C.; MS 267 (M+, base peak).

Analysis calculated for $C_{16}H_{13}NO_3$: C, 71.90; H, 4.90; N, 5.24%. Found: C, 71.94; H, 4.93; N, 5.05%.

By the same method, 7-methoxy-4-chromanone (5.0 g, 28 mmol) and 3-(methoxycarbonyl)benzaldehyde (2.04 g, 28.7 mmol) were converted to 7-methoxy-3-(3-(methoxy- carbonyl)phenyl)methylene-4-chromanone, 6.14 g; m.p. 126°–128° C.; MS 324 (M+, base); IR (nujol) 2950, 2918, 2851, 1730, 1661, 1583, 1460, 1292, 1239, 925, 817, 288 cm$^{-1}$.

EXAMPLE 299

7-Methoxy-3-(3-pyridylmethyl)-4-chromanone

Title product of the preceding Example (12.85 g) in 300 ml $CH_3OH$ was hydrogenated for 12 hours at 50 psig over 1.4 g of 10% Pd/C. Catalyst was recovered by filtration. The filtrate was stripped to an oil from which title product was crystallized by trituration with 200 ml of warm isopropyl ether, 9.89 g; m.p. 95°–99° C.; MS 269 (M+), 122 (base); IR (CHCl$_3$) 2958, 1678, 1611, 1577, 1435, 1258, 837 cm$^{-1}$.

Analysis calculated for $C_{16}H_{15}NO_3$: C, 71.13; H, 5.57; N, 5.12%. Found: C, 70.94; H, 5.54; N, 5.06%.

In like manner the other product of the preceding Example (6.14 g) in 100 ml of 1:1 methanol:THF was converted to 7-methoxy-3-(3-(methoxycarbonyl)benzyl-4-chromanone, isolated directly upon stripping the catalyst filtrate, 4.50 g; MS 326 (M+, base).

EXAMPLE 300

7-Hydroxy-3-(3-pyridylmethyl)-4-chromanone

By the method of Example 3, title product of the preceding Example (3.8 g) was converted to present title product, 1.32 g; m.p. 181°–190° C.

Analysis calculated for $C_{15}H_{13}NO_3.0.25H_2O$: C, 69.35; H, 5.24; N, 5.39%. Found: C, 69.96; H, 5 16; N, 5.33%.

Application of this method to the other product of the preceding Example (4.5 g, 13.8 mmol) concurrently hydrolyzed the methyl ester to yield 7-hydroxy-3-(3-carboxybenzyl)-4-chromanone, 1.54 g; m.p. 234°–236° C.; MS 298 (M+), 136 (base); IR (nujol) 3316, 2920, 2850, 1609, 1578, 1448, 1284, 848, 695, 276 cm$^{-1}$. To reesterify, the acid was taken into 34 ml $CH_3OH$, and the solution saturated with dry HCl and then heated to reflux for 1 hour. The reaction mixture was stripped and the residue recrystallized from $CH_2Cl_2$ to yield the corresponding methyl ester, 1.39 g; m.p. 157°–159° C.; MS 312 (M+), 136 (base); IR (nujol) 2947, 2921, 2848, 1717, 1459, 1376, 1346, 1297, 1248, 1172, 753, 282 cm$^{-1}$.

EXAMPLE 301

3-(3-Pyridylmethyl)-7-(2-quinolyl)methoxy-4-chromanone

By the method of Example 5, the title product of the preceding Example (3.0 g, 11.7 mmol) was converted to present title product using in sequence $CH_2Cl_2$, ether and finally 1:19 $CH_3OH$:ether as chromatography eluants to yield present, purified title product, 2.17 g; m.p. 111°–114° C.; IR (nujol) 2950, 2921, 2851, 1677, 1611, 1243, 1173, 834, 267 cm$^{-1}$.

In like manner, the other, esterified product of the preceding Example (700 mg, 2.24 mmol), was converted to chromatographically purified 3-(3-(methoxycarbonyl)benzyl-7-(2-quinolyl)methoxy-4-chromanone, 394 mg; MS 453 (M+), 142 (base); IR (CHCl$_3$) 2947, 1721, 1607, 1466, 1436, 1287, 1256, 1237, 1163, 822, 218 cm$^{-1}$.

Substituting 2-(chloromethyl)-6-fluorobenzothiazole for 2-(chloromethyl)quinoline, the other, esterified product of the preceding Example (1.63 g, 5.22 mmol) was converted to 7-(6-fluoro-2-benzothiazolyl)methoxy-3-(3-(methoxycarbonyl)benzyl)-4-chromanone, 1.5 g; m.p. 162°–165° C.; IR (nujol) 2946, 2926, 1723, 1457, 1366, 1276, 1156, 965, 800, 748, 266 cm$^{-1}$.

EXAMPLE 302

(±)-cis- and (±)-trans-3-(3-Pyridylmethyl)-7-(2-quinolyl)methoxy-4-chromanol

By the method of Example 4, the title product of the preceding Example (1.97 g, 5.0 mmol) was converted to present title products, separated by chromatography on silica gel using ether and then 1:19 CH$_3$OH:ether as eluants to yield title products as follows:

(±)-cis-product: 944 mg; m.p. 48°–65° C.; MS 398 (M+), 142 (base); IR (CHCl$_3$) 2948, 1617, 1265, 1163, 723 cm$^{-1}$.

Analysis calculated for C$_{25}$H$_{22}$N$_2$O$_3$: C, 75.36; H, 5.56; N, 7.03%. Found C, 75.08; H, 5.41; N, 6.81%.

(±)-trans-product: 680 mg; m.p. 53°–55° C.; MS 398 (M+), 131 (base); IR (CHCl$_3$) 2954, 1618, 1425, 1270, 1162, 249 cm$^{-1}$.

In like manner, the other 2-quinolyl substituted product of the preceding Example (396 mg, 0.87 mmol) was converted to corresponding cis-trans products separated by silica gel chromatography with 1:1 hexane:ether as eluant, yielding 3-(3-(methoxycarbonyl)benzyl)-7-(2-quinolyl)methoxy products as follows:

(±)-cis-product, 175 mg; m.p. 50°–70° C.; MS 455 (M+), 142 (base); IR (CHCl$_3$) 2947, 1720, 1617, 1588, 1287, 1164, 250 cm$^{-1}$.

(±)-trans-product, 161 mg; m.p. 60°–65° C.; MS 455 (M+), 142 (base); IR (CHCl$_3$) 2946, 1720, 1618, 1288, 1163, 1113, 242 cm$^{-1}$.

Likewise, without separation of the isomers, the 6-fluoro-2-benzothiazolyl product of the preceding Example was converted to an ether recrystallized 3:1 cis:trans mixture of 7-(6-fluoro-2-benzothiazolyl)methoxy-3-(3-(methoxycarbonyl)benzyl-4-chromanols, 262 mg; m.p. 149°–151° C.; IR (CHCl$_3$) 3405, 2947, 1720, 1615, 1588, 1288, 1163, 858, 623 cm$^{-1}$; $^1$H-NMR(DMSO-d$_6$)-delta includes 7.24 (d, J=8.8 Hz, 0.25H) and 7.13 (d, J=8.8 Hz, 0.75H), 6.67 (dd, J=8.8, 2.4 Hz, 0.25H) and 6.60 (dd, J=8.8, 2.4 Hz, 0.75H), 6.53 (d, J=2.4 Hz, 0.25H) and 6.49 (d, J=2.4 Hz, 0.75H).

EXAMPLE 303

(±)-cis-3-(3-Carboxybenzyl)-7-(2-quinolyl)methoxy-4-chromanol

To 175 mg (0.38 mmol) of the (+)-cis-3-(3-(methoxycarbonyl)benzyl derivative of the preceding Example in 2.6 ml THF, 2.6 ml CH$_3$OH and 0.7 ml of H$_2$O was added 355 mg (2.57 mmol) of freshly ground K$_2$CO$_3$, and the mixture heated and stirred at 90° C. for 18 hours, then cooled and diluted with 25 ml each of water and ether. The aqueous layer was separated, adjusted to pH 2.0 with 1N HCl and extracted 3×25 ml fresh ether. The organic layers were combined, dried (MgSO$_4$) and stripped to yield present title product, 138 mg; m.p. 165°–168° C.; MS 423 (M+-H$_2$O), 142 (base); IR (KBr) 3415, 2955, 1692, 1451, 1170, 827, 225, 215 cm$^{-1}$.

In like manner, the corresponding trans-(2-quinolyl) derivative of the preceding Example (161 mg) was converted to the corresponding (±)-trans-3-(3-carboxybenzyl)-7-(2-quinolyl)methoxy-4-chromanol, 99 mg; m.p. 155°–157° C.; MS 423 (M+-H$_2$O, base); IR (KBr) 3414, 2918, 1713, 1619, 1502, 1322, 1253, 830, 756, 246 cm$^{-1}$.

In like manner, the 3:1 cis:trans mixture of 6-fluoro-2-benzothiazolyl derivatives of the preceding Example (262 mg, 0.55 mmol) was converted to a 3:2 cis:trans mixture of 3-(3-carboxybenzyl)-7-(6-fluoro-2-benzothiazolyl)methoxy-4-chromanols, 203 mg; m.p. 122°–133° C ; MS 447 (M+, base); IR (CHCl$_3$) 2924, 1696, 1616, 1589, 1458, 1162, 830 cm$^{-1}$; $^1$H-NMR(DMSO-d$_6$) includes delta 7.28 (d, J=8.8 Hz, 0.6H) and 7.17 (d, J=8.8 Hz, 0.4H), 6.70 (dd, J=8.8, 2.4, 0.6H) and 6.63 (dd, J=8.8, 2.4, 0.4H) and 6.56 (d, J=2.4 Hz, 0.6H), 6.56 (d, J=2.4 Hz, 0.6H) and 6.52 (d, J=2.4 Hz, 0.4H).

EXAMPLE 304

3-Benzyl-2-methyl-6-(2-quinolyl)methoxy-4-chromanols

By the methods of Examples 1, 2, 3 and 55, 6-methoxy-2-methyl-4-chromanone was converted to cis- and trans-3-benzyl-6-(2-quinolyl)methoxy-2-methyl-4-chromanone which, in turn, by the method of Example 4, was converted to:

t-3-benzyl-c-2-methyl-6-(2-quinolyl)methoxy-r-4-chromanol, m.p. 139°–141° C.;

c-3-benzyl-t-2-methyl-6-(2-quinolyl)methoxy-r-4-chromanol, m.p. 109°–112° C.; and t-3-benzyl-t-2-methyl-6-(2-quinolyl)methoxy-r-4-chromanol, m.p. 72°–74° C.

EXAMPLE 305

4-Chromanols

By the methods of Examples 231–238, the following additional 4-chromanols were prepared:

| cis/trans | 3-substituent | 6-methoxy-substituent | m.p. (°C.) |
|---|---|---|---|
| cis | benzyl | 5-trifluoromethyl-2-benzothiazolyl | 157–158 |
| trans | benzyl | 5-trifluoromethyl-2-benzothiazolyl | 180–181 |
| cis | benzyl | 5-chloro-2-benzothiazolyl | 150–151.5 |
| trans | benzyl | 5-chloro-2-benzothiazolyl | 173–174 |
| trans | benzyl | 1-methyl-2-benzoimidazolyl | 200–201 |
| cis | 3-picolyl | 6-fluoroquinolyl | 163–165 |
| trans | 3-picolyl | 6-fluoroquinolyl | 148–150 |
| cis | 3-picolyl | 5-fluoro-2-benzothiazolyl | 166–168 |
| trans | 3-picolyl | 5-fluoro-2-benzothiazolyl | 160–163 |
| cis | 3-picolyl | 5-chloro-6-methoxy-2-quinolyl | 145–147 |
| trans | 3-picolyl | 5-chloro-6-methoxy-2-quinolyl | 142–144 |
| trans | benzyl | 2-benzothiazolyl | 138–139 |
| cis | benzyl | 5-fluoro-2-benzothiazolyl | 133–135 |
| trans | benzyl | 5-fluoro-2-benzothiazolyl | 176.5–177.5 |
| cis | benzyl | 2-benzoxazolyl | 121.5–123 |
| trans | benzyl | 2-benzoxazolyl | 145 |

EXAMPLE 306

Alternative Method for cis-3R-(3-Carboxybenzyl)-6-(5-fluoro-2-benzothiazolyl)methoxy-4R-chromanol Title product of Example 51 (15.0 g, 32.2 mmol) was added slowly to boiling methanol (400 ml) on a steam bath until solution was obtained. Quinine (12.3 g, 32.4 mmol) was dissolved in methanol (50 ml) and the two solutions combined and allowed to cool with stirring for 3 days. The quinine salt of title product as a white solid was collected by vacuum filtration, washed with methanol and air dried (11.78 g, m.p. 201°-203.5° C.). This quinine salt (11.72 g) was added in portions to boiling methanol (1050 ml). When solution was obtained, the hot solution was filtered through fluted filter paper to remove a haze, then the volume reduced to 320 ml by atmospheric distillation of the solvent. After concentration of the solution, crystallization commenced immediately and was allowed to proceed overnight at ambient temperature. The white solid product was collected by vacuum filtration, and air dried to give 9.4 g of purified quinine salt of title product, m.p. 204°-206° C., $[alpha]_D^{25} = 32.8°$ (c=0.56 methanol). To a rapidly stirring biphasic mixture of hydrochloric acid (1N, 75 ml) and ethyl acetate (200 ml) was added the quinine salt (9.34 g). The phases were separated and the aqueous phase extracted again with ethyl acetate (100 ml). The combined organic phases were dried with sodium sulfate (10 g), filtered, and concentrated to 75 ml. Present title product (4.94 g), which crystallized as a white solid on standing, was collected by filtration and air dried. It was identical in properties with the same product obtained in Example 194 above.

The filtrate from isolation of the above quinine salt is stripped to yield the impure diastereomeric quinine salt, i.e., the quinine salt of the enantiomer of present title product, which, by the steps of salt hydrolysis as described in the preceding paragraph, oxidation to 3S-ketone according to Method B of Example 229, racemization at C.3 with excess strong base (e.g., 1.1 molar equivalents of sodium methoxide in methanol), and reduction to alcohol at C.4 according to the method of Example 4A above is recycled to present starting material.

EXAMPLE 307

Alternative Method for cis-3S-(3-Pyridylmethyl)-6-(2-quinolyl)methoxy-4S-chromanol A reaction flask equipped with stirrer and thermometer was charged with 5.0 liters ethyl acetate, milled L-tartaric acid (15.1 g, 0.10 mol) and (+)-cis-3-(pyridylmethyl)-6-(2-quinolyl)methoxy-4-chromanol (39.9 g, 0.10 mol). The stirred slurry was warmed to 40° C. for 2 hours, then to 50° C. for 2 hours and finally cooled slowly to 25° C. The L-tartrate salt of present title product (25.4 g after vacuum drying at 40° C. for 3 hours) was recovered by filtration. The filtrate was stripped to 200 ml and the crude, diastereomeric salt (27.1 g, suitable for recycling as noted below) recovered by filtration. Crude title product was purified by repulping in 1.5 liters of ethyl acetate, stirring for 4 hours at 50° C. and slowly cooling to 25° C. to recover 21.3 g of the purified L-tartrate salt of present title product, m.p. 143-150 (cloudy); $[alpha]_D^{25} = -59.5°$ (c=0.6 CH$_3$OH); cf. hydrated form from acetone of Example 297 above. Stripping the repulp liquor produced an additional 3.1 g of crude diastereomeric salt suitable for recycling.

The purified L-tartrate of title product (21.0 g, 0.038 mol) was added in portions to a mixture of aqueous NaOH (4.0 g, 0.1 mol in 200 ml of H$_2$O) and CH$_2$Cl$_2$ (200 ml). The mixture was stirred 0.5 hour, the organic layer separated and the aqueous layer washed 2×75 ml fresh CH$_2$Cl$_2$. The organic layers were combined, backwashed 3×100 ml H$_2$O, treated with 2 g of activated carbon, dried (Na$_2$SO$_4$), stripped to 20 ml, twice diluted with 50 ml acetone and restripped to 25 ml, cooled to 15° C. and stirred for 0.5 hour, and present title product (11.8 g vacuum dried at 40° C. for 2 hours) recovered by filtration. This product was identical with the product of Example 7 above.

The above-isolated, crude, diastereomeric salt is hydrolyzed to the crude 3R,4R-enantiomer of title product in like manner. The latter is recycled via Jones oxidation to the corresponding 3R-ketone according to Method B of Example 229 above, racemized with base (e.g., 0.1 molar equivalents of sodium methoxide in methanol) to yield the title product of Example 229, and reduced to present racemic starting material according to Examples 4A and 230.

PREPARATION 1

4-(2-Cyanoethoxy)anisole

4-Methoxyphenol (248 g), KOH (5.6 g) and acrylonitrile (397 ml) were dissolved in 1 liter of t-butanol and heated with stirring at 75° C. for 5 hours. The mixture was then cooled to room temperature and stripped in vacuo to solid residue, which was repulped in ether and insolubles recovered by filtration. The latter were taken up in 2 liters of ethyl acetate, washed in sequence with 1 liter each of H$_2$O, saturated NaHCO$_3$ and saturated NaCl, dried over MgSO$_4$ and restripped to yield purified title product, 199.4 g, m.p. 62°-64° C.

PREPARATION 2

6-Methoxy-4-chromanone

The title product of the preceding Example (199 g) was combined with 240 ml H$_2$O and 480 ml of concentrated HCl and heated at reflux overnight. The reaction mixture was cooled to room temperature and solids recovered by filtration. The latter were taken up in 2 liters of ethyl acetate, washed with 200 ml of H$_2$O, dried over MgSO$_4$ and stripped in vacuo to yield intermediate 3-(4-methoxyphenoxy)propionic acid, 195 g, m.p. 105°-107° C. The latter was added to 600 ml of hot, stirred polyphosphoric acid maintained at 75° C. and the mixture stirred for 2 hours. The temperature rose to a maximum of 89° C. over the first one-half hour, then fell to the 75° C. bath temperature. The reaction mixture was quenched into 3.2 liters of ice and water and extracted with 1.2 liters of ethyl acetate. The organic extract was in sequence with 600 ml each of H$_2$O, saturated NaHCO$_3$ and saturated NaCl, dried over MgSO$_4$ and stripped to 180 g of solids which were taken up in 400 ml CH$_2$C$_2$, treated with activated carbon and restripped to a like quantity of solids. The latter were recrystallized from isopropyl ether to yield purified title product, 120 g, m.p. 46°-48° C., identical with the commercial product.

PREPARATION 3

6-Hydroxy-4-chromanone

A solution of 36 g of the product of the preceding Preparation in 290 ml of acetic acid and 290 ml of 48% hydrobromic acid was heated at reflux for 3 hours. The reaction was cooled and stripped in vacuo to crude product which was diluted with water (6 liters), cooled to 0°-5° C. and title product recovered by filtration, 25.7 g (80%), m.p. 133°-136° C. Optionally, the product is further purified by chromatography on silica gel using ethyl acetate/hexane as eluant.

PREPARATION 4

6-Benzyloxy-4-chromanone

A mixture of 25 g of the product of the preceding Preparation, 26.5 g of benzyl bromide and 28 g of potassium carbonate in 150 ml of acetone was heated at reflux overnight. The reaction was cooled and filtered to remove potassium carbonate. The filtrate was evaporated and the residue was dissolved in ethyl acetate and washed with water. The ethyl acetate layer was dried over sodium sulfate and evaporated in vacuo to obtain the crude product, which was purified by recrystallization from methylene chloride/hexane to give 29 g of title product, m.p. 107°–108° C. $^1$H-NMR(acetone-d$_6$)delta(ppm): 2.7 (t, 2H), 4.4 (t, 2H), 5.08 (s, 2H), 7.2–7.5 (m, 3H).

PREPARATION 5

3-Hydroxymethylene-6-benzyloxy-4-chromanone

To a solution of 172.5 g of the product of the preceding Preparation in 1.7 liters of toluene containing 168 ml of ethyl formate and 3.5 ml of ethanol was added, in portions, 66 g of 50% sodium hydride. The reaction was allowed to stir at room temperature for 1 hour, then poured into 1.5 liters of ice and H$_2$O, and acidified to pH 4 with dilute hydrochloric acid. The aqueous layer was extracted with several portions of ethyl acetate. The organic layers were combined, dried over sodium sulfate and evaporated in vacuo to give the crude product which was triturated with hexane to remove hydride oil. The resultant product crystallized on standing, m.p. 82°–85° C.

PREPARATION 6

3-Diazo-6-benzyloxy-4-chromanone

To a −10° C. solution of 35.3 g of title product of the preceding Preparation in 250 ml of dichloromethane containing 25.2 g of triethylamine was added dropwise a solution of 24.4 g of tosyl azide in 100 ml of dichloromethane. After complete addition, the reaction was allowed to warm to room temperature and stirred overnight. The reaction mixture was washed with water, dried over sodium sulfate and evaporated in vacuo to give the crude product, which was purified by column chromatography on silica gel eluting with dichloromethane to give 21 g of product, m.p. 100°–103° C. $^1$H-NMR(CDCl)delta(ppm): 5.02 (d, J=4, 2H), 6.7–7.5 (m, 10H).

PREPARATION 7

4-(4-Methoxyphenoxy)butyric Acid

4-Methoxyphenol was added to a solution of NaOC$_2$H$_5$ made by dissolving 2.3 g of Na in 50 ml ethanol. After 5 minutes, gamma-butyrolactone was added and the mixture heated at reflux overnight. Ethanol was distilled off and the residue heated at 155° C. overnight, then cooled, diluted with water and acidified to pH 3 with dilute hydrochloric acid. The product was collected by filtration, 19.5 g, m.p. 103°–104° C.

PREPARATION 8

3,4-Dihydro-7-methoxy-1-benzoxepin-5(2H)-one

The product of the preceding Preparation, 34 g, was dissolved in 300 ml of polyphosphoric acid and heated at 100° C. for 1 hour. The reaction was cooled, poured into water and extracted with ether to give the crude product. It was purified by distillation, b.p. 100° C./0.5 mm.

PREPARATION 9

3,4-Dihydro-7-hydroxy-1-benzoxepin-5(2H)-one

A mixture of 19.23 g of the product of the preceding Preparation, 95 ml of 48% hydrobromic acid and 95 ml of acetic acid was heated at reflux for 4 hours. The reaction was cooled and evaporated in vacuo to afford the crude product, which was purified by column chromatography on silica gel, eluting with dichloromethane to give 8.3 g of product, m.p. 116°–120° C. $^1$H-NMR(CDCl$_3$)delta(ppm): 2.0–2.45 (m, 2H), 2.95 (t, J=7, 2H), 4.20 (t, J=7, 2H), 6.8–7.1 (m, 3H), 7.4 (s, 1H).

PREPARATION 10

7-Benzyloxy-3,4-dihydro-1-benzoxepin-5(2H)-one

A mixture of 6.5 g of the product of the preceding Preparation, 4.3 ml of benzyl bromide, 6.3 g of potassium carbonate and 40 ml of acetone was heated with stirring at reflux overnight. The reaction was cooled and filtered to remove inorganics. The filtrate was evaporated in vacuo, and the residue dissolved in ethyl acetate and washed with water. The ethyl acetate layer was dried over sodium sulfate and evaporated in vacuo to give the crude product which was purified by recrystallization from isopropyl ether to give 8.4 g of title product, m.p. 62°–63° C.

PREPARATION 11

7-Benzyloxy-4-bromo-3,4-dihydro-1-benzoxepin-5(2H)-one

To a solution of 6.3 g of the title product of the preceding Preparation in 25 ml of acetic acid was added a solution of 3.76 g of bromine in 25 ml of acetic acid. The reaction was stirred for 3 minutes and the volatiles evaporated in vacuo to a residue which was dissolved in ethyl acetate and washed with water. The ethyl acetate layer was dried and evaporated to give 8.2 g of product which was used without purification in the next step.

PREPARATION 12

3-Bromo-6-methoxy-4-chromanone

To a solution of 6-methoxy-4-chromanone (35 g) in ethyl ether (1.6 liters) at 5°–10° C. was added dropwise over 30 minutes 10.6 ml of bromine. The mixture was stirred at 5°–10° C. for 30 minutes and then allowed to warm to room temperature. After 2 hours tlc (CH$_2$Cl$_2$) indicated formation of less polar products and only a trace of starting material remaining. The reaction mixture was washed with water (1 liter), saturated NaHCO$_3$ (500 ml), and brine (500 ml), dried over MgSO$_4$, and concentrated in vacuo to a yellow solid. The crude product was purified by silica gel flash column chromatography on 2.4 Kg fine silica gel, eluting with a gradient system consisting of 3:1 hexanes/dichloromethane followed by 2:1 hexanes/dichloromethane and finally 30% hexanes/dichloromethane. This afforded title product as a yellow solid in 80% yield.

PREPARATION 13

1-Amino-5-methylcyclohex-1-en-3-one

5-Methyl-1,3-cyclohexanedione (40 g, 0.32 mol) was dissolved in 500 ml of benzene at 70° C. The solution was heated at reflux for 2 hours, during which NH$_3$ was bubbled through the reaction mixture and formed H$_2$O was collected in a Dean-Stark trap. The mixture was then cooled to 0° C. and title product recovered by filtration, 39.8 g, m.p. 165°–169° C. $^1$H-NMR(DMSO-d$_6$)delta(ppm): 0.98 (s, 3H), 1.6–1.88 (2H), 2.14–2.38 (2H), 3.14–3.6 (1H), 4.93 (s, 1H), 6.2–7.2 (m, 2H).

PREPARATION 14

7,8Dihydro-7-methyl-3-nitro-5(6H)-quinolone

Sodium nitromalonaldehyde (*Org. Synth. Coll.*, vol. 4, p. 844; 42.4 g, 0.269 mol) was dissolved in 200 ml of dimethylformamide and the resulting solution dried over 4A-type molecular sieves, recovered by filtration with 100 ml of the same solvent for wash. To the combined filtrate and wash was added pyridine (91 ml, 89 g, 1.13 mol) and the mixture cooled to −5° C. Tosyl chloride (53 g, 0.277 mol) in 200 ml of dimethylformamide was added dropwise, maintaining a temperature of −5° to −8° C., and the reaction mixture allowed to warm to room temperature. The title product of the preceding Preparation (33.6 g, 0.270 mol), dissolved by warming in 200 ml of dimethylformamide and added in a steady stream to the reaction mixture, which was then stirred for 18 hours at room temperature, then poured into 2 liters of ice and water and extracted 2×1 liter of ethyl acetate. The organic layers wre combined, dried over MgSOand stripped to yield present title product, 33 g (61%), m.p. 64°–67° C.

PREPARATION 15

3-Amino-7-8-dihydro-7-methyl-5(6H)-quinolone

Title product of the preceding Preparation (27 g) was placed in a 250 ml Parr bottle with 830 ml absolute ethanol and 9.0 g 10% Pd/C. This was then agitated on a Parr apparatus under 50 psig H$_2$ for 2 hours at room temperature. The catalyst was recovered by filtration over diatomaceous earth and the filtrate was concentrated to dryness. The resulting brown solid was flash chromatographed by first dissolving in CH$_3$OH, adding 50 ml dry 32–63 micron silica gel and concentrating to dryness. The resulting material was then charged dry onto a 30 cm×15 cm column of fresh silica gel which had been wet packed with 1% triethylamine in 19:1 CH$_2$Cl$_2$ isopropanol. The column was eluted with the same solvent system. Middle product-containing fractions were combined and stripped to yield present title product, MS (m/e) calculated: 176.0950, found: 176.0944; tlc (19:1 CH$_2$Cl$_2$:C$_2$H$_5$OH) Rf 0.32.

PREPARATION 16

7,8-Dihydro-7-methyl-5(6H)-quinolone-6-diazonium Hexafluorophosphate

At room temperature, title product of the preceding Preparation (15.26 g) was placed in a 500 ml 3-necked flask equipped with a mechanical stirrer, dropping funnel and venting line placed up the back of the fume hood. Then 6.93 ml glacial acetic acid was added. 159 Ml of 3.48N HCl was then added all at once whereupon the reaction mixture became a clear deep red solution. The latter was then cooled to 0° C. at which time some solid precipitated out of solution. To this slurry, still at 0° C., was then added 5.98 g NaNO$_2$ in 35 ml H$_2$O, dropwise over 5–10 minutes, and the resulting mixture stirred at 0° C. for 30 minutes. Still maintaining 0° C., 15.24 ml HPF$_6$ (60 weight % in H$_2$O) was added over 5 minutes. A light brown precipitate formed immediately. Vigorous stirring was continued for 10–15 minutes after addition was complete. The resulting solid was filtered, washed with 2×25 ml cold H$_2$O, 2×25 ml ether and then dried under high vacuum overnight over P$_2$O$_5$ to yield 25.62 g (89%) of present title product, m.p. 175°–176.5° C.

PREPARATION 17

7,8-Dihydro-3-hydroxy-7-methyl-5(6H)-quinolone

Title product of the preceding Example (25.62 g) was added in 0.5 g portions to 500 ml of boiling 5% H$_2$SO$_4$ over a time period (2.5 hours in this instance) which avoided excessive foaming due to N$_2$ evolution. The reaction mixture was heated at reflux for an additional 40 minutes, then cooled to 0° C. and adjusted to pH 7 with 6N NaOH (160 ml required in this instance). The reaction mixture was extracted 3×250 ml ethyl acetate. In the first extraction, the emulsion was broken by filtration over diatomaceous earth. The organic extracts were combined, dried over MgSO$_4$, stripped to solids, and the residue dissolved in CH$_3$OH, slurried with silica gel, stripped and flash chromatographed as in the preceding Example, using 19:1 CH$_2$Cl$_2$:isopropanol as eluant to yield present title product, 9.2 g (67%), m.p. 210.5°–212° C.

PREPARATION 18

3-Benzyloxy-7,8-dihydro-7-methyl-5(6H)-quinolone

By the method of Preparation 4, the product of the preceding Preparation was converted to present title product in 78% yield, m.p. 80.5°–81.5° C. MS (m/e) calculated: 267.1259, found: 267.1261.

PREPARATION 19

2-Chloromethylquinoxaline

2-Methylquinoxaline (8.94 g) was combined with 50 ml CCl$_4$ and 6.5 g Na$_2$CO$_3$ in a 125 ml beaker. This was heated to 68° C. and then Cl$_2$ was introduced via an inverted funnel so that the Cl$_2$ was bubbled very slowly. This was continued for 1 hour and then the reaction mixture was cooled to 20° C. in an ice bath and partitioned between ether and saturated NaHCO$_3$ solution. The ether was separated, dried over MgSO$_4$, and concentrated to dryness. The residue was immediately flashed down a column packed with 20 cm of 32–63 micron silica gel (the column having a diameter of 8 cm) using 1:1 ether:hexane as eluant. After a 1 liter forerun, 250 ml fractions were collected. Fractions 3–5 were combined and concentrated to yield 2.58 g (23%) of title product as a yellow solid; tlc (3:7 ethyl acetate:CH$_2$Cl$_2$) Rf 0.65. $^1$H-NMR(CDCl$_3$)delta(ppm): 4.86 (s, 2H), 7.74–7.78 (m, 2H), 8.02–8.16 (m, 2H), 9.0 (m, 1H).

PREPARATION 20

2-Bromo-3,4-dihydro-7-methoxy-1(2H)-naphthalenone

To a 10° C. solution of 25 g (0.142 mol) of 7-methoxy-3,4-dihydro-1(2H)-naphthalenone in 1 liter ether was added dropwise (maintaining reaction temperature at about 10° C.) 37.9 g (0.237 mol) of bromine. The reaction solution was concentrated on a rotating evaporator and the residue crystallized from ether to give 31.6 g (87%) of present title compound, m.p. 79°–80° C.

MS (m/e) 256 and 254 (M+), 174, 173, 148, 131, 120, 115 and 103. Ir (CHCl$_3$) 1680, 1610 cm$^{-1}$. $^1$H-NMR(CDCl$_3$)delta(ppm): 2.2°–2.7 (m, 2H), 2.9–3.5 (m, 2H), 3.95 (s, OCH$_3$), 4.78 (t, J=4 Hz, CHBr), 7.0–7.4 (m, 2ArH) and 7.58 (bs, ArH).

Analysis calculated for $C_{11}H_{11}BrO_2 \cdot \frac{1}{4}H_2O$:
C, 50.89; H, 4.46%.
Found C, 50.71; H, 4.36%.

PREPARATION 21

6-Benzyloxy-3-methylene-4-chromanone

A solution of 9.2 g of 6-benzyloxy-4-chromanone, dimethylamine hydrochloride and 1.3 g of paraformaldehyde in 100 ml of acetic acid was heated on a steam bath for 5 hours. The volatiles were evaporated in vacuo and the residue was purified on silica gel, eluting with $CH_2Cl_2$, to give 3.7 g of product, Rf $(CH_2Cl_2)=0.5$. $^1$H-NMR(CDCl$_3$)delta(ppm): 4.95 (s, 2H), 5.05 (s, 2H), 5.55 (s, 1H), 6.30 (s, 1H), 6.80–7.60 (m, 8H).

PREPARATION 22

3-Bromo-2-(bromomethyl)-6-methyl pyridine and

3-Bromo-6-(bromomethyl)-2-methyl pyridine

To a 25 ml round bottomed flask equipped with a stir bar and condenser, under an inert atmosphere, were added 1.4 g (7.35 mmol) of 3-bromo-2,6-lutidine, 1.21 g (6.77 mmol) of N-bromosuccinimide, 4.5 ml of carbon tetrachloride, and 10 mg (0.04 mmol) of benzoyl peroxide. The resulting mixture was refluxed overnight. Tlc at this point indicated that there still was starting material present, so 0.7 g (3.9 mmol) of N-bromosuccinimide was added and the reaction mixture refluxed for an additional 4 hours. The precipitate was filtered off and washed 2×50 ml CCl$_4$ (hot). The filtrate was concentrated to an oil and the crude product was then purified by flash chromatography on 200 g silica gel with 3:1 hexane:$CH_2Cl_2$ as eluant to yield the two title compounds, 218 mg (11%) yield of the 2-(bromomethyl) derivative and 285 mg (14%) yield of the 6-(bromomethyl) derivative, tlc (3:1 hexane:$CH_2Cl_2$) Rf 0.07 and 0.13, respectively.

2-(bromomethyl) derivative. $^1$H-NMR(DMSO-d$_6$)delta(ppm): 7.99 (d, J=7.8 Hz, 1H), 7.19 (d, J=7.8 Hz, 1H), 4.71 (s, 2H), 2.46 (s, 3H).

6-(bromomethyl) derivative. $^1$H-NMR(DMSO-d$_6$)delta(ppm): 8.00 (d, J=7.8 Hz, 1H), 7.32 (d, J=7.8 Hz, 1H), 4.63 (s, 2Hz), 2.56 (s, 3H).

PREPARATION 23

4-Methoxy-2-methylpyridine N-Oxide

With stirring, sodium pellets (3.95 g, 0.172 mol), maintained dry under hexane, were added to 540 ml dry methanol, under N$_2$. Following dissolution, the mixture was diluted with 900 ml methanol, 4-nitro-2-methylpyridine N-oxide (26.0 g, 0.169 mol) was added, and the mixture heated at reflux for 1 hour, cooled to room temperature and acidified with 18 ml glacial acetic acid. After stirring 15 minutes, the reaction mixture was stripped of solvent, the orange residue taken up in 300 ml of H$_2$O, neutralized with saturated NaHCO$_3$, reconcentrated to dryness, and the residue triturated 5×50 ml of ethanol. The ethanol triturates were combined, stripped to dryness, and the residue restripped 3×50 ml toluene to yield solids (36.1 g) which were chromatographed on silica gel using 6:1 $CH_2Cl_2$:$CH_3OH$ as eluant to yield purified title product, 21.14 g; MS 139 (M+).

PREPARATION 24

2-Acetoxy-4-methoxypyridine

Title product of the preceding Preparation (21.14 g) was refluxed in 100 ml of acetic anhydride for 45 minutes, then stripped in vacuo. The residue was taken up in 100 ml of water and extracted 4×100 ml of CHCl$_3$. The organic layers were combined, dried (Na$_2$SO$_4$), stripped and the residue oil chromatographed on silica gel gradiently eluted with 3:2, 7:1 and 2:1 ethyl acetate:toluene to yield purified title product as an oil, 20.76 g; tlc Rf 0.9 (6:1 $CH_2Cl_2$:$CH_3OH$); MS 181 (M+).

PREPARATION 25

2-Hydroxymethyl-4-methoxypyridine

Title product of the preceding Preparation (20.75 g, 0.114 mol) and sodium methoxide (9.23 g, 0.171 mol) were combined in 110 ml methanol and heated under reflux for 65 minutes. The mixture was cooled, stripped in vacuo, the residue taken up in 100 ml H$_2$O, neutralized with 1N HCl and extracted with 3×70 ml of ethyl acetate. The organic layers were combined, dried (Na$_2$SO$_4$) and stripped to yield title product as a solid, 14.2 g.

PREPARATION 26

4-Methoxy-2-picolyl Chloride

To title product of the preceding Preparation (500 mg, 3.6 mmol) in 6 ml $CH_2Cl_2$, stirring under N$_2$, was added dropwise 0.26 ml (3.6 mmol) of SOCl$_2$ over 5 minutes, then stirred for 20 minutes, combined with 20 ml H$_2$O, neutralized with saturated NaHCO$_3$ and extracted with 25 ml CHCl$_3$. The organic layer was dried (MgSO$_4$) and stripped at low temperature to yield title product as an oil, 494 mg, used immediately in the next chemical step.

PREPARATION 27

6-Benzyloxy-3-bromo-4-chromanone

By the method of Preparation 12, 6-methoxy-4-chromanone (200 g, 0.79 mol) was converted to present title product, purified by chromatography on silica gel gradiently eluted with 1:1, 2:1, 3:1 and 1:0 $CH_2Cl_2$:hexane, recrystallized from isopropyl ether, 41.4 g, tlc Rf 0.4 ($CH_2Cl_2$).

PREPARATION 28

3-Hydroxy-2-methylpyridine

2-Acetylfuran (21.2 g), concentrated NH$_4$OH (325 ml) and H$_2$O (175 ml) were combined and heated in an autoclave at 150° C. (observed pressure, 262 psig) for 22 minutes. The mixture was cooled, stripped and the residue chromatographed on silica gel eluting sequentially with 1:19 and then 1:9 $CH_3OH$:$CH_2Cl_2$ to yield 13.2 g of title product. Recrystallization from isopropanol gave 9.68 g of purified title product in two crops; tlc Rf 0.3 (1:9 $CH_3OH$:$CH_2Cl_2$).

We claim:
1. A racemic or optically active compound having the structural formula

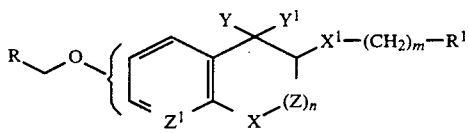 (I)

wherein
n is 0 or 1;
m is 0 or an integer from 1 to 3;
X is $CH_2$, O, S, SO, $SO_2$, NH or $N(C_1-C_4)$alkyl;
$X^1$ is $CH_2$, O, S, SO or $SO_2$;
Y and $Y^1$ are taken together and form a carbonyl group, or Y and $Y^1$ are taken separately, Y is hydrogen and $Y^1$ is hydroxy or an acyloxy group which is hydrolyzed to form a hydroxy group under physiological conditions;
Z is $CH_2$, $CHCH_3$, $CH_2CH_2$ or $CH_2CH_2CH_2$;
$Z^1$ is CH or N;
R is 2-, 3-, 4 or 8-quinolyl, or one of said groups mono- or disubstituted on carbon with the same or different substituents which are bromo, chloro, fluoro, $(C_1-C_4)$alkyl, trifluoromethyl, hydroxy, hydroxymethyl or $(C_1-C_4)$alkoxy, or on adjacent carbons with trimethylene, tetramethylene, $-CH_2-O-CH_2-$ or $-O-CH_2-O-$; and
$R^1$ is attached by means of aromatic or heteroaromatic carbon and is phenyl, naphthyl, pyridyl, pyridazinyl, pyrymidinyl, pyrrolyl, N-[$(C_1-C_4)$alkyl]pyrrolyl, pyrazolyl, 1-[$(C_1-C_4)$alkyl]pyrazolyl, imidazolyl, 1-[$(C_1-C_4)$alkyl]imidazolyl, furyl, oxazolyl, isoxazolyl, thienyl, thiazolyl, isothiazolyl; or, only when either $X^1$ is $CH_2$ or m is at least 2, $R^1$ is attached by means of hetrocyclic nitrogen and is 1-pyrrolyl, 1-pyrazolyl, or 1-imidazolyl; or $R^1$ is one of said groups which is mono- or disubstituted on carbon with the same or different groups which are bromo, chloro, fluoro, hydroxy, hydroxymethyl, $CF_3$, $(C_1-C_4)$alkyl, $(C_1-C_4)$alkoxy, carboxy, [$(C_1-C_4)$alkoxy]carbonyl, or substituted on adjacent carbons with trimethylene, tetramethylene, $-CH_2-O-CH_2-$ or $-O-CH_2-O-$; or substituted on tertiary nitrogen to form an N-oxide;
a pharmaceutically acceptable acid addition salt thereof; or
a pharmaceutically acceptable cationic salt when the compound contains a carboxy group.

2. A compound of claim 1 having the formula

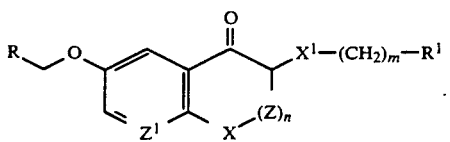

3. A compound of claim 2 wherein n is 1, m is 0, X and $X^1$ are each independently $CH_2$ or O, Z is $CH_2$, R is 2-quinolinyl, or 6-fluoro-2-quinolyl and $R^1$ is 2- or 3-pyridyl, 3- or 4-methoxyphenyl or 3-carboxyphenyl.

4. The racemic compound of claim 3 wherein X is O, $X^1$ is $CH_2$, is CH, R is 2-quinolyl and $R^1$ is 3-pyridyl.

5. A compound of claim 1 having the formula

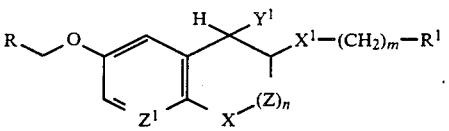

6. A compound of claim 5 wherein $Y^1$ is an acyloxy group in which the acyl moiety is the alpha-aminoacyl residue of a naturally occurring L-alpha-amino acid,

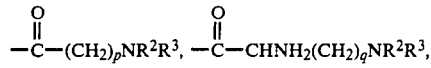

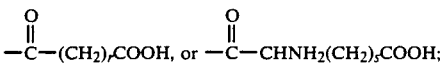

$R^2$ and $R^3$ are taken separately and are each independently hydrogen or $(C_1-C_4)$alkyl, or $R^2$ and $R^3$ are taken together with the nitrogen to which they are attached to form a pyrrolidine, piperidine, perphydroazepin or morpholine ring;
p is an integer from 1 to 4;
q is an integer from 1 to 3;
r is an integer from 2 to 3; and
s is an integer from 1 to 3.

7. A compound of claim 6 wherein n is 1, m is 0, X and $X^1$ are each independently $CH_2$ or O, Z is $CH_2$, $Z^1$ is CH, R is 2-quinolyl, or 6-fluoro-2-quinolyl and $R^1$ is phenyl, 3-methoxyphenyl, 4-methoxyphenyl, 3-methoxycarbonylphenyl, 4-methoxycarbonylphenyl, 2-pyridyl, 3-pyridyl or 6-methyl-3-pyridyl.

8. A compound of claim 6 wherein the acyl moiety

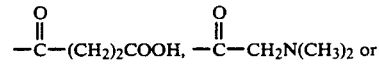

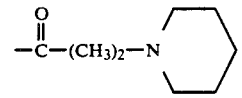

9. The compound of claim 8 wherein X and $X^1$ are each O, R is 2-quinolyl, $R^1$ is phenyl and the acyl moiety is

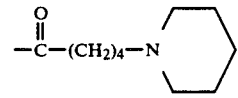

10. The compound of claim 8 wherein X and $X^1$ are each O, R is 2-quinolyl, $R^1$ is phenyl and the acyl moiety is

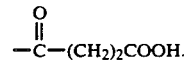

11. A compound of claim 5 wherein $Y^1$ is hydroxy.

12. A compound of claim 11 wherein n and m are each 1, X and $X^1$ are each independently $CH_2$ or O, Z is $CH_2$, $Z^1$ is CH, R is 2-quinolyl, or 6-fluoro-2-quinolyl and $R^1$ is phenyl.

13. The racemic cis-compound of claim 12 wherein X and $X^1$ are each O and R is 2-quinolyl.

14. A compound of claim 11 wherein n is 1, m is 0, X and $X^1$ are each independently $CH_2$ or O, Z is $CH_2$, $Z^1$ is CH, R is 2-quinolyl, or 6-fluoro-2-quinolyl, and $R^1$ is phenyl, 3-methoxyphenyl, 4-methoxyphenyl, 3-methoxycarbonylphenyl, 4-methoxycarbonylphenyl, 3-carboxyphenyl, 4-carboxyphenyl, 2-pyridyl, 3-pyridyl or 6-methyl-3-pyridyl.

15. A racemic or optically active compound of claim 14 having the relative stereochemical formula

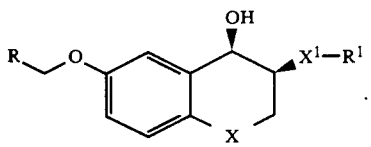

16. The racemic compound of claim 15 wherein X is O, $X^1$ is $CH_2$, R is 2-quinolyl and $R^1$ is 3-pyridyl.

17. The racemic or optically active compounds of claim 15 wherein X is O, $X^1$ is $CH_2$, R is 2-quinolyl and $R^1$ is 3-carboxyphenyl.

18. A compound of calim 15 wherein X and $X^1$ are each O, R is 6-fluoro-2-quinolyl and $R^1$ is 4-methoxyphenyl.

19. An optically active compound of claim 15 having the absolute stereochemical formula

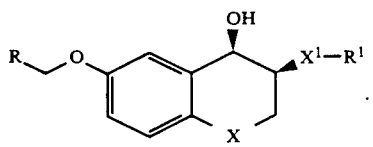

20. The compound of claim 19 wherein X is O, $X^1$ is $CH_2$, R is 2-quinolyl and $R^1$ is 3-pyridyl.

21. The compound of claim 19 wherein X is O, $X^1$ is $CH_2$, R is 6-fluoro-2-quinolyl and $R^1$ is 3-pyridyl.

22. A compound of claim 19 wherein X and $X^1$ are each O, R is 2-quinolyl and $R^1$ is 3-pyridyl or 6-methyl-3-pyridyl.

23. The compound of claim 19 wherein X and $X^1$ are each O, R is 2-quinolyl and $R^1$ is 4-methoxyphenyl.

24. A racemic or optically active compound of claim 14 having the relative stereochemical formula

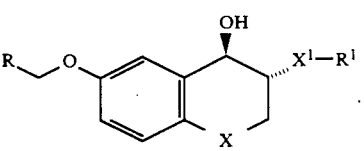

25. The compound of claim 24 wherein X and $X^1$ are each $CH_2$, R is 2-quinolyl and $R^1$ is 3-pyridyl.

26. The compound of claim 24 wherein X is O, $X^1$ is $CH_2$, R is 2-quinolyl and $R^1$ is 3-pyridyl.

27. The compound of claim 24 wherein X is O, $X^1$ is $CH_2$, R is 2-quinolyl and $R^1$ is 2-pyridyl.

28. The compounds of claim 24 wherein X and $X^1$ are each O, R is 2-quinolyl and $R^1$ is 3-methoxyphenyl.

29. A pharmaceutical composition for administration to a mammal which comprises a 5-lipoxygenase inhibiting and/or leukotriene D4 receptor blocking amount of a compound of claim 1 and a pharmaceutically acceptable carrier.

30. A method of inhibiting 5-lipoxygenase and/or blocking leukotriene D4 receptors in a mammal in need of such inhibition and/or blocking which comprises administering to said mammal a 5-lipoxygenase inhibiting and/or leukotriene D4 receptor blocking amount of a compound of claim 1.

31. A method of claim 30 wherein the mammal is a human suffering from asthma, said compound administered to prevent or relieve the symptoms of said asthma.

32. A method of claim 34 wherein the mammal is suffering from arthritis, said compound administered to prevent or relieve the symptoms of said arthritis.

33. A method of claim 30 wherein the mammal is a human suffering from psoriasis, said compound administered to prevent or relieve the symptoms of said psoriasis.

34. A method of claim 30 wherein the mammal is suffering from gastrointestinal distress, said compound administered to prevent or relieve gastrointestinal ulcers.

35. A method of claim 34 wherein the mammal is suffering from cardiovascular disease, said compound administered to prevent or relieve myocardial infarction.

* * * * *

UNITED STATES PATENT AND TRADEMARK OFFICE
CERTIFICATE OF CORRECTION

PATENT NO. : 5,059,609

DATED : October 22, 1991

INVENTOR(S) : James F. Eggler, Anthony Marfat and Lawrence S. Melvin, Jr.

It is certified that error appears in the above-identified patent and that said Letters Patent is hereby corrected as shown below:

Column 1, Line 7

-- This is a continuation-in-part of International Application No. PCT/US87/02745, filed October 19, 1987, now abandoned. --

Signed and Sealed this

Twenty-sixth Day of October, 1993

Attest:

BRUCE LEHMAN

*Attesting Officer*  *Commissioner of Patents and Trademarks*